United States Patent
Badley

(10) Patent No.: US 11,136,402 B2
(45) Date of Patent: Oct. 5, 2021

(54) TRAILSHORT ANTIBODY AND METHODS OF USE

(71) Applicant: Mayo Foundation for Medical Education and Research, Rochester, MN (US)

(72) Inventor: Andrew D. Badley, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 7 days.

(21) Appl. No.: 16/485,056

(22) PCT Filed: Feb. 8, 2018

(86) PCT No.: PCT/US2018/017385
§ 371 (c)(1),
(2) Date: Aug. 9, 2019

(87) PCT Pub. No.: WO2018/148383
PCT Pub. Date: Aug. 16, 2018

(65) Prior Publication Data
US 2019/0367626 A1 Dec. 5, 2019

Related U.S. Application Data

(60) Provisional application No. 62/457,614, filed on Feb. 10, 2017, provisional application No. 62/512,627, filed on May 30, 2017.

(51) Int. Cl.
*C07K 16/24* (2006.01)
*A61K 39/395* (2006.01)
(Continued)

(52) U.S. Cl.
CPC .... *C07K 16/2875* (2013.01); *A61K 39/39558* (2013.01); *C07K 16/2878* (2013.01);
(Continued)

(58) Field of Classification Search
None
See application file for complete search history.

(56) References Cited

U.S. PATENT DOCUMENTS 6,521,228 B1 * 2/2003 Wiley .............. C07K 14/70575
424/145.1
8,008,261 B2 8/2011 Badley et al.
(Continued)

FOREIGN PATENT DOCUMENTS

| KR | 100804126 | 2/2008 |
| WO | WO 2011/083175 | 7/2011 |
| WO | WO 2015/100366 | 7/2015 |

OTHER PUBLICATIONS

Mérino et al., TRAIL in cancer therapy: present and future challenges, Expert Opin. Ther. Targets, 11(10): 1299-1314, Oct. 2007.*
(Continued)

*Primary Examiner* — Claire Kaufman
(74) *Attorney, Agent, or Firm* — Fish & Richardson P.C.

(57) ABSTRACT

This document provides antibodies against tumor necrosis factor (TNF)-related apoptosis-inducing ligand (TRAIL) short, and more particularly to humanized TRAILshort antibodies that can neutralize TRAILshort. For example, materials and methods for using one or more humanized TRAILshort antibodies to induce apoptosis (e.g., via TRAIL mediated cell death, natural killer (NK) cytotoxicity, and/or CD8+ T cell killing) are provided.

15 Claims, 44 Drawing Sheets

Specification includes a Sequence Listing.

(51) Int. Cl.
*C07K 16/28* (2006.01)
*A61K 38/19* (2006.01)

(52) U.S. Cl.
CPC ........ *A61K 38/191* (2013.01); *C07K 2317/24* (2013.01); *C07K 2317/73* (2013.01); *C07K 2317/75* (2013.01); *C07K 2317/76* (2013.01)

(56) References Cited

U.S. PATENT DOCUMENTS

| | | | |
|---|---|---|---|
| 2002/0061525 | A1 | 5/2002 | Yelin et al. |
| 2002/0155109 | A1 | 10/2002 | Lynch |
| 2003/0059429 | A1 | 3/2003 | Ames et al. |
| 2010/0172914 | A1 | 7/2010 | Badley et al. |
| 2015/0218274 | A1 | 8/2015 | Sabatos-Peyton et al. |

OTHER PUBLICATIONS

Aboulnasr et al., Human cancers express TRAILshort, a dominant negative TRAIL splice variatn, which impairs immune effector cell killing of tumor cells, Clin. Cancer Res. 26 (21) 5759-5771 and suppl. material, 2020.*
Liabakk et al., Development, characterization and use of monoclonal antibodies against sTRAIL: measurement of sTRAIL by ELISA, ournal of Immunological Methods 259: 119-128, 2002.*
Aboulnasr et al., "Abstract No. 273: TRAILshort Reduces the Cytotoxic Capacity of NK Cells," Poster, Presented at Conference on Retroviruses and Opportunistic Infections, Seattle, WA, Top Antivir. Med., Feb. 13-16, 2017, 1 page.
Badley, "Evaluating the Role of the Novel Apoptosis Inhibitor TRAILshort, in Maintaining HIV Persistence," NIH, Project No. 5R01AI120698-02, Jun. 15, 2015, 3 pages.
Carter et al., "Humanization of an anti-p185HER2 antibody for human cancer therapy," Proc. Nat'l. Acad. Sci. USA, 89(10):4285-9, May 1992.
Cha et al., "2.8 A Resolution Crystal Structure of Human TRAIL, a Cytokine With Selective Antitumor Activity," Immunity, 11:253-261, Aug. 1999.
Dall'Acqua et al., "Antibody Humanization by Framework Shuffling," Methods, 36(1):43-60, May 2005.
Damschroder et al., "Framework Shuffling of Antibodies to Reduce Immunogenicity and Manipulate Functional and Biophysical Properties," Mol. Immunol., 44(11):3049-3060, Apr. 2007.
Deng et al., "Activation of the IκB kinase complex by TRAF6 requires a dimeric ubiquitin-conjugating enzyme complex and a unique polyubiquitin chain," Cell, 103(2):351-361, Oct. 2000.
Green et al., "Production of Polyclonal Antisera," in Immunochemical Protocols (Manson, ed.), pp. 1-5 (Humana Press 1992).
Harlow et al., Antibodies: A Laboratory Manual, p. 726 (Cold Spring Harbor Pub. 1988).
Huber et al., "Human colorectal cancer cells induce T-cell death through release of proapoptotic microvesicles: role in immune escape," Gastroenterology, 128(7):1796-1804, Jun. 2005.
Huse et al., "Generation of a large combinatorial library of the immunoglobulin repertoire in phage lambda," Science, 246(4935):1275-1281, Dec. 1989.
Hwang et al., "Use of Human Germline Genes in a CDR Homology-Based Approach to Antibody Humanization," Methods, 36(1):35-42, May 2005.

International Preliminary Report on Patentability in International Application No. PCT/US2018/017385 dated Aug. 22, 2019, 10 pages.
International Search Report and Written Opinion in International Application No. PCT/US2018/017385 dated Jun. 6, 2018, 19 pages.
Jones et al., "Replacing the complementarity-determining regions in a human antibody with those from a mouse," Nature, 321(6069):522, May 1986.
Kashmiri et al., "SDR Grafting—A New Approach to Antibody Humanization," Methods, 36(1):25-34, May 2005.
Kohler and Milstein, "Continuous cultures of fused cells secreting antibody of predefined specificity," Nature, 256(5517):495, Aug. 1975.
Komander et al., "Breaking the chains: structure and function of the deubiquitinases," Nat. Rev. Mol. Cell Biol., 10(8):550-563, Aug. 2009.
Lang et al., "Binding Studies of TNF Receptor Superfamily (TNFRSF) Receptors on Intact Cells," J. Biol. Chem., 291(10):5022-5037, Mar. 2016.
Lazar et al., "A Molecular Immunology Approach to Antibody Humanization and Functional Optimization," Mol. Immunol., 44:1986-1998, Mar. 2007.
Orlandi et al., "Cloning immunoglobulin variable domains for expression by the polymerase chain reaction," Proc. Nat'l. Acad. Sci. USA, 86(10):3833-7, May 1989.
Radar et al., "A Phage Display Approach for Rapid Antibody Humanization: Designed Combinatorial V Gene Libraries," Proc. Natl Acad. Sci. USA, 95(15):8910-8915, Jul. 1998.
Riechmann et al., "Reshaping human antibodies for therapy," Nature 332(6162):323, Mar. 1988.
Rosok et al., "A Combinatorial Library Strategy for the Rapid Humanization of Anticarcinoma BR96 Fab," J. Biol. Chem., 271(37):22611-22618, Sep. 1996.
Sandhu, "Protein engineering of antibodies," Crit. Rev. Biotech., 12(5-6):437-62, Jan. 1992.
Schnepple et al., "Isolation of a TRAIL antagonist from the serum of HIV-infected patients," J. Biol. Chem., 286(41):35742-35754, Oct. 2011.
Singer et al., "Optimal humanization of 1B4, an anti-CD18 murine monoclonal antibody, is achieved by correct choice of human V-region framework sequences," J. Immunol., 150(7):2844-57, Apr. 1993.
Taylor et al., "Exosome isolation for proteomic analyses and RNA profiling," Methods Mol. Biol., 728:235-246, Feb. 2011.
Truneh et al., "Temperature-sensitive Differential Affinity of TRAIL for Its Receptors. DR5 Is the Highest Affinity Receptor," J. Biol. Chem., 275(30):23319-23325, Jul. 2000.
Verhoeyen et al., "Reshaping human antibodies: grafting an antilysozyme activity," Science, 239(4847):1534-6, Mar. 1988.
Verma et al., "Inhibition of the TRAIL Death Receptor by CMV Reveals Its Importance in NK Cell-Mediated Antiviral Defense," PLoS Pathog., 10(8):e1004268, Aug. 2014.
Wang and El-Deiry, "TRAIL and apoptosis induction by TNF-family death receptors," Oncogene, 22(53):8628-8633, Nov. 2003.
Zitvogel et al., "Type I interferons in anticancer immunity," Nat. Rev. Immunol., 15(7):405-414, Jul. 2015.
Badley et al., "Altering cell death pathways as an approach to cure HIV infection," Cell Death and Disease, 4(7):e718, Jul. 2013, 11 pages.
Barblu et al., "Reduction of death receptor 5 expression and apoptosis of CD4+ T cells from HIV controllers," Clinical Immunology, 155(1):17-26, Aug. 2014.

* cited by examiner

FIG. 11
A
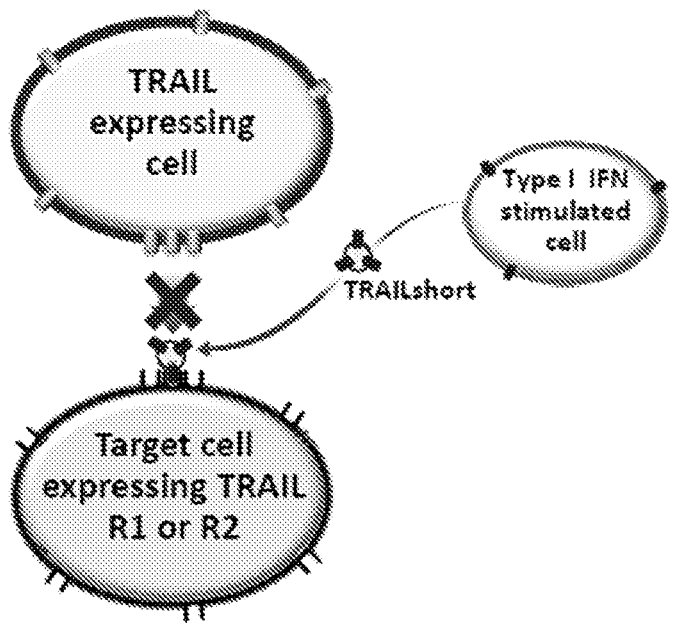
B
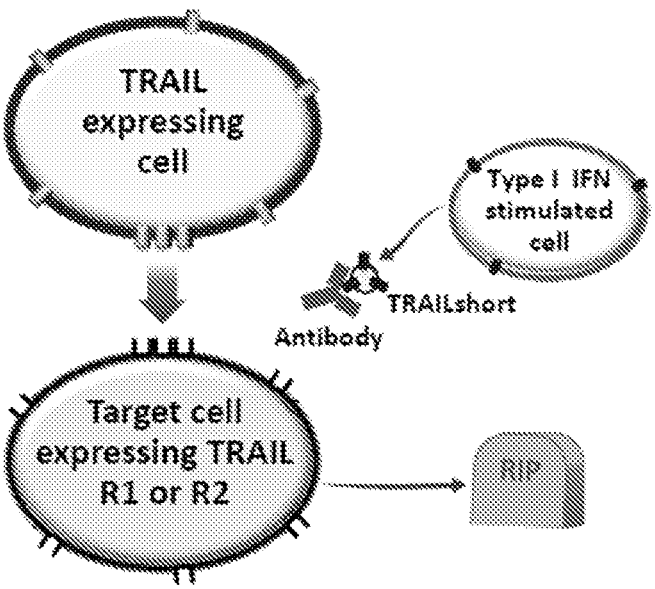

```
              1                                                  50
VH0    (1)   QVQLQQSGPELVKPGASVKISCKASGYIFTNNDMNWVKQRPGQGLEWIGG
VH1    (1)   QVQLVQSGAEVKKPGATVKISCKVSGYIFTNNDMNWVQQAPGKGLEWMGG
VH2    (1)   QVQLVQSGAEVKKPGASVKVSCKASGYIFTNNDMNWVRQAPGQGLEWMGG
VH3    (1)   QVQLVQSGAEVKKPGSSVKVSCKSSGYIFTNNDMNWVRQAPGQGLIWMGG
VH4    (1)   QVQLVESGAEVKMPGASVKVSCKVSGYIFTNNDMNWVRQAPGEGLEWMGG
              51                                                 100
VH0   (51)   IDPGDGRTKYNEKFKGRATLTADKFSNTVYMQLSSLTSENSAVYFCGRGG
VH1   (51)   IDPGDGRTKYNEKFKGRVTITADESTSTAYMELSSLRSEDTAVYFCGRGG
VH2   (51)   IDPGDGRTKYNEKFKGRVTMTRDTSTNTVYMELSSLTSEDTAVYFCGRGG
VH3   (51)   IDPGDGRTKYNEKFKGRVTISADIFSNTAYMELNSLTSEDTAVYFCGRGG
VH4   (51)   IDPGDGRTKYNEKFKGRVTMTEDTSTDTAYMELSSLRSEDTAVYFCGRGG
              101       118
VH0  (101)   YEFGIDYWGQGTSVTVSS
VH1  (101)   YEFGIDYWGQGTLVTVSS
VH2  (101)   YEFGIDYWGQGTTVTVSS
VH3  (101)   YEFGIDYWGQGTTVTVSS
VH4  (101)   YEFGIDYWGQGTTVTVSS
```

B

```
              1                                                  50
VL0    (1)   DIVMTQSPSSLSVSAGEKVTMSCKSSQSLLNSGNQKNSLAWYQQKPGRPP
VL1    (1)   DVVMTQSPDSLAVSLGERATINCKSSQSLLNSGNQKNSLAWYQQKPGQPP
VL2    (1)   DIVMTQSPDSLAVSLGERATINCKSSQSLLNSGNQKNSLAWYQQKPGQPP
VL3    (1)   DIVMTQSPDSLAVSLGERATINCKSSQSLLNSGNQKNSLAWYQQRPGHPP
VL4    (1)   EIVMTQSPDSLAVSLGERATINCKSSQSLLNSGNQKNSLAWYQHKPGRPP
              51                                                 100
VL0   (51)   TLLISGASTRESGVPDRFTGSGSGTDFTLTISSVQAEDLAVYYCQNDHSF
VL1   (51)   KLLIYGASTRESGVPDRFSGSGSGTDFTLTISSLQAEDVAVYYCQNDHSF
VL2   (51)   KLLIYGASTRESGVPDRFSGSGSGTDFTLTISSLQAEDVAVYYCQNDHSF
VL3   (51)   KLLIYGASTRESGVPDRFSGSGSGTDFTLTISSLQAEDVAVYYCQNDHSF
VL4   (51)   KLLIYGASTRESGVPDRFSGSGSGEDFTLTISSLQAEDVAVYYCQNDHSF
              101      113
VL0  (101)   PLTFGAGTKLEIK
VL1  (101)   PLTFGQGTKLEIK
VL2  (101)   PLTFGGGTKLEIK
VL3  (101)   PLTFGGGTKVEIK
VL4  (101)   PLTFGPGTKVDIK
```

| Name | SEQ ID NO: | Sequence |
|---|---|---|
| HC0 | 9 | MGWTLVFLFLLSVTAGVHSQVQLQQSGPELVKPGASVKISCKASGYIFTNNDMNWVKQRPGQGL EWIGGIDPGDGRTKYNEKFKGKATLTADKFSNTVYMQLSSLTSENSAVYFCGRGGYEFGIDYWG QGTSVTVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNVFSCSVMHEALH NHYTQKSLSLSPGK |
| HC1 | 10 | MGWTLVFLFLLSVTAGVHSQVQLVQSGAEVKKPGATVKISCKVSGYIFTNNDMNWVQQAPGKGL EWMGGIDPGDGRTKYNEKFKGRVTITADESTSTAYMELSSLRSEDTAVYYCGRGGYEFGIDYWG QGTLVTVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNVFSCSVMHEALH NHYTQKSLSLSPGK |
| HC2 | 11 | MGWTLVFLFLLSVTAGVHSQVQLVQSGAEVKKPGASVKVSCKASGYIFTNNDMNWVRQAPGQG LEWMGGIDPGDGRTKYNEKFKGRVTMTRDTSTNTVYMELSSLTSEDTAVYFCGRGGYEFGIDYW GQGTTVTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGNVFSCSVMHEAL HNHYTQKSLSLSPGK |
| HC3 | 12 | MGWTLVFLFLLSVTAGVHSQVQLVQSGAEVKKPGSSVKVSCKSSGYIFTNNDMNWVRQAPGQG LDWMGGIDPGDGRTKYNEKFKGRVTISADIFSNTAYMELNSLTSEDTAVYFCGRGGYEFGIDYWG QGTTVTVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNVFSCSVMHEALH NHYTQKSLSLSPGK |
| HC4 | 13 | MGWTLVFLFLLSVTAGVHSQVQLVESGAEVKKPGASVKVSCKVSGYIFTNNDMNWVRQAPGEGL EWMGGIDPGDGRTKYNEKFKGRVTMTEDTSTDTAYMELSSLRSEDTAVYYCGRGGYEFGIDYW GQGTTVTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGNVFSCSVMHEAL HNHYTQKSLSLSPGK |

| Name | SEQ ID NO: | Sequence |
|------|------------|----------|
| LC0 | 22 | MVSSAQFLGLLLLCFQGTRCDIVMTQSPSSLSVSAGEKVTMSCKSSQSLLNSGNQKNSLAWYQQ KPGRPPTLLISGASTRESGVPDRFTGSGSGTDFTLTISSVQAEDLAVYYCQNDHSFPLTFGAGTKL ELKRTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| LC1 | 23 | MVSSAQFLGLLLLCFQGTRCDVVMTQSPDSLAVSLGERATINCKSSQSLLNSGNQKNSLAWYQQ KPGQPPKLLIYGASTRESGVPDRFSGSGSGTDFTLTISSLQAEDVAVYYCQNDHSFPLTFGQGTKL EIKRTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| LC2 | 24 | MVSSAQFLGLLLLCFQGTRCDIVMTQSPDSLAVSLGERATINCKSSQSLLNSGNQKNSLAWYQQK PGQPPKLLIYGASTRESGVPDRFSGSGSGTDFTLTISSLQAEDVAVYYCQNDHSFPLTFGGGTKLE IKRTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC |
| LC3 | 25 | MVSSAQFLGLLLLCFQGTRCDIVMTQSPDSLAVSLGERATINCKSSQSLLNSGNQKNSLAWYQQR PGHPPKLLLYGASTRESGVPDRFSGSGSGTDFTLTISSLQAEDVAVYYCQNDHSFPLTFGGGTKV EIKRTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| LC4 | 26 | MVSSAQFLGLLLLCFQGTRCEIVLTQSPDSLAVSLGERATINCKSSQSLLNSGNQKNSLAWYQHKP GRPPKLLIYGASTRESGVPDRFSGSGSGEDFTLTISSLQAEDVAVYYCQNDHSFPLTFGPGTKVDL KRTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC |

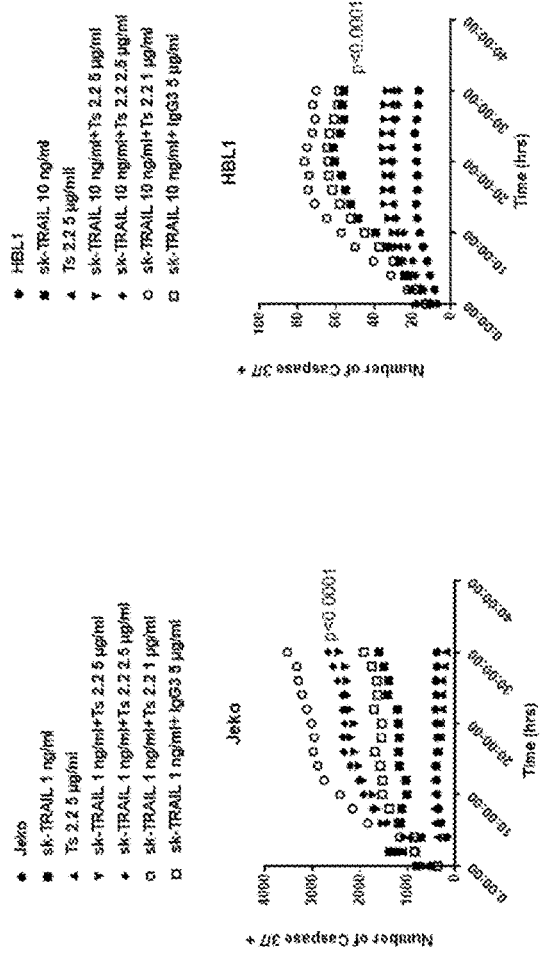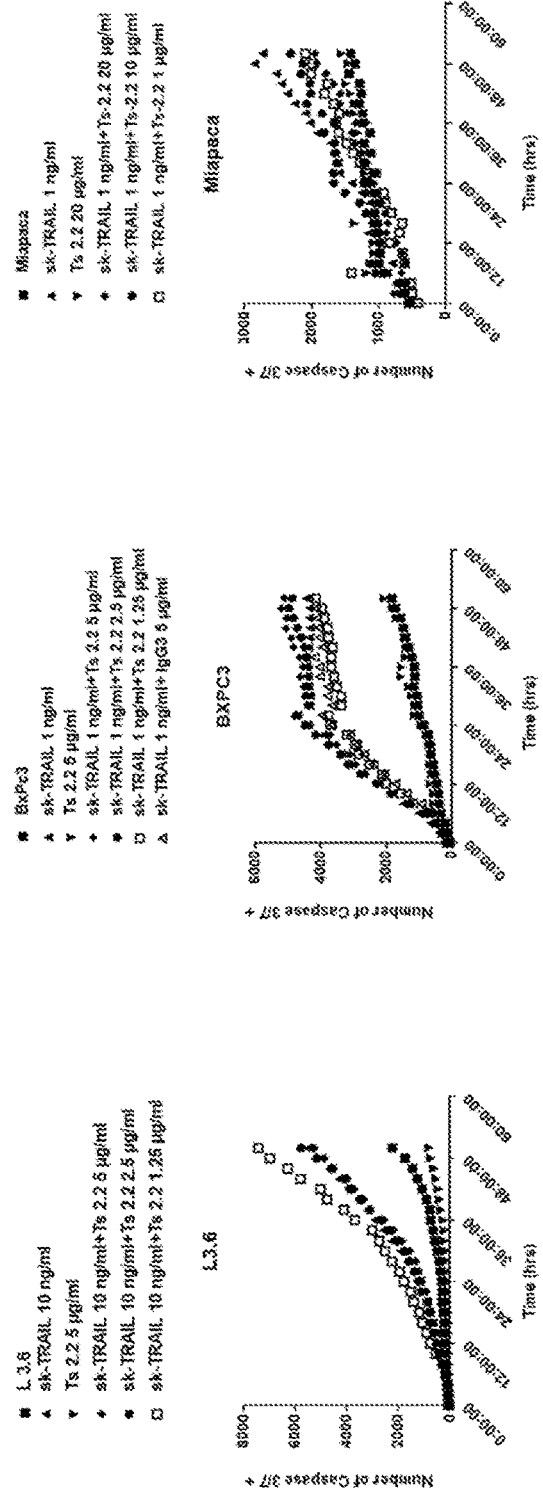
FIG. 15

TCGA - TRAILshort in many tumors
- Bladder
- Breast
- Cervical
- Esophageal
- H&N
- Clear cell kidney
- Renal Papillary cell
- HCC
- Squamous lung
- Ovarian
- Pancreatic
- Sarcoma
- Uterine FIG. 20
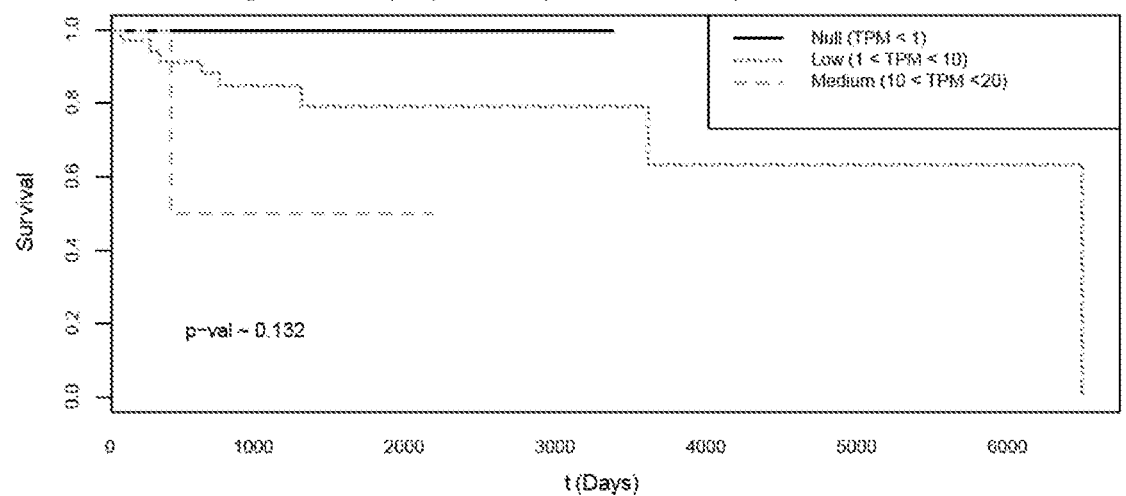
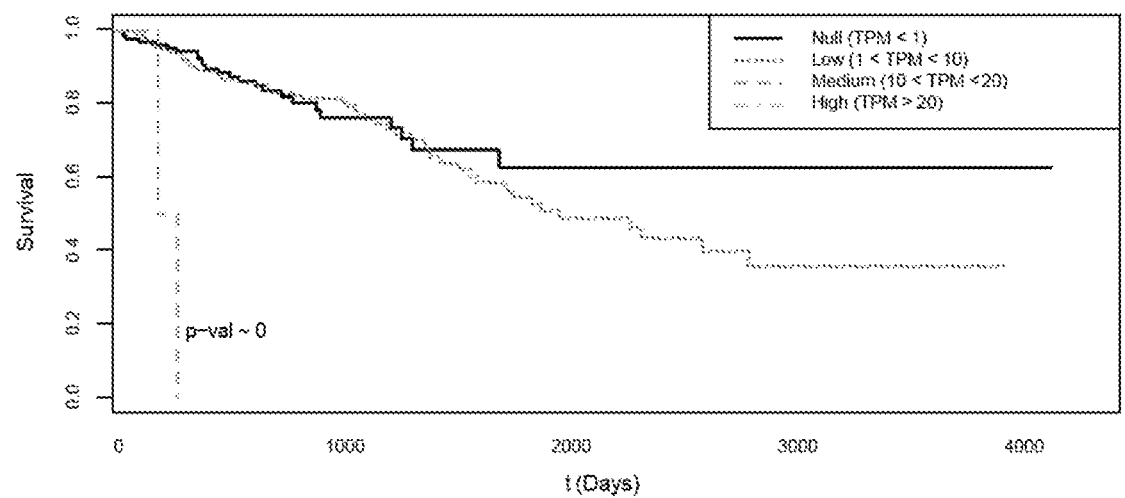

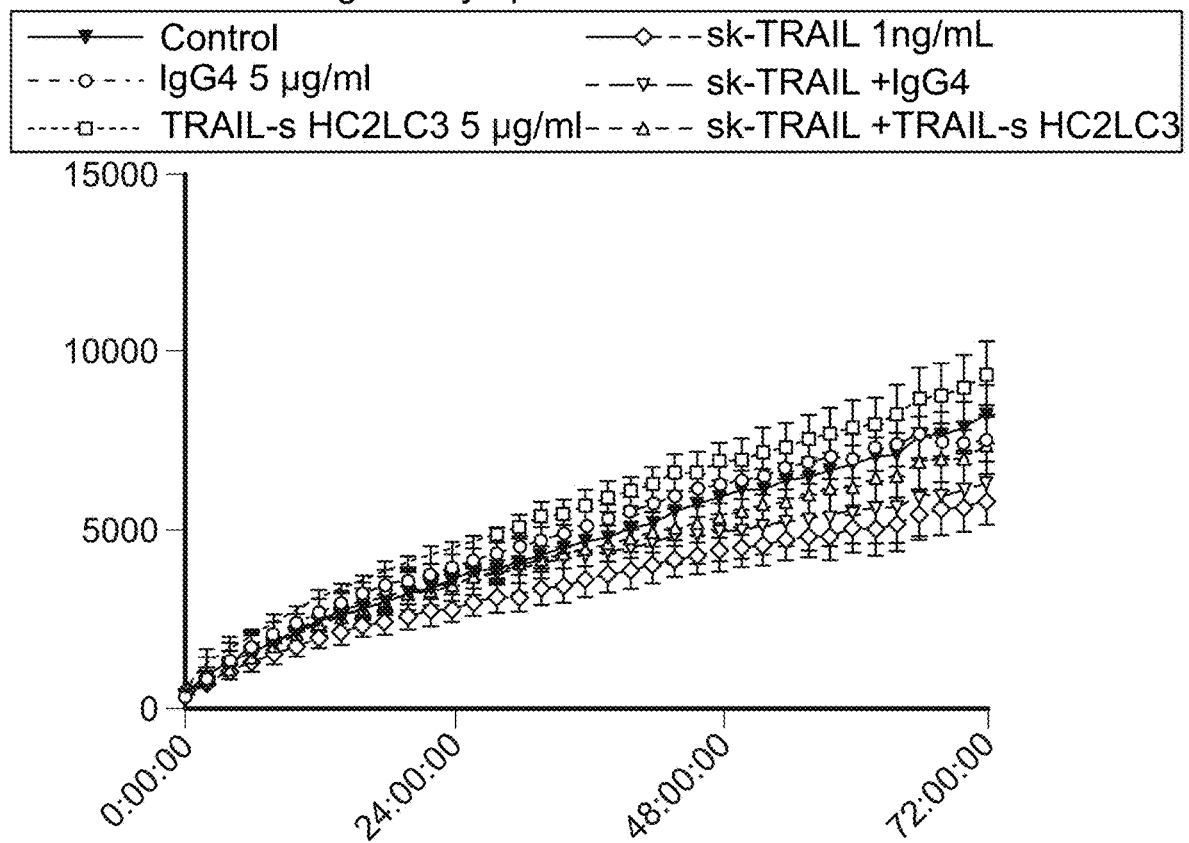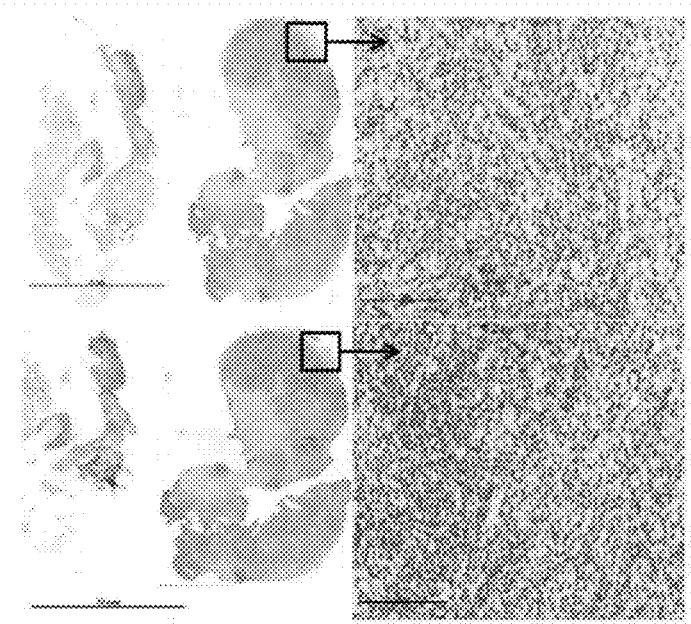
FIG. 23B

FIG. 24
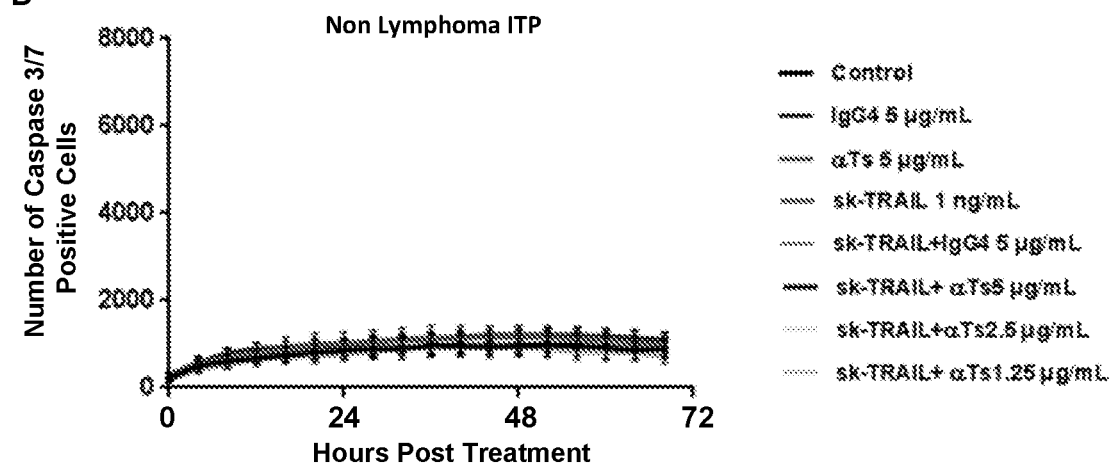
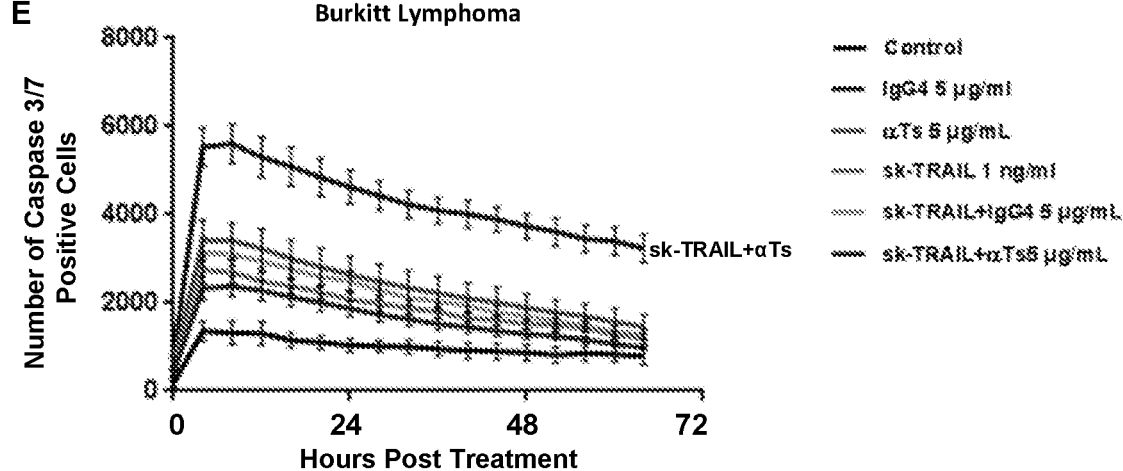
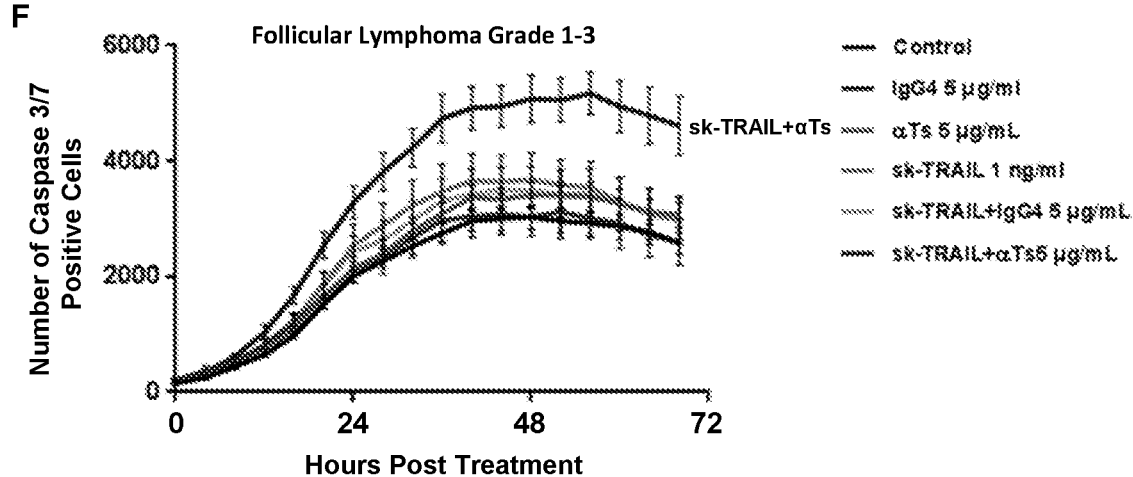

FIG. 24
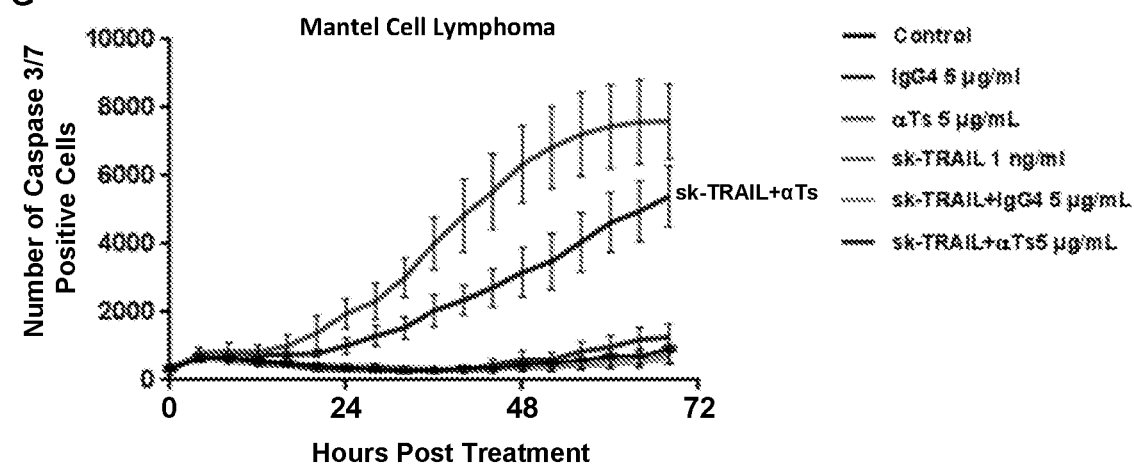
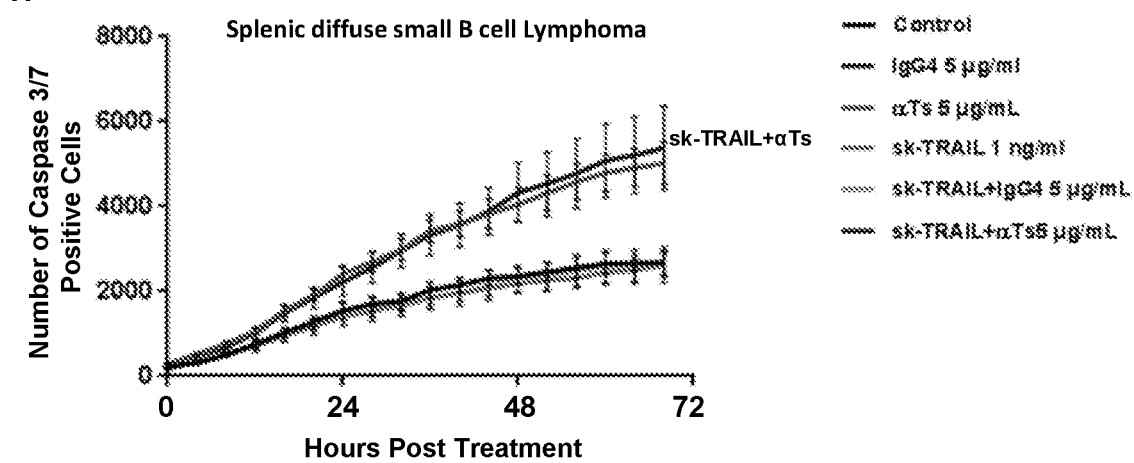
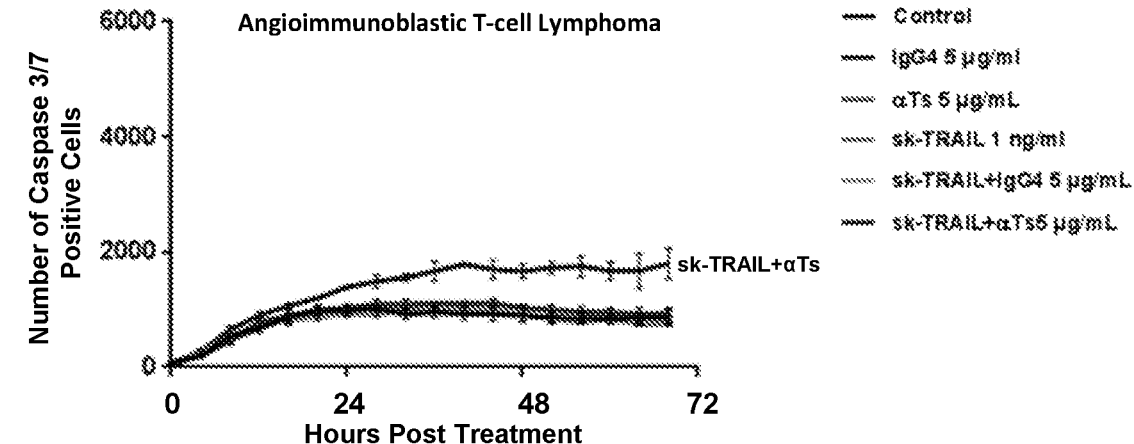

FIG. 27
A
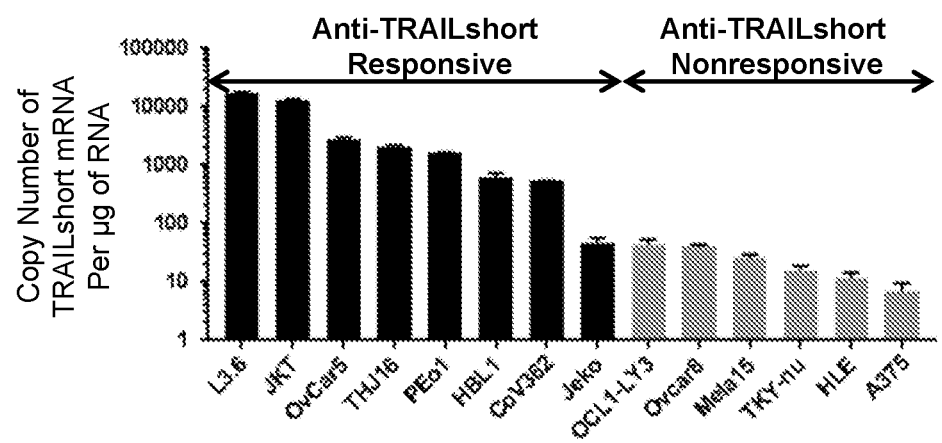
B
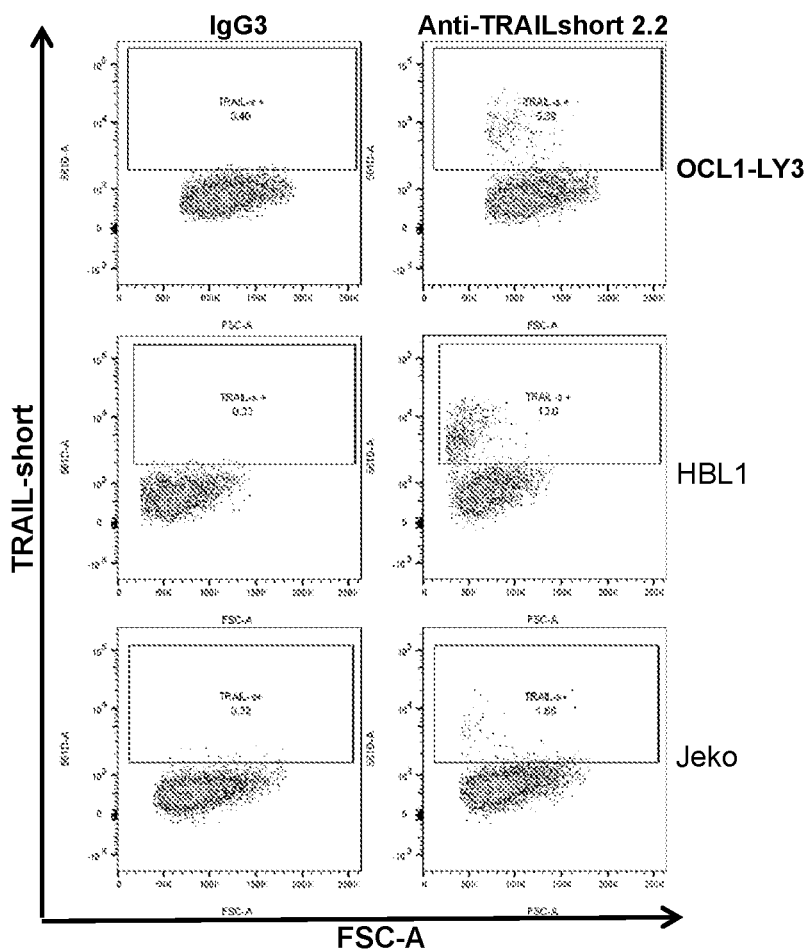

A

B

C

FIG. 29
A
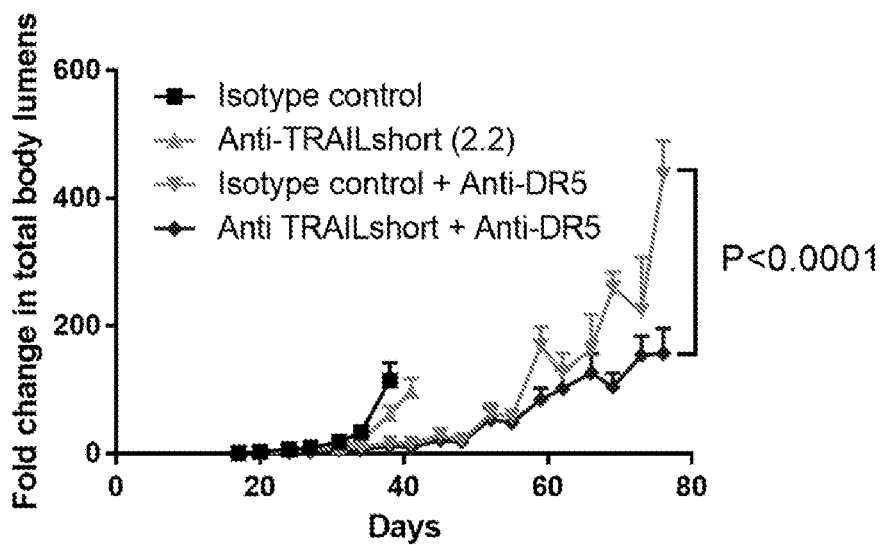
B
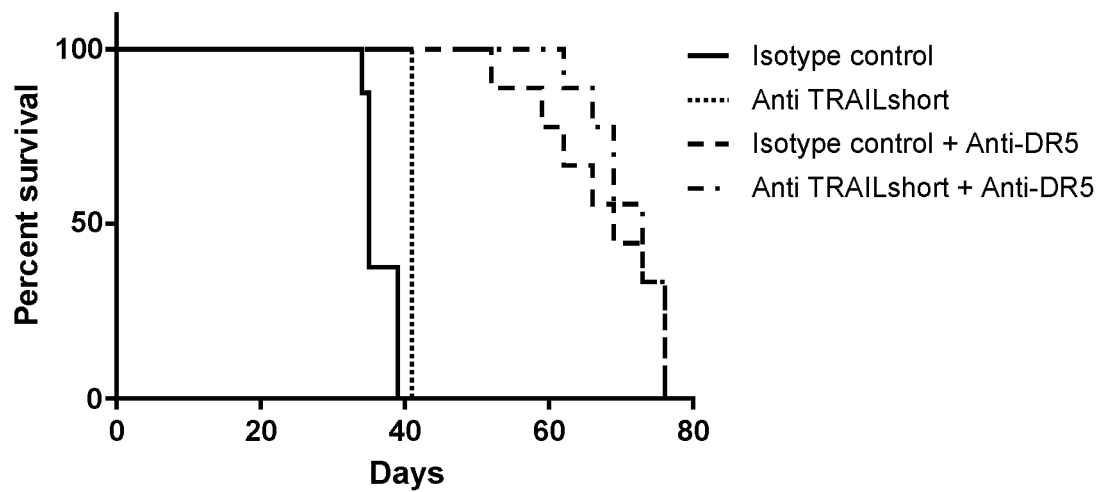

FIG. 30
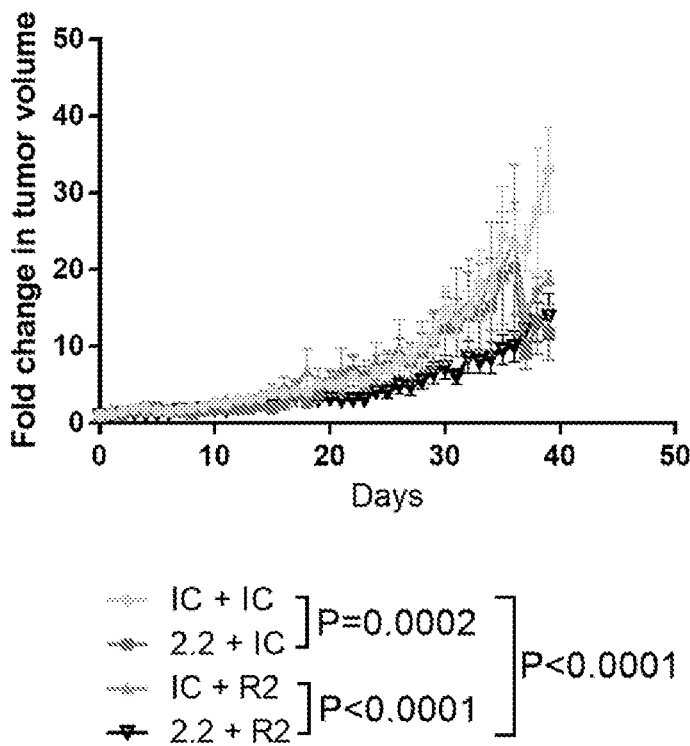
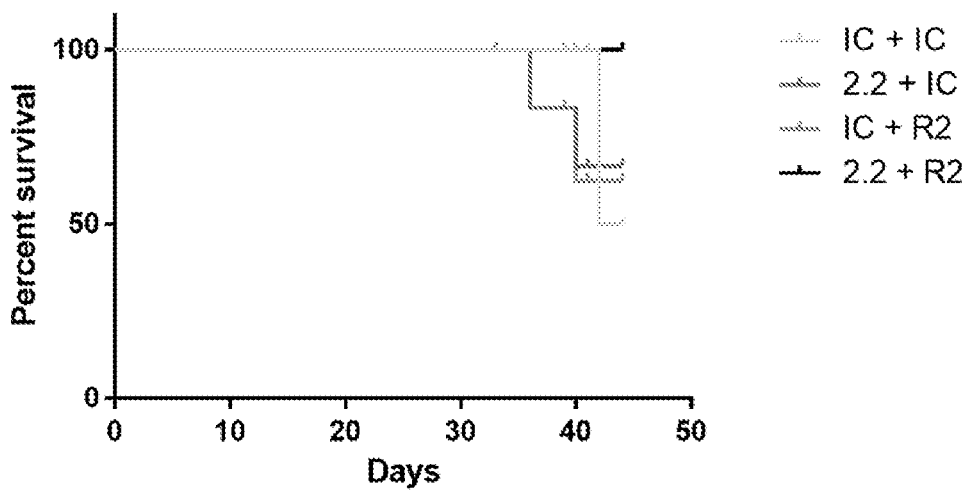

FIG. 31
A
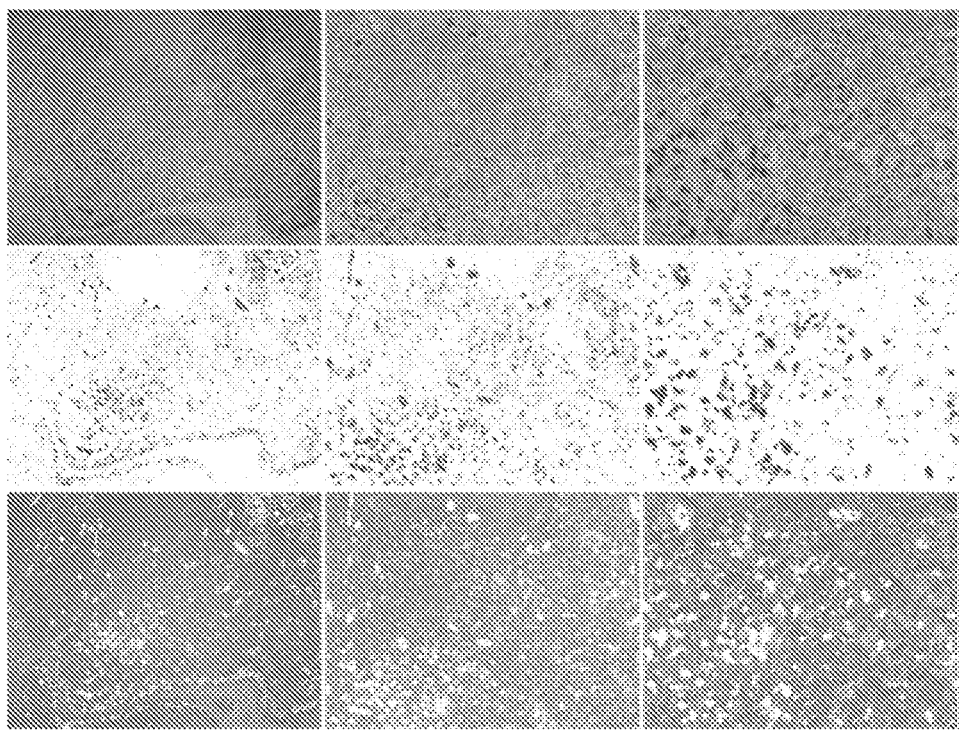
B
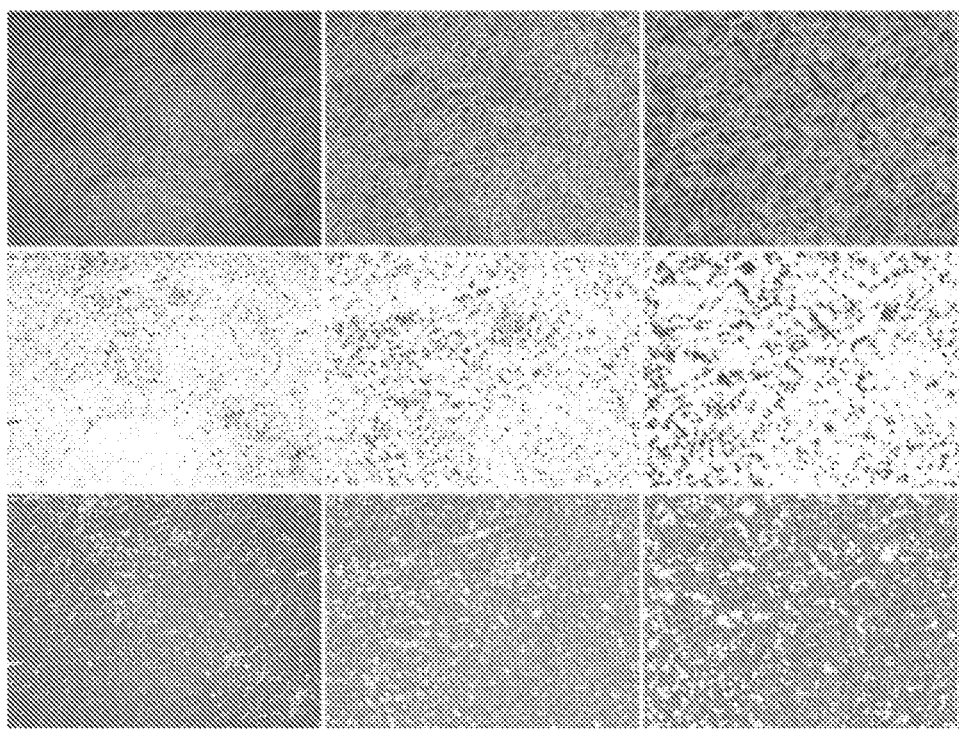

FIG. 31
C
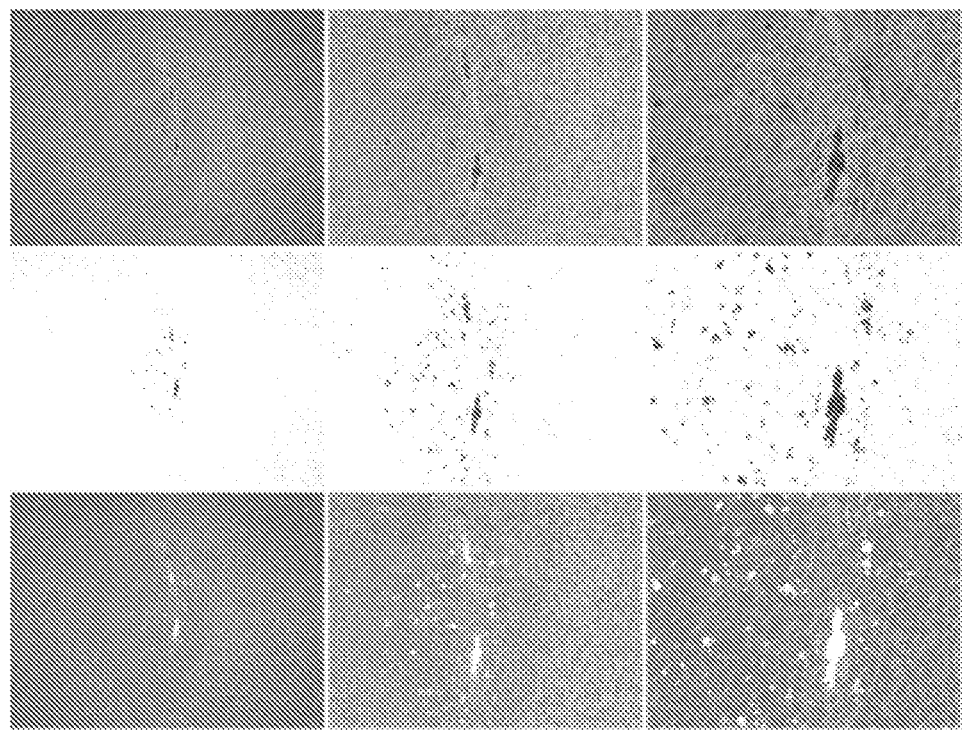
D
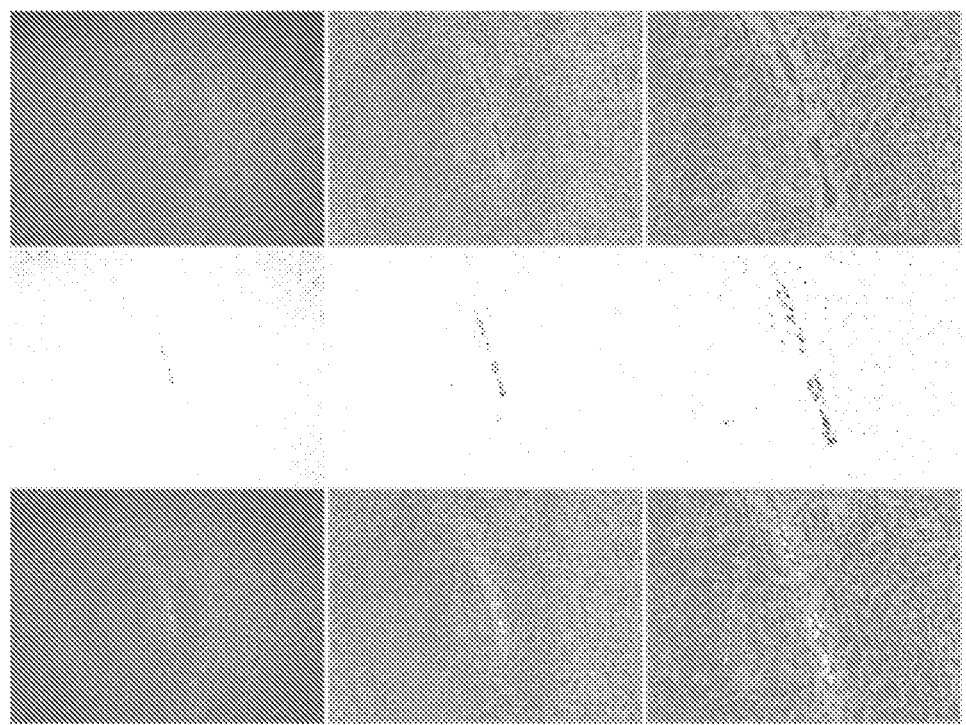

TRAILSHORT ANTIBODY AND METHODS OF USE

CROSS-REFERENCE TO RELATED APPLICATIONS

This application is a National Stage application under 35 U.S.C. § 371 of International Application No. PCT/US2018/017385, having an International Filing Date of Feb. 8, 2018, which claims the benefit of U.S. Patent Application Ser. No. 62/457,614, filed on Feb. 10, 2017, and U.S. Patent Application Ser. No. 62/512,627, filed on May 30, 2017. The disclosures of the prior applications are considered part of (and are incorporated by reference in) the disclosure of this application.

STATEMENT REGARDING FEDERAL FUNDING

This invention was made with government support under AI120698 awarded by the National Institutes of Health. The government has certain rights in the invention.

SEQUENCE LISTING

This application contains a Sequence Listing submitted electronically as an ASCII text file and is hereby incorporated by reference in its entirety. Said ASCII text file, created Mar. 15, 2021, is named 07039-1647US1_Sub_SeqList_ST25.txt and is 52,047 bytes in size.

BACKGROUND

1. Technical Field

This document relates to antibodies against tumor necrosis factor (TNF)-related apoptosis-inducing ligand (TRAIL) short, and more particularly to humanized TRAILshort antibodies that can neutralize TRAILshort. For example, this document provides materials and methods for using one or more humanized TRAILshort antibodies to induce apoptosis.

2. Background Information

TRAIL is an immune-regulatory protein, expressed by immune and other cells, which can kill virally infected or malignant cells through binding to TRAIL receptor 1 (TRAIL-R1) or TRAIL-R2 on target cells. TRAILshort is a splice variant of TRAIL that is capable of blocking TRAIL mediated cell death. TRAIL can bind to one of five cognate receptors, TRAIL-R1, R2, R3, R4, or osteoprotegerin, yet only binding to TRAIL-R1 or R2 induces death through apoptosis of the receptor bearing cell (Wang and El-Deiry, 2003 *Oncogene* 22:8628-8633).

SUMMARY

TRAILshort is a novel splice variant of TRAIL, capable of binding to TRAIL-R1 ("R1") and/or TRAIL-R2 ("R2"). When bound to R1 and/or R2, TRAILshort, prevents full length TRAIL from inducing cell death (Schnepple et al., 2011 *J Biol Chem* 286, 35742-35754).

This document provides antibodies against TRAILshort (e.g., anti-TRAILshort antibodies), and more particularly against humanized TRAILshort antibodies that can neutralize TRAILshort, but do not bind a full length TRAIL. This document also provides materials and methods for making and using antibodies against TRAILshort. For example, one or more humanized TRAILshort antibodies can be used to modulate (e.g., increase or decrease) apoptosis (e.g., via TRAIL mediated cell death, natural killer (NK) cytotoxicity, CD8+ T cell killing, chimeric antigen receptor (CAR) T cell killing, and/or oncolytic virotherapy). In some cases, one or more humanized TRAILshort antibodies can be used to treat cancer (e.g., bladder cancer, breast cancer, cervical cancer, esophageal cancer, head and neck cancer, kidney cancer, hepatocellular carcinoma, lung cancer, colorectal cancer, ovarian carcinoma, melanoma, pancreatic carcinoma, uterine cancer, and hematologic cancer such as B cell malignancies), and/or chronic viral infections (e.g., human immunodeficiency virus (HIV) infections).

As demonstrated herein, the anti-TRAIL effects of TRAILshort can be effectively neutralized using a TRAILshort specific antibody. Neutralization of TRAILshort is effective to induce apoptosis by TRAIL mediated cell death, NK cytotoxicity, CD8+ T cell killing, CAR T cell killing, and/or oncolytic virotherapy.

In general, one aspect of this document features an antibody that binds TRAILshort. The TRAILshort antibody can include a heavy chain variable region (VH) domain including the complementarity-determining regions (CDRs) set forth in SEQ ID NO:1, SEQ ID NO:2, and SEQ ID NO:3; and a light chain variable region (VL) domain comprising the CDRs set forth in SEQ ID NO:14, SEQ ID NO:15, and SEQ ID NO:16. The VH domain can include a sequence having at least 75 percent sequence identity to SEQ ID NO:6. The antibody can be a humanized antibody including a VH domain sequence set forth in SEQ ID NO:6. The heavy chain can include a sequence including SEQ ID NO:9, SEQ ID NO:10, SEQ ID NO:11, SEQ ID NO:12, or SEQ ID NO:13. The VL domain can include a sequence having at least 75 percent sequence identity to SEQ ID NO:20. The antibody can be a humanized antibody including a VL domain sequence set forth in SEQ ID NO:20. The VL domain can include a sequence selected from the group consisting of SEQ ID NO:22, SEQ ID NO:23, SEQ ID NO:24, SEQ ID NO:25, and SEQ ID NO:26. The antibody can be a chimeric antibody (e.g., a humanized antibody). The antibody can be an antigen-binding fragment of an antibody. The antibody can be a monoclonal antibody. The antibody can bind TRAILshort. The antibody can neutralize TRAILshort. In some cases, the antibody can be bispecific (e.g., can include an antigen binding fragment that binds TRAILshort and an antigen binding fragment that binds another antigen such as a cell surface antigen (also referred to as a cell surface marker)).

In another aspect, this document features a method of neutralizing TRAILshort in a mammal. The method includes, or consists essentially of, administering to a mammal an antibody that binds TRAILshort (e.g., an antibody including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16) as described herein. The mammal can be a human. The antibody can be a humanized antibody.

In another aspect, this document features a method of inducing apoptosis in a mammalian cell. The method includes, or consists essentially of, administering to a mammal an antibody that binds TRAILshort (e.g., an antibody including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16) as described herein, under conditions where the antibody is effective to induce apoptosis in the mammalian cell. The mammal can be a human. The antibody can be a humanized antibody. The apoptosis can include TRAIL induced apoptosis.

In another aspect, this document features a method of increasing NK cell cytotoxicity, CD8+ T cell killing, CAR T cell killing, and/or oncolytic virotherapy in a mammalian cell. The method includes, or consists essentially of, administering to a mammal an antibody that binds TRAILshort (e.g., an antibody including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16) as described herein, under conditions where the antibody is effective to increase NK cytotoxicity, CD8+ T cell killing, CAR T cell killing, and/or oncolytic virotherapy in the mammalian cell. The mammal can be a human. The antibody can be a humanized antibody.

In another aspect, this document features a method of treating an infection. The method includes, or consists essentially of, administering to a mammal having an infection an antibody that binds TRAILshort (e.g., an antibody including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16), under conditions where the antibody increases NK cytotoxicity, CD8+ T cell killing, CAR T cell killing, and/or oncolytic virotherapy. The infection can be a chronic infection (e.g., an HIV infection). The mammal can be a human. The antibody can be a humanized antibody. The method also can include administering to the mammal a TRAIL agonist (e.g., recombinant TRAIL, an anti-TRAIL-R1 antibody, an anti-TRAIL-R2 antibody, or a TRAIL oligomer). The method also can include administering to the mammal an antiretroviral therapy (e.g., abacavir, didanosine, emtricitabine, entecavir, lamivudine, stavudine, tenofovir disoproxil fumarate, zalcitabine, zidovudine, delavirdine, efavirenz, etravirine, nevirapine, rilpivirine, adefovir, tenofovir, enfuvirtide, maraviroc, dolutegravir, elvitegravir, raltegravir, bevirimat, amprenavir, fosamprenavir, indinavir, lopinavir, nelfinavir, ritonavir, saquinavir, atazanavir, darunavir, tipranavir, TRIM5alpha, a tat antagonists, or trichosanthin).

In another aspect, this document features a method of treating a cancer. The method includes, or consists essentially of, administering to a mammal having a cancer an antibody that binds TRAILshort (e.g., an antibody including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16) under conditions where the antibody induces apoptosis in a cancer cell from the cancer. The cancer can be, for example, cervical carcinoma, head and neck carcinoma, lymphoma, leukemia, ovarian carcinoma, melanoma, pancreatic carcinoma, or B cell malignancies. The mammal can be a human. The antibody can be a humanized antibody. The method also can include administering to the mammal a TRAIL agonist (e.g., recombinant TRAIL, an anti-TRAIL-R1 antibody, an anti-TRAIL-R2 antibody, or a TRAIL oligomer). The method also can include administering to the mammal a cancer treatment (e.g., chemotherapy agent, radiation therapy, brachytherapy, or surgery). When the cancer treatment is a chemotherapy agent, the chemotherapy agent can be selected from the group consisting of altretamine, busulfan, carboplatin, carmustine, chlorambucil, cisplatin, cyclophosphamide, dacarbazine, lomustine, melphalan, oxalaplatin, temozolomide, thiotepa, 5-fluorouracil (5-FU), 6-mercaptopurine, capecitabine, cytarabine, floxuridine, fludarabine, gemcitabine, hydroxyurea, methotrexate, and pemetrexed, daunorubicin, doxorubicin, epirubicin, idarubicin, actinomycin-D, bleomycin, mitomycin-C, mitoxantrone, topotecan, irinotecan, etoposide, teniposide, mitoxantrone, docetaxel, estramustine, ixabepilone, paclitaxel, vinblastine, vincristine, vinorelbine, prednisone, ethylprednisolone, dexamethasone, L-asparaginase, bortezomib, retinoids, tretinoin, bexarotene, arsenic trioxide, CHOP, R-CHOP, trastuzumab, pertuzumab, ipilimumab, dinutuximab, siltuximab, cetuximab, panitumumab, necitumumab, ramucirumab, bevacizumab, pembrolizumab, nivolumab, atezolizumab, olaratumab, denosumab, blinatumomab, rituximab, ofatumumab, obinutuzumab, daratumumab, alemtuzumab, elotuzumab, gemtuzumab ozogamicin, brentuximab vedotin, trastuzumab, emtansine, apatinib, cabozantinib, alectinib, crizotinib, dasatinib, imatinib, nilotinib, erlotinib, gefitinib, lapatinib, sorafenib, sunitinib, tofacitinib, cobimetinib, trametinib, bortezomib, disulfiram, lactacystin, tamoxifen, obatoclax, navitoclax, gossypol, iniparib, olaparib, perifosine, dabrafenib, vemurafenib, trametinib, abemaciclib, palbociclib, ribociclib, trilaciclib, fulvestrant, temsirolimus, everolimus, vemurafenib, trametinib, dabrafenib, or vintafolide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 11 contains schematic diagrams showing A) how TRAILshort occupies the TRAIL receptor 1 and/or 2 on a target cell thus preventing TRAIL mediated cell death; and B) how a TRAILshort antibody can bind to and block TRAILshort to allow TRAIL to bind to R1 or R2 and induce apoptosis.

FIG. 12 contains amino acid sequences of heavy chain variable regions (VH) and light chain variable regions (VL) of representative anti-TRAILshort antibodies. A. An amino acid sequence alignment including the murine VH (VH0) sequence (SEQ ID NO:4) aligned with four humanized VH variants: VH1 (SEQ ID NO:5), VH2 (SEQ ID NO:6), VH3 (SEQ ID NO:7), and VH4 (SEQ ID NO:8). The CDRs are underlined. B. An amino acid sequence alignment including the murine VL (VL0) sequence (SEQ ID NO:17) aligned with four humanized VL variants: VL1 (SEQ ID NO:18), VL2 (SEQ ID NO:19), VL3 (SEQ ID NO:20), and VL4 (SEQ ID NO:21). The CDRs are underlined.

FIG. 13 contains amino acid sequences of humanized anti-TRAILshort antibodies. A. Amino acid sequences of humanized heavy chains HC0 (SEQ ID NO:9), HC1 (SEQ ID NO:10), HC2 (SEQ ID NO:11), HC3 (SEQ ID NO:12), and HC4 (SEQ ID NO:13). B. Amino acid sequences of humanized heavy chains LC0 (SEQ ID NO:22), LC1 (SEQ ID NO:23), LC2 (SEQ ID NO:24), LC3 (SEQ ID NO:25), and LC4 (SEQ ID NO:26).

Pancreatic, gastric, and prostate cancer tissues have significantly elevated expression of TRAILshort compared to non-malignant tissues.

Figure 18:
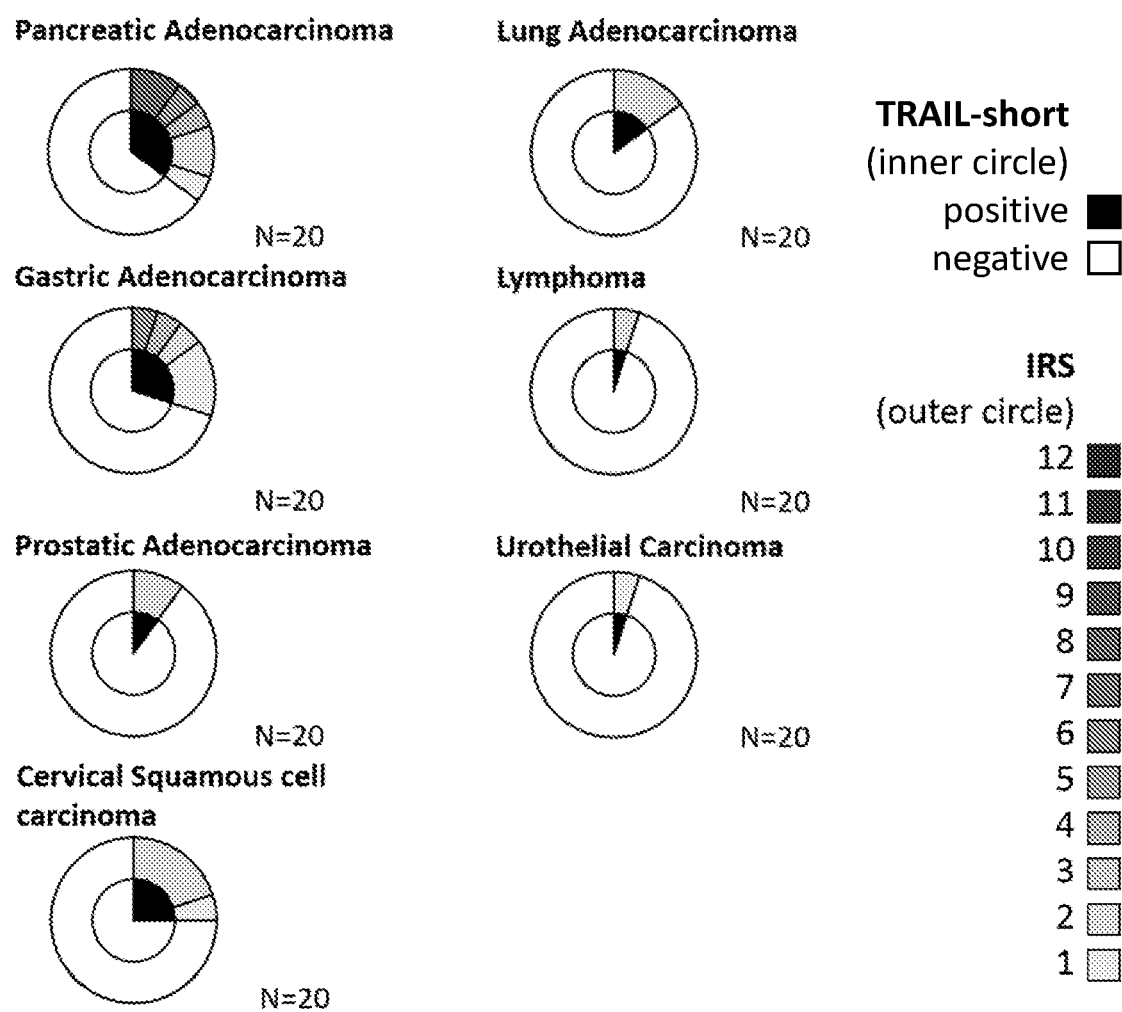

FIG. 18 shows that TRAILshort expression is observed in immunohistochemistry of tissue microarrays. The figure is a summary of 8 Tissue Microarrays (TMA) done using the Anti-TRAIL-short antibody 2.2 at a dilution of 1:400. The inner circle represents the percent of cases in that array positive for TRAIL-short staining. The outer circle represents the Immunoreactive score which is calculated as following: percent of the tissue positive (0-25%=1, 26-50%=2, 51-75%=3 and 76-100%=4) multiplied by the intensity of the staining (negative=0, weak=1,moderate=2, and strong=3).

Figure 19:
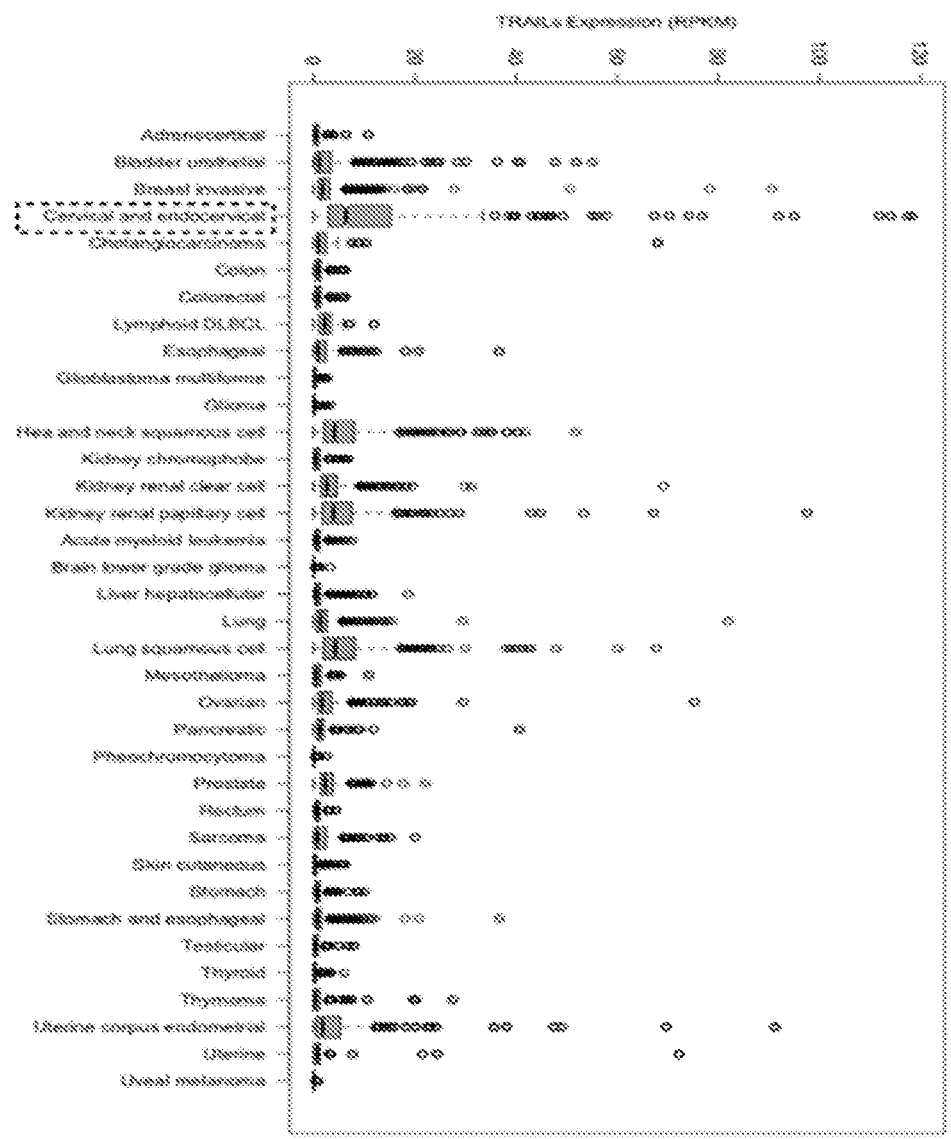

FIG. 19 shows that TRAILshort is found in many human tumors. TRAILshort level, quantified as reads per kilobase million (RPKM), is shown in various human tumors. Data were determined from the Cancer Genome Atlas (TCGA).

Figure 20:
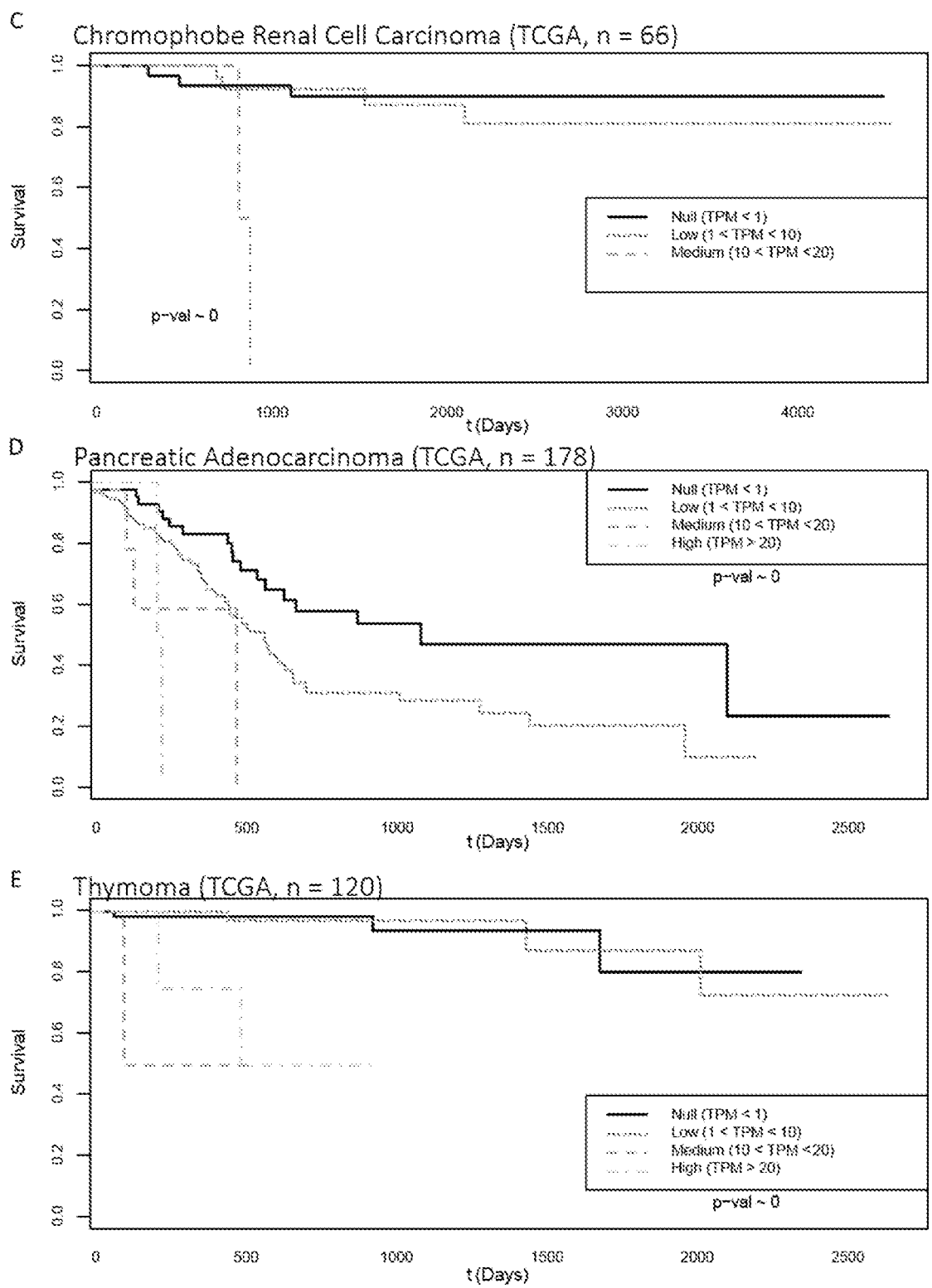

FIG. 20 shows that increasing levels of TRAILshort are associated with worse survival in some human tumors. Survival was assessed by Kaplan Meyer analysis for patients with diffuse large B cell lymphoma (A), colon and rectal adenocarcinoma (B), chromophobe renal cell carcinoma (C), pancreatic adenocarcinoma (D), and thymoma (E). P-value as shown FIG. 21 validates that anti-TRAILshort antibody interacts with TRAILshort antigen. HEK293T cells were transfected with plasmids encoding green fluorescent protein (GFP) (top row), GFP-TRAILshort (middle row), or GFP-TRAIL$_{FL}$ (bottom row). Cells were stained with anti-TRAILshort antibody, secondary goat anti-mouse phycoerythrin (PE) (middle left column), and 4',6-diamidino-2-phenylindole (DAPI) (middle right column). Cells were analyzed by confocal microscopy for PE label (red; leftmost column), GFP (green; middle left column), and DAPI stained nuclei (blue; middle right column). Composite images of all three colors superimposed is also shown (merge; rightmost column).

Figure 22:
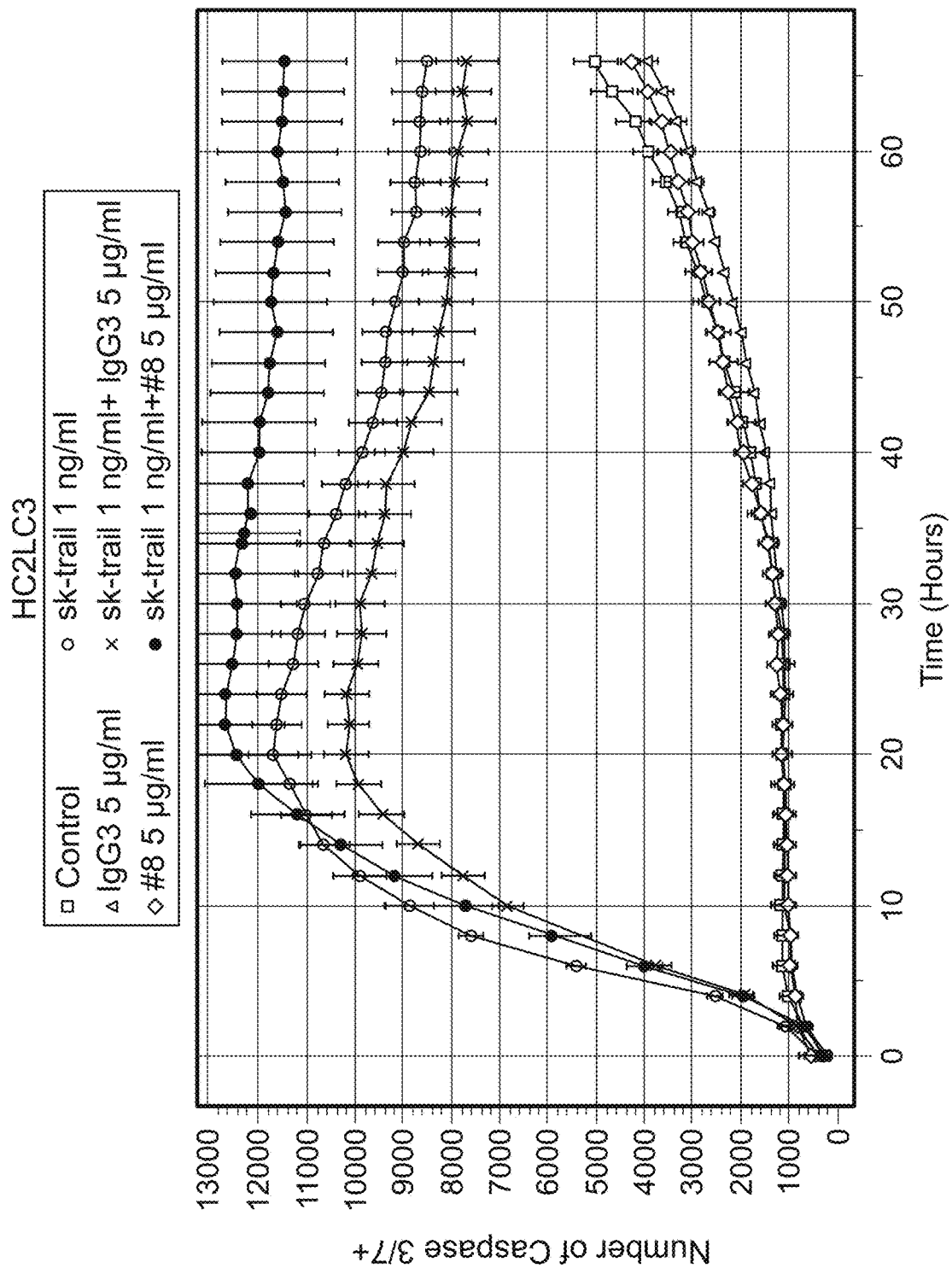

FIG. 22 shows that anti-TRAILshort antibody clone HC2LC3 showed affinity of 3.8 pM, and significant synergistic killing in the presence of sk-TRAIL (1 ng/ml).

Figure 23A:
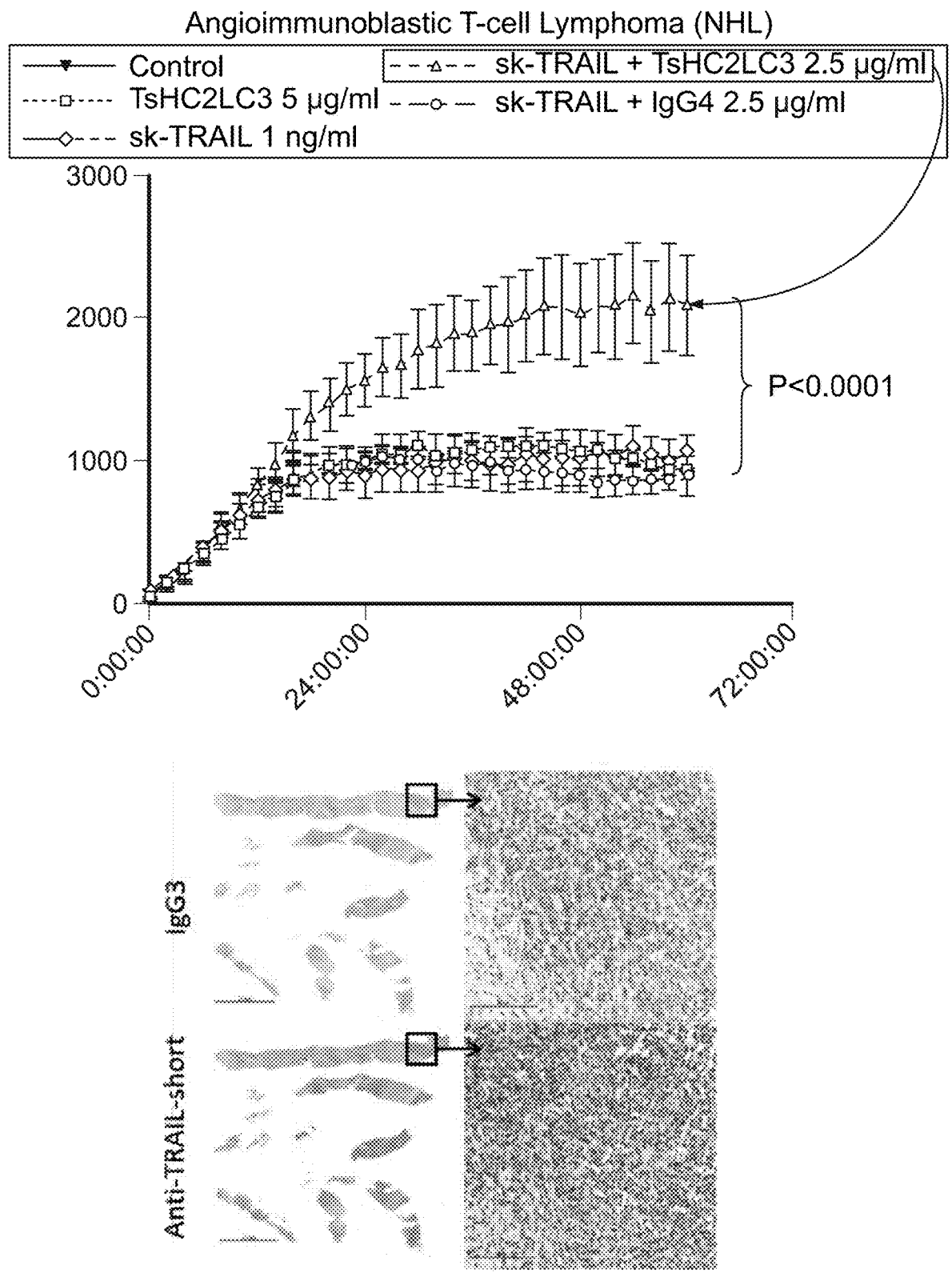
Figure 23C:
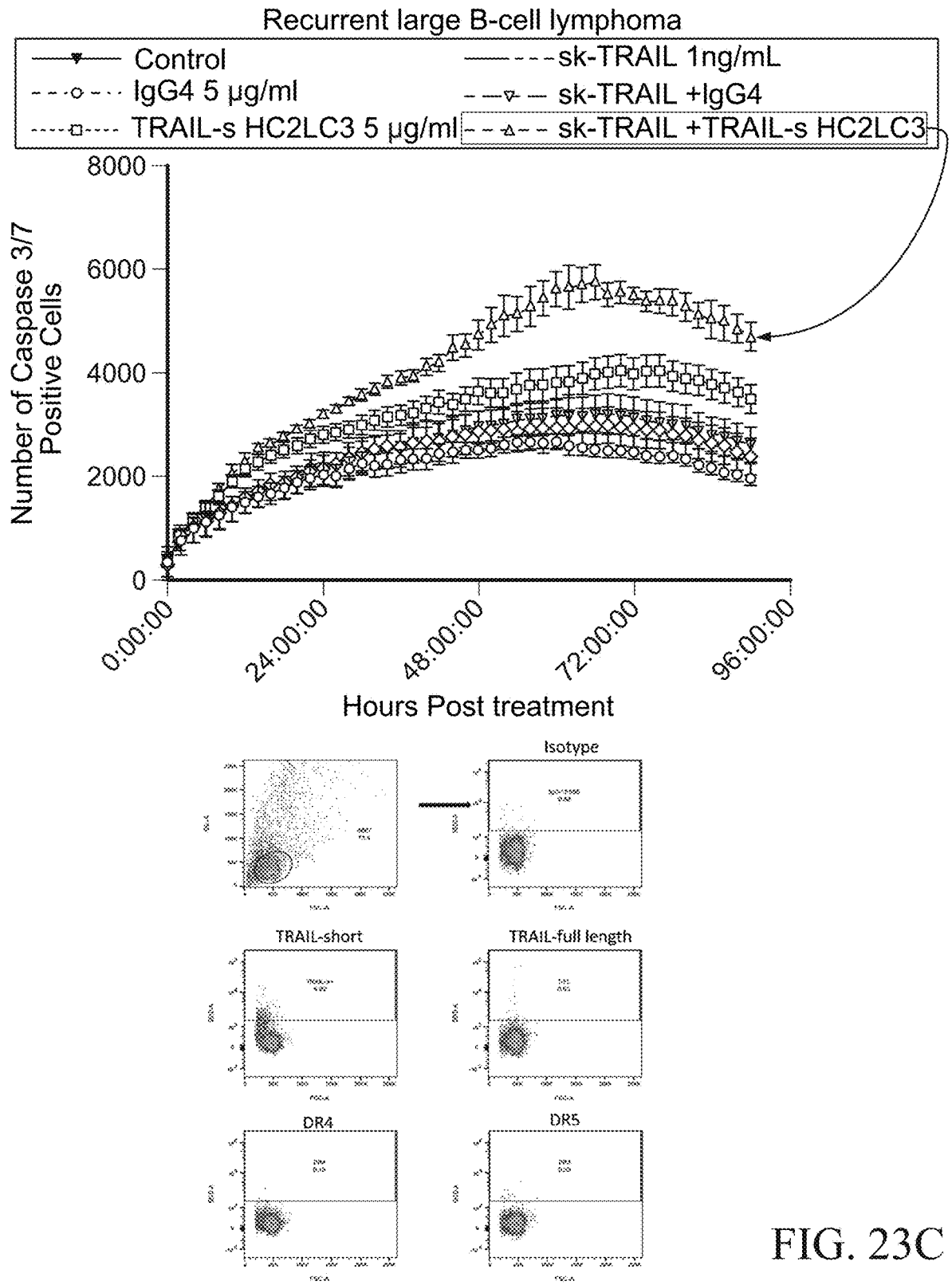
Figure 23D:
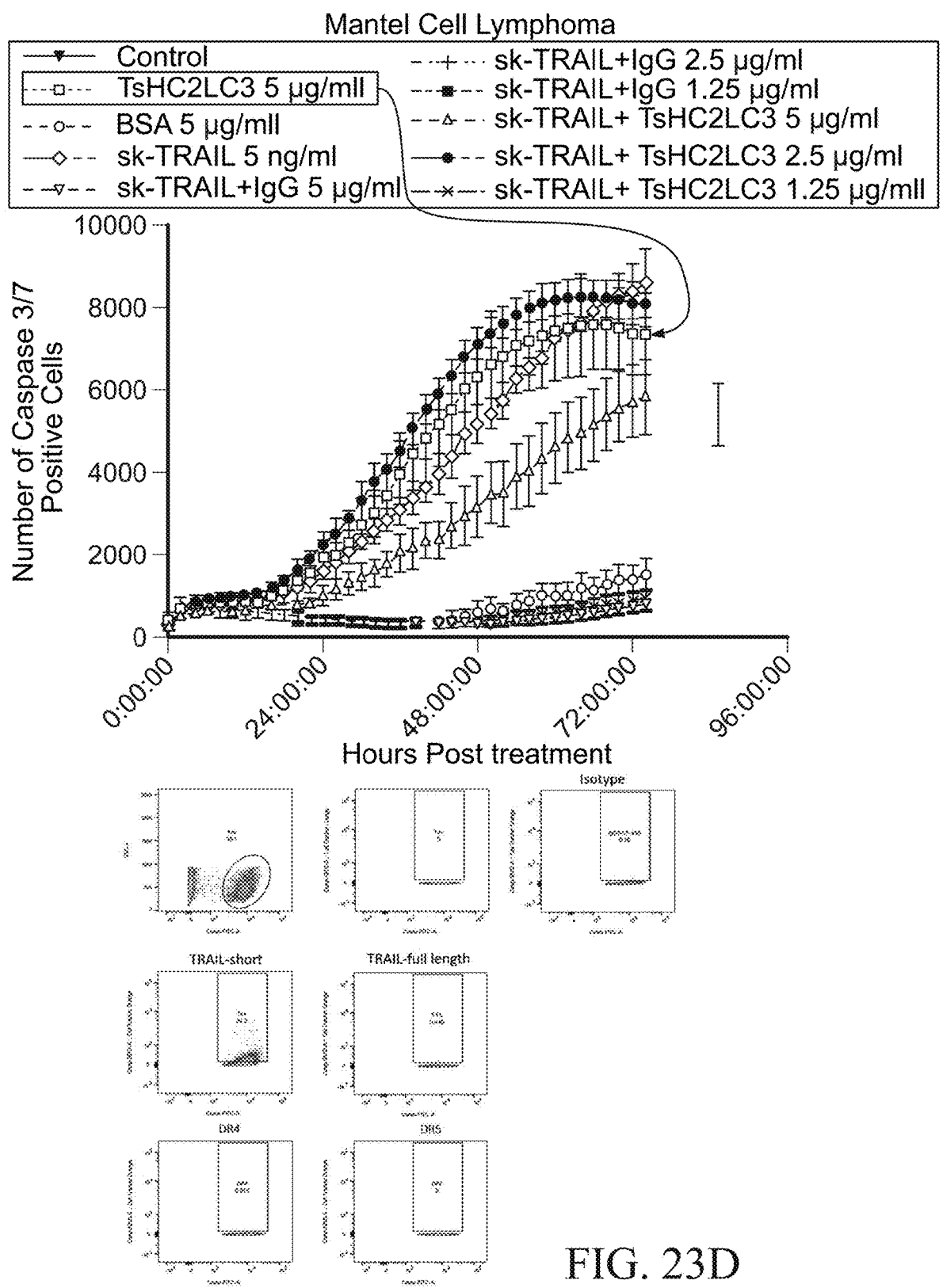

FIG. 23 shows that some patient-derived cells were responsive to anti-TRAILshort antibody plus sk-TRAIL. Cells from the spleens of patients undergoing splenectomy for suspected hematologic malignancy were freshly isolated and treated with nothing (control), superkiller TRAIL (sk-TRAIL, an oligomerised TRAIL agonist), humanized anti-TRAILshort antibody (clone HC2LC3), or Isotype control antibody (IgG4) at the indicated concentrations (and alone or in combination as indicated). Cell death over time was monitored using the Incucyte live cell imaging platform by analyzing active caspase 3/7 activity over time. A) Result from a patient with angioimunoblastic T cell lymphoma (the bottom panel shows IHC for TRAILshort of a different case with the same diagnosis and shows significant expression of TRAILshort). B) Result from a patient with Hodgkins lymphoma (the bottom panel shows IHC for TRAILshort of a different case with the same diagnosis and shows minimal expression of TRAILshort). C) Result from a patient with Recurrent B cell lymphoma (bottom panel showing flow cytometry for TRAILshort, TRAIL, DR4, and DR5 of the same cells). D) Result from a patient with Mantle cell lymphoma (bottom panel showing flow cytometry for TRAILshort, TRAIL, DR4, and DR5 of the same cells). E) Result from a patient with Non Hodgkin Lymphoma B cell lineage/Cyclin D positive.

Figure 24:
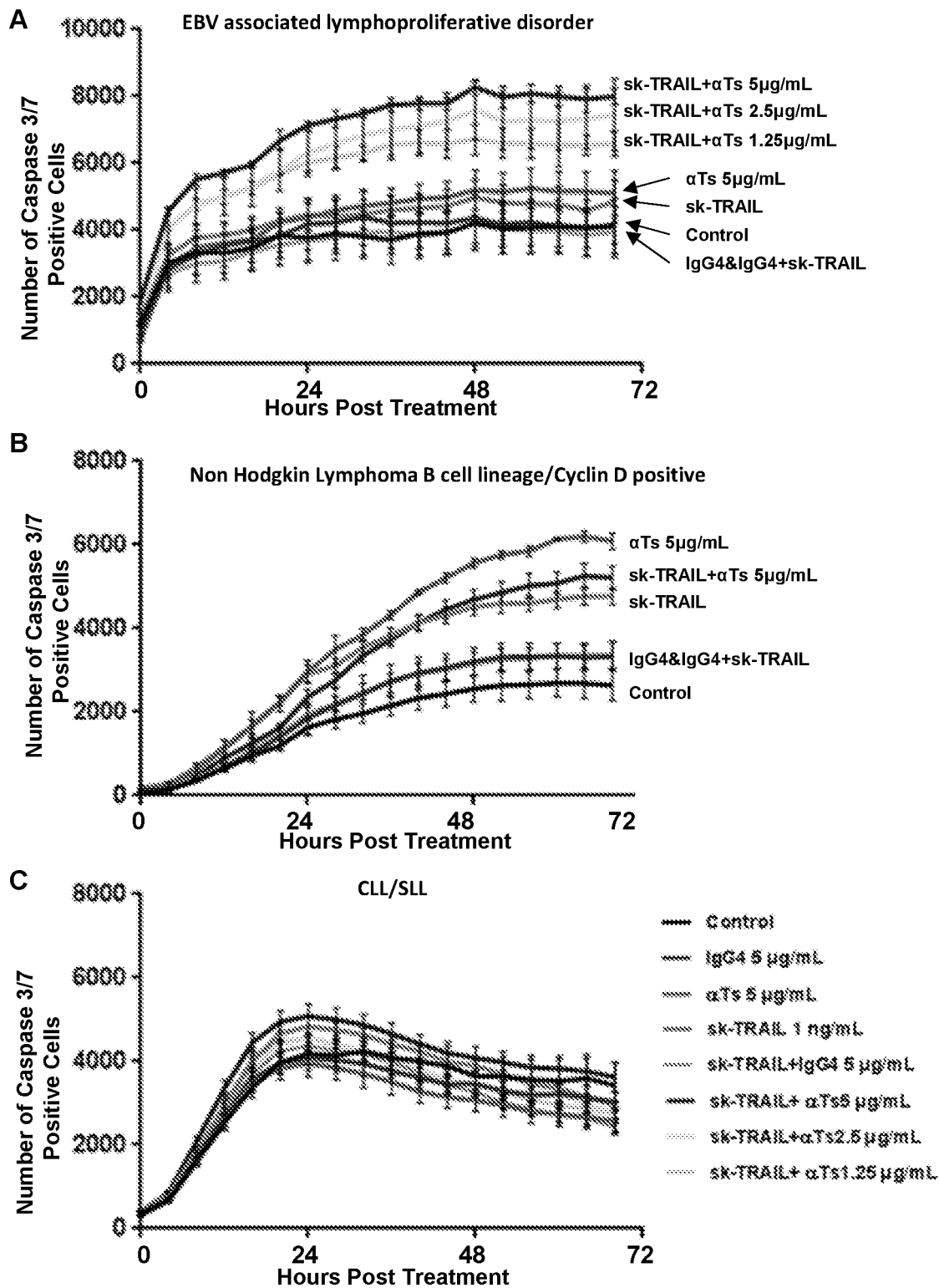

FIG. 24 contains graphs showing the effect of anti-TRAILshort antibody on sk-TRAIL cytotoxicity in different human, patient-derived cancer cell lines. Cells from patient spleens were received fresh in RPMI and tested for sensitivity to cytotoxicity in the presence of sk-TRAIL at a dose of 1 ng/mL in the presence or absence of increasing doses of anti-TRAIL-short clone HC2LC3 (1.25, 2.5, or 5 µg) controls were treated with human IgG4 at the same doses. Cell death was monitored every 2 hours by the number of cells positive for cleaved Caspase 3/7 over 72 hours. The type of cancer shown in panels A-I is as labeled.

Figure 25:
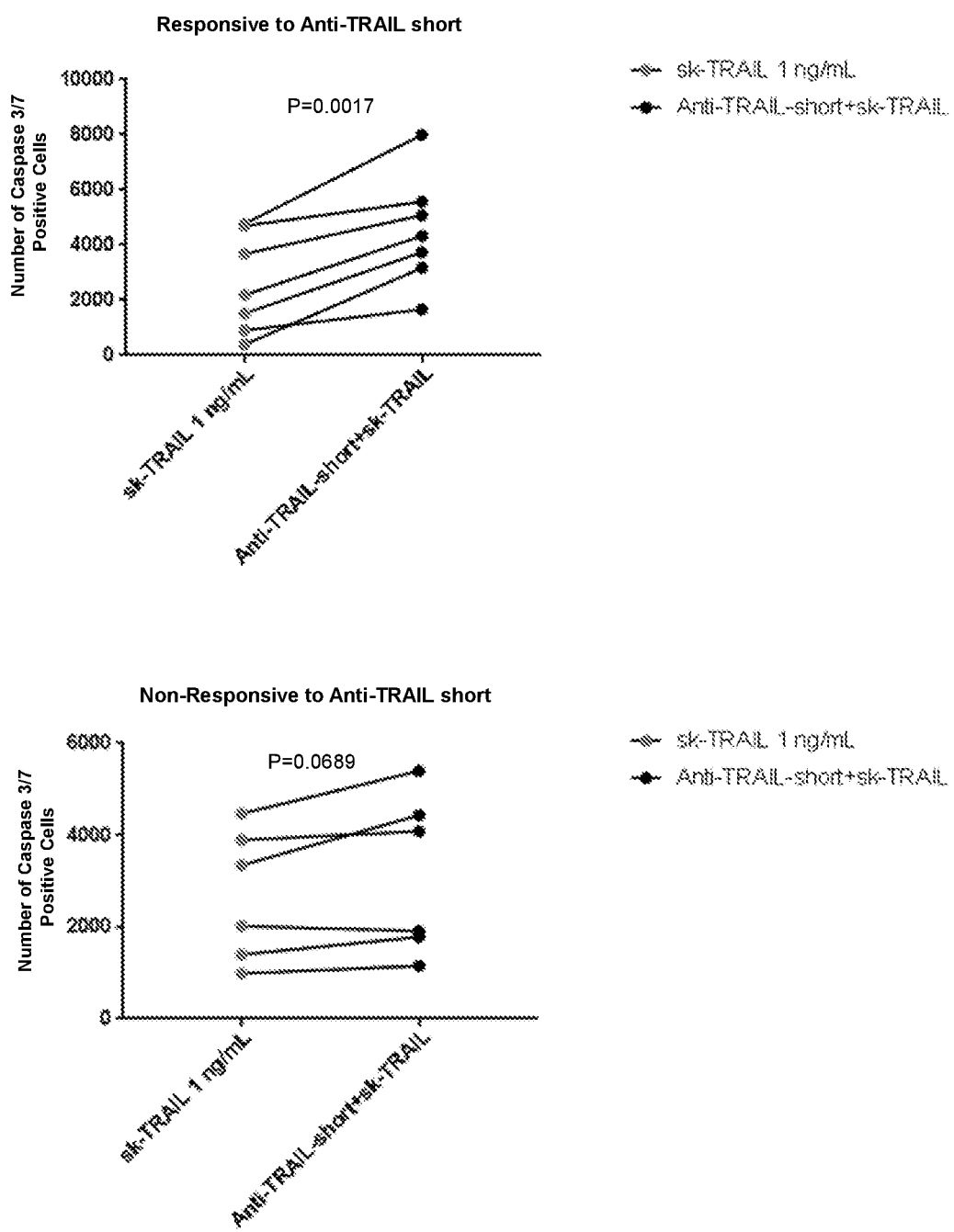

FIG. 25 shows responsiveness to anti-TRAILshort plus sk-TRAIL greater than that of sk-TRAIL alone in a number of human, patient-derived cancer cell lines. Number of dead cells at 48 hours post treatment of sk-TRAIL at a dose of 1 ng/mL alone or sk-TRAIL (same dose) plus anti-TRAIL short clone HC2LC3 at a dose of 5 µg/mL is shown. Responsiveness was defined as a statistically significant increase in the number of dead cells following the addition of the anti-TRAIL short antibody. Statistics for the pair t test is shown.

Figure 26:
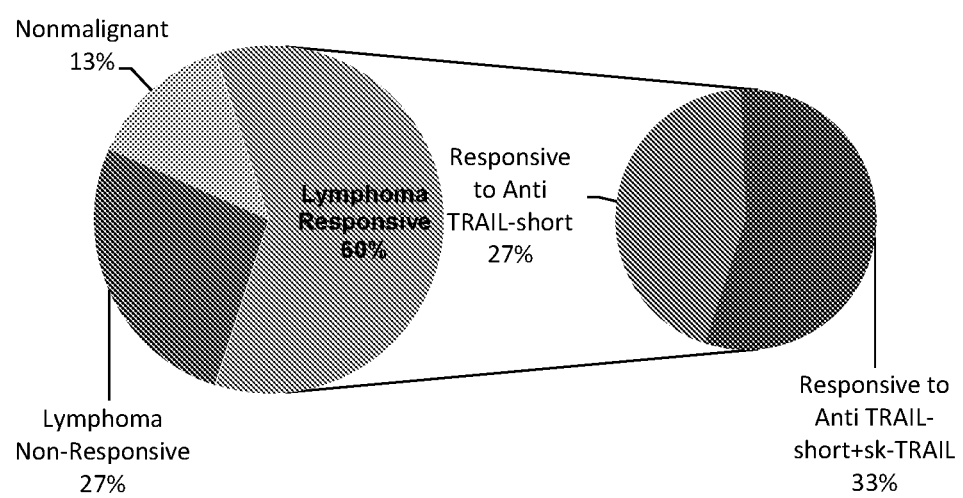

FIG. 26 shows overview results for responsiveness of human, patient-derived cell lines to anti-TRAILshort both alone and in combination with sk-TRAIL. Responsiveness was defined as a statistically significant increase in the number of dead cells over treatment with sk-TRAIL alone.

FIG. 27 shows increased TRAILshort expression in cell lines responsive to anti-TRAILshort. A) Quantification of copy number of TRAILshort mRNA using Real time qPCR in various responsive and non-responsive cell lines. B) Percent of TRAILshort positivity measured by staining of 3 cell lines using anti-TRAIL-short 2.2 conjugated to CF555 or isotype by flow cytometry.

Figure 28:
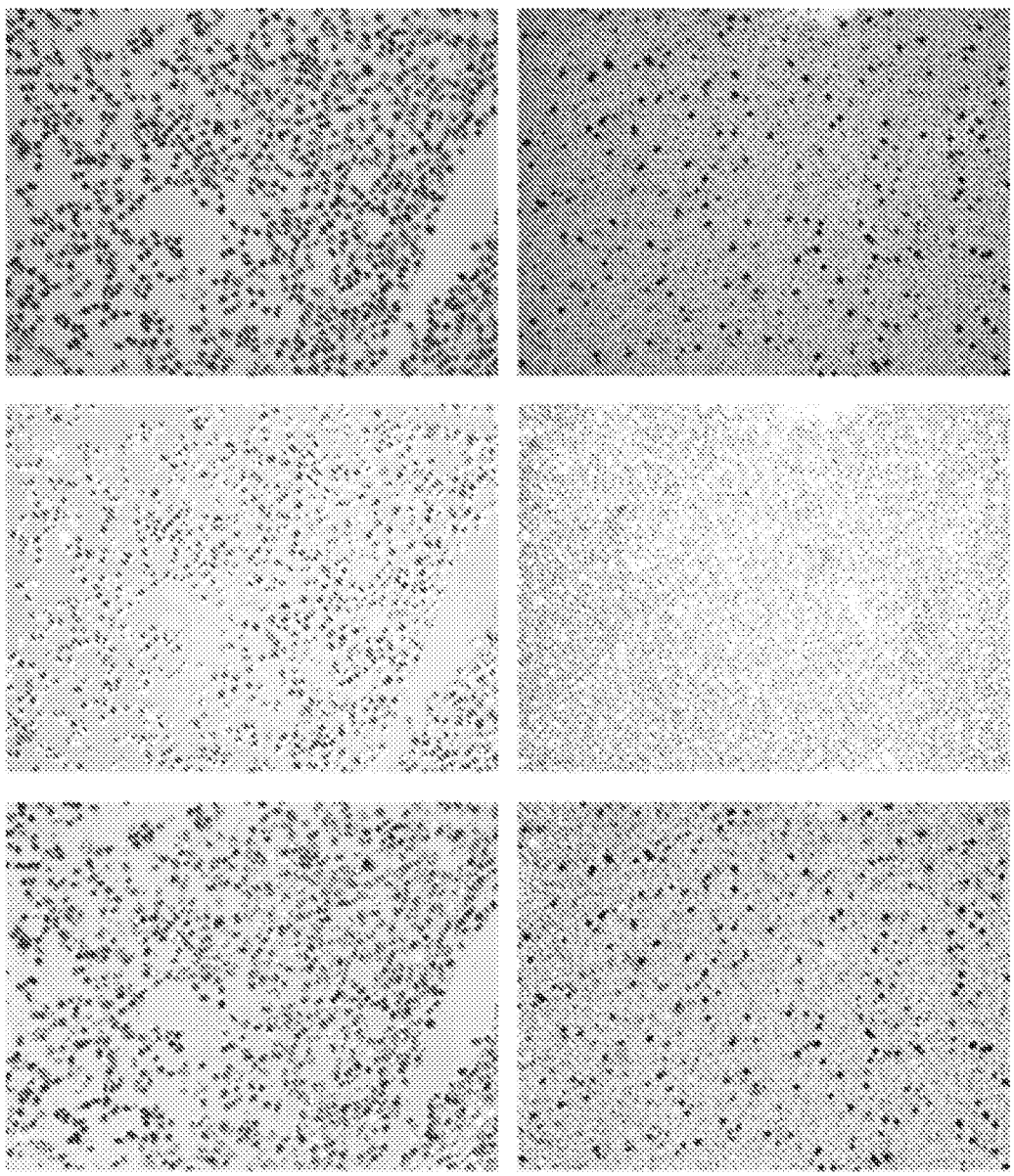
Figure 28:
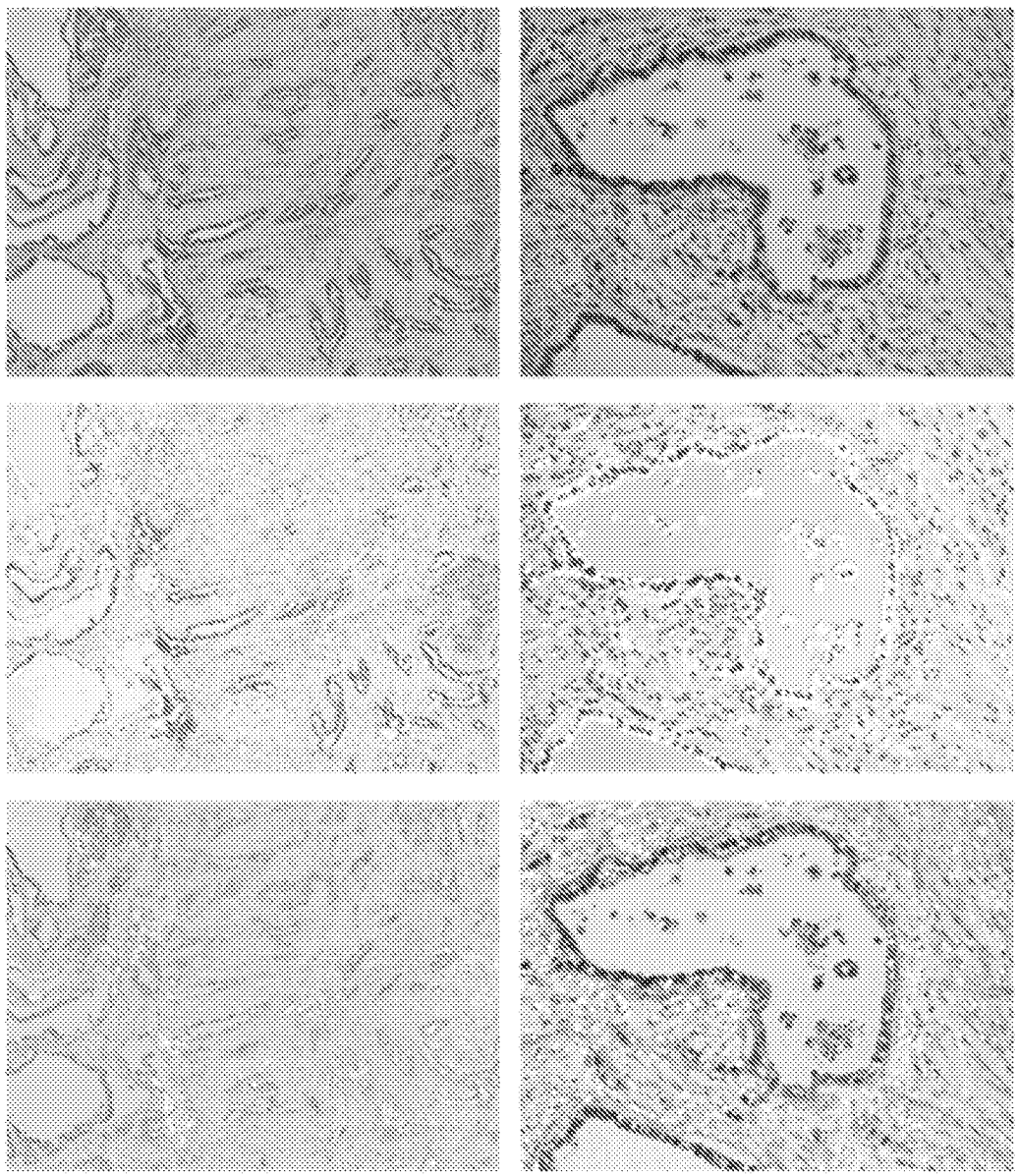
Figure 28:
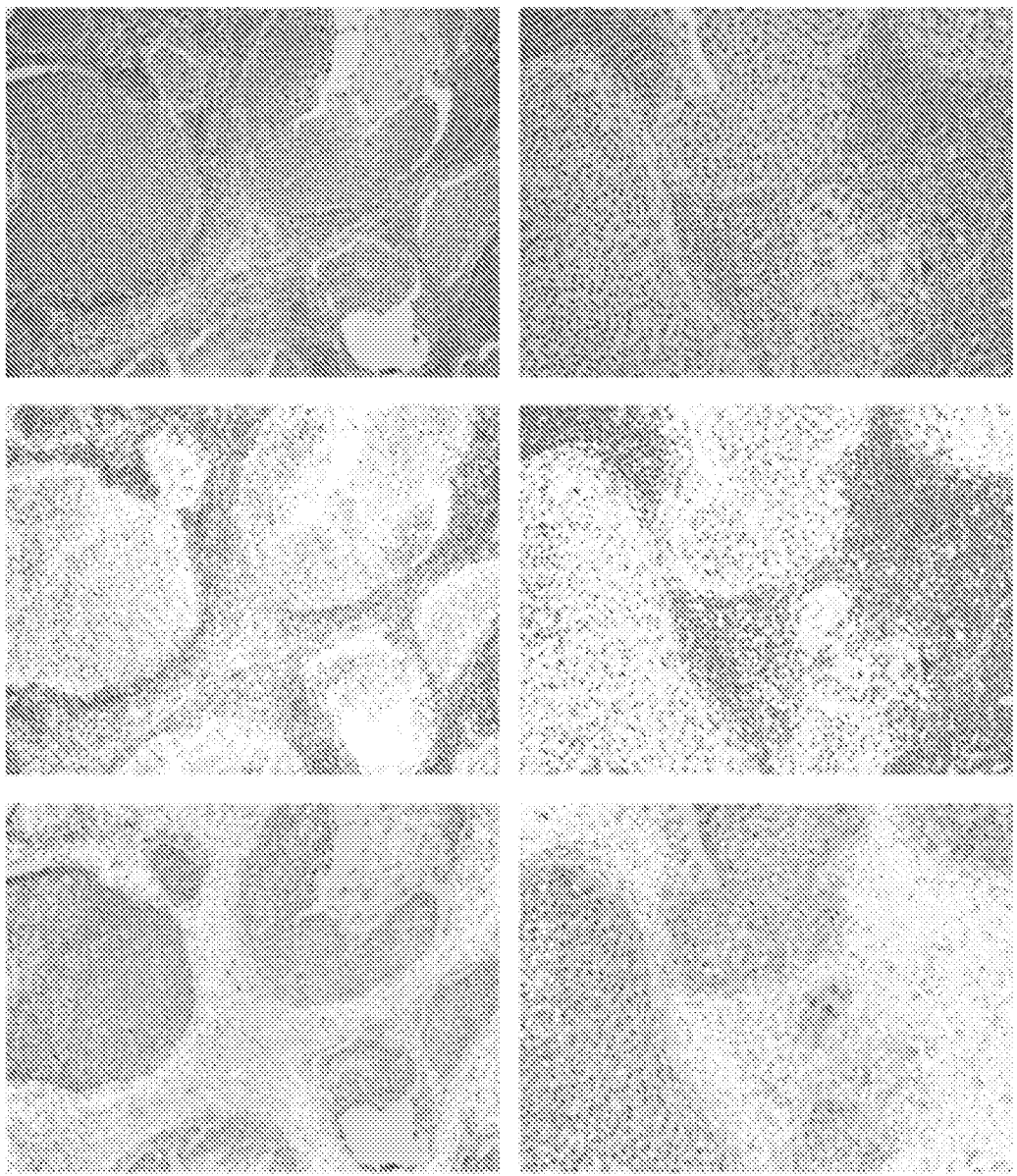

FIG. 28 shows TRAILshort expression in 293T cells and tumor tissues from patients. Shown are immunohistochemistry slides stained for TRAILshort using anti-TRAILshort antibody at a dilution of 1:400. A) The left column shows 293T cells transfected with EGFP (20× magnification) and the right column 293T cells transfected with TRAILshort EGFP (20× magnification) and stained with antibody specific for TRAILshort. Top row are composite images, middle row are components of images stained blue, and bottom row are components of images stained for TRAILshort. B) Pancreatic adenocarcinoma patient tissue at 20x (left) and 40x (right) magnification. Top row are composite images, middle row are components of images stained, and bottom row are components of images stained for TRAILshort. C) Squamous cell carcinoma tonsils patient tissue at 20x (left) and 40x (right) magnification. Top row are composite images, middle row are components of images stained, and bottom row are components of images stained for TRAILshort.

FIG. 29 shows that NSG mice implanted with human Jurkat T cell lymphoma cells are effectively treated with the combination of anti-DR5 plus anti-TRAILshort antibody. Established tumors were treated every 2 weeks with 10 mg/kg every 14 days of either (i) isotype control for TRAILshort and isotype for DR5 antibodies (named Isotype), (ii) anti-TRAILshort antibody clone 2.2 plus an isotype control for anti-DR5 (named Anti-TRAILshort), (iii) an isotype control for anti-TRAILshort antibody plus anti-DR5 antibody (named Isotype control plus Anti-DR5), or (iv) anti-TRAILshort (2.2) plus anti-DR5 as indicated. A) Over time, mice were analyzed for luciferase expression by whole body imaging. B) Survival as assessed by Kaplan Meyer analysis.

FIG. 30 shows that anti-TRAILshort antibody plus isotype control or anti-TRAILshort antibody plus anti-DR5 antibody results in suppressed tumor growth in a mouse xenograft model of human cancer. NSG mice were implanted subcutaneously with the human diffuse Large B cell lymphoma (HBL-1) cell line and tumor size measured daily. When the tumors reached a size of greater or equal to 100 cubic mm, mice received the indicated treatments by weekly IP injections with 10 mg/kg every 14 days of either (i) isotype controls for TRAILshort and for DR5 antibodies (IC+IC), (ii) anti-TRAILshort antibody clone 2.2 plus an Isotype control for anti-DR5 (2.2+IC), (iii) an isotype control for anti-TRAILshort antibody plus anti-DR5 antibody (IC+DR5), or (iv) anti-TRAILshort (2.2) plus anti-DR5 antibody as indicated (2.2+DR5). A) Over time, mice were analyzed for tumor size and fold change calculated from baseline. B) Survival as assessed by Kaplan Meyer analysis.

FIG. 31 shows that TRAILshort can be detected in tissues by in situ hybridization (ISH). Simian immunodeficiency virus (SIV) infected macaque tissues were stained either with TRAIL full length specific probes or TRAILshort specific probes and visualized at the following magnifications. In A-D left column is 10× magnification, middle column is 20× magnification, and right column is 40× magnification. In A-D the top row are composite images, the middle row are components of those composite images (stained for TRAIL in (A) and (C) and stained for TRAILshort in (B) and (D)), and the bottom row are components of those composite images. A) SIV infected macaque axillary lymph node tissue stained with TRAIL specific probe. B) SIV infected macaque axillary lymph node tissue stained with TRAILshort specific probe. C) SIV infected macaque spleen tissue stained with TRAIL specific probe. D) SIV infected macaque spleen tissue stained with TRAILshort specific probe.

DETAILED DESCRIPTION

This document provides TRAILshort antibodies (e.g., humanized TRAILshort antibodies) that can neutralize TRAILshort, as well as materials and methods for making and using TRAILshort antibodies. In some cases, one or more TRAILshort antibodies can be used to treat diseases (e.g., cancers and/or liver conditions) and/or infections (e.g., chronic infections). For example, one or more TRAIL short antibodies can be administered to a mammal having disease and/or an infection under conditions where the number of diseased cells (e.g., cancer cells) and/or infected cells is reduced. In some cases, one or more TRAILshort antibodies can be used to modulate (e.g., increase or decrease) apoptosis (e.g., via TRAIL mediated cell death, NK cytotoxicity, CD8+ T cell killing, CAR T cell killing, and/or oncolytic virotherapy). For example, one or more TRAILshort antibodies can be administered to a mammal having diseased cells (e.g., cancer cells) and/or infected cells (e.g., virally infected cells) under conditions where apoptosis is induced in one or more of the diseased cells (e.g., cancer cells) and/or one or more of the infected cells. This document also provides nucleic acids encoding a TRAILshort antibody described herein as well as constructs for expressing nucleic acids encoding a TRAILshort antibody described herein.

When treating a disease as described herein, the disease can be, for example, a cancer (e.g., carcinoma, sarcoma, lymphoma, leukemia, germ cell tumor, blastoma, and metastasis) or a liver condition. Examples of cancers that can be treated as described herein include, without limitation, ovarian carcinoma, melanoma, pancreatic carcinoma, hematologic malignancies (e.g., T cell malignancies and B cell malignancies), bladder cancer, lung cancer (e.g., non-small-cell lung cancer, squamous non-small-cell lung cancer, and non-squamous non-small-cell lung cancer), colorectal cancer, melanoma, breast cancer (e.g., hormone receptor-positive breast cancer, HER2-positive breast cancer, and triple-negative breast cancer), cervical cancer, esophageal cancer, head and neck cancer, kidney cancer (e.g., renal papillary cell cancer, kidney clear cell cancer, renal transitional cell carcinoma, and chromophobe renal cell carcinoma), hepatocellular carcinoma, myeloma, and uterine cancer.

When treating an infection as described herein, the infection can be, for example, a chronic infection and/or a viral infection. Examples of infections that can be treated as described herein include, without limitation, HIV, SIV, endogenous retrovirus, anellovirus, circovirus, human herpesvirus, varicella zoster virus, cytomegalovirus, Epstein-Barr virus, polyomavirus, adeno-associated virus, herpes simplex virus, adenovirus, hepatitis B virus, hepatitis C virus, hepatitis D virus, GB virus C, papilloma virus, human T cell leukemia virus, xenotropic murine leukemia virus-related virus, polyomavirus, rubella virus, parvovirus, measles virus, and coxsackie virus infections. In some cases, the infections treated as described herein can be an HIV infection.

When treating unwanted apoptosis as described herein, the unwanted apoptosis can be, for example, associated with any appropriate disease and/or condition. Examples of diseases and/or conditions associated with unwanted apoptosis that can be treated as described herein include, without limitation, myocardial infarction, ischemia reperfusion injury, neurodegenerative diseases (e.g., multiple sclerosis, amyotrophic lateral sclerosis, Parkinson's disease, Alzheimer's disease, and Huntington's disease), liver injury (e.g., following alcohol consumption, following drug (e.g., acetaminophen) ingestion, and nonalcoholic steatohepatitis).

Any type of mammal having a disease and/or an infection or at risk for developing a disease and/or an infection can be treated as described herein. For example, humans and other primates such as monkeys having a disease and/or an infection can be treated with one or more TRAILshort antibodies. In some cases, dogs, cats, horses, cows, pigs, sheep, rabbits, mice, and rats can be treated with one or more TRAILshort antibodies as described herein.

Any appropriate method can be used to identify a mammal having a disease and/or an infection or at risk for developing a disease (e.g., cancer) and/or an infection. For example, imaging techniques (with or without contrast; e.g., computerized tomography (CT) scanning or magnetic resonance imaging (MRI)), biopsy techniques, bone marrow aspiration, colonoscopy, sigmoidoscopy, digital rectal exam, blood assay, platelet assay, fecal assay, urine assay, endoscopic techniques, ELISA techniques, PCR-based techniques, blotting techniques (e.g., western blot), and histological techniques can be used to identify a mammal (e.g., a human) having a cancer. For example, imaging techniques (with or without contrast; e.g., CT scanning or MRI), biopsy techniques (e.g., liver tissue examination), and blood tests can be used to identify a mammal (e.g., a human) having a liver condition. For example, antibody techniques, viral antigen detection tests, culturing techniques, ELISA techniques, PCR-based techniques (e.g., viral load test), blotting techniques (e.g., western blot), hybridization techniques (e.g., ISH), and histological techniques (e.g., immunohistochemistry (IHC)) can be used to identify a mammal (e.g., a human) having an infection.

In some cases, one or more TRAILshort antibodies can be used to identify a mammal as being likely to respond well to TRAIL-based therapies. For example, one or more TRAILshort antibodies can be administered to a mammal having disease and/or an infection to identify the mammal as being likely to respond well to TRAILshort-based therapies. In some cases, a mammal having a disease and/or an infection or being at risk for developing a disease and/or an infection can be assessed for the presence or absence of TRAILshort and/or TRAIL. For example, the presence, absence, or level of TRAILshort and/or TRAIL in a sample obtained from a human having a disease and/or infection can be used to determine whether or not the human is likely to respond to TRAIL-based therapies. Any appropriate sample can be assessed for the presence of TRAILshort and/or TRAIL. For example, biological samples such as tissue samples and fluid samples (e.g., blood, serum, plasma, or urine) can be obtained from a mammal and assessed for the presence, absence, or level of TRAILshort and/or TRAIL. Any appropriate method can be used to detect the detect the presence, absence, or level of TRAILshort and/or TRAIL. For example, antibody techniques, viral antigen detection tests, culturing techniques, ELISA techniques, PCR-based techniques (e.g., viral load test), blotting techniques (e.g., western blot), hybridization techniques (e.g., ISH), and histological techniques (e.g., IHC) can be used to determine the presence, absence, or level of TRAILshort and/or TRAIL in a sample obtained from a mammal. In some cases, TRAILshort antibody described herein (e.g., including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16) can be labelled (e.g., with radionuclides to enable PET or SPECT imaging) and used to determine the presence, absence, or level of TRAILshort and/or TRAIL in a sample obtained from a mammal. A mammal can be identified as being likely to respond to TRAIL-based therapies when a sample obtained from the mammal has detectable levels of TRAILshort and/or TRAIL. In some cases, mammals identified as being likely to respond to TRAIL-based therapies can be treated as described herein. For example, one or more anti-cancer agents that inhibit IL-6, IL-8, and EGF can be administered to a human identified as having a triple negative breast cancer (e.g., a TNBC) to treat the human.

Once identified as having a disease and/or an infection, as being at risk for developing a disease and/or an infection, or as being likely to respond well to TRAIL-based therapies, the mammal can be administered or instructed to self-administer one or more TRAILshort antibodies (e.g., a composition containing one or more TRAILshort antibodies that neutralize TRAILshort). In some cases, a mammal (e.g., a human), can be identified as having TRAILshort. For example, a mammal can be evaluated for the presence or absence of TRAILshort using any appropriate method. For example, techniques to detect levels of TRAILshort include ELISA techniques, PCR-based techniques, blotting techniques (e.g., western blot), hybridization techniques (e.g., ISH), and/or histological techniques (e.g., IHC). The presence or absence of TRAILshort can be used, for example, to determine that a mammal is likely to respond to TRAILshort antibody therapy.

Any appropriate method can be used to administer one or more TRAILshort antibodies to a mammal. For example, one or more TRAILshort antibodies can be administered to a mammal and/or nucleic acids encoding one or more TRAILshort antibodies can be administered to a mammal. In cases where nucleic acids encoding one or more TRAILshort antibodies are administered to a mammal, the nucleic acids can be contained in a vector (e.g., for vector-mediated antibody gene transfer).

TRAILshort antibodies provided herein bind specifically to an epitope on TRAILshort. The term "antibody" as used herein refers to intact antibodies as well as antibody fragments (e.g., antigen-binding fragments) that retain some ability to bind to TRAILshort. In some cases, TRAILshort antibodies provided herein do not bind to full length TRAIL. A TRAILshort antibody can be a monoclonal antibody or a polyclonal antibody. A TRAILshort antibody can be a chimeric (e.g., partially humanized or fully humanized) antibody. A TRAILshort antibody can be a non-immunogenic antibody. In some cases, a TRAILshort antibody can be a neutralizing antibody. As used herein, a TRAILshort "neutralizing" antibody is an antibody that binds to TRAILshort to neutralize the biological effects of TRAILshort. In some cases, a TRAILshort antibody can induce (e.g., increase) apoptosis. For example, a TRAILshort neutralizing antibody binds to TRAILshort, preventing TRAILshort from binding to R1 and/or R2, and thus leaving R1 and R2 available for TRAIL binding and induction of apoptosis. For example, a TRAILshort neutralizing antibody binds to TRAILshort, removing bound TRAILshort from R1 and/or R2, and thus leaving R1 and R2 available for TRAIL binding and induction of apoptosis. In some cases, a TRAILshort antibody can recapitulate TRAILshort function. As used herein, "TRAILshort function" includes the ability to reduce and/or eliminate TRAIL mediated cell death. In some cases, a TRAILshort antibody can inhibit (e.g., decrease) apoptosis. For example, TRAILshort antibodies provided herein can include an extracellular domain of TRAILshort fused to an Fc domain (e.g., an IgG Fc domain). For example, an extracellular domain of TRAILshort fused to an IgG Fc domain can be used to reduce and/or eliminate apoptosis (e.g., unwanted apoptosis).

TRAILshort antibodies provided herein can be prepared using any suitable method (see, e.g., Green et al., Production of Polyclonal Antisera, in *Immunochemical Protocols* (Manson, ed.), pages 1-5 (Humana Press 1992); Coligan et al., Production of Polyclonal Antisera in Rabbits, Rats, Mice and Hamsters, in *Current Protocols In Immunology*, section 2.4.1 (1992); Coligan et al., Unit 9, Current Protocols in Immunology, Wiley Interscience, 1994; Kohler & Milstein, *Nature* 256:495 (1975); Coligan et al., sections 2.5.1 2.6.7; and Harlow et al., *Antibodies: A Laboratory Manual*, page 726 (Cold Spring Harbor Pub. 1988)). For example, a sample containing a TRAILshort can be used as an immunogen to elicit an immune response in an animal such that specific antibodies are produced.

TRAILshort antibodies provided herein can be humanized and/or de-immunized (e.g., made non-immunogenic) using any appropriate method. For example, humanized monoclonal antibodies can be produced by transferring mouse CDRs from heavy and light variable chains of the mouse immunoglobulin into a human variable domain, and then substituting human residues in the framework regions of the murine counterparts. The use of antibody components derived from humanized monoclonal antibodies can obviate potential problems associated with the immunogenicity of murine constant regions when treating humans. General techniques for cloning murine immunoglobulin variable domains are described, for example, by Orlandi et al., *Proc. Nat'l. Acad. Sci. USA* 86:3833 (1989). Techniques for producing humanized monoclonal antibodies are described, for example, by Jones et al., *Nature* 321:522 (1986); Riechmann et al., *Nature* 332:323 (1988); Verhoeyen et al., *Science*

239:1534 (1988); Carter et al., *Proc. Nat'l. Acad. Sci. USA* 89:4285 (1992); and Sandhu, *Crit. Rev. Biotech.* 12:437 (1992); Singer et al., *J. Immunol.* 150:2844 (1993). In some cases, humanization such as super humanization can be used as described elsewhere (Hwang et al., *Methods*, 36:35-42 (2005)). In some cases, SDR grafting (Kashmiri et al., *Methods*, 36:25-34 (2005)), human string content optimization (Lazar et al., *Mol. Immunol.*, 44:1986-1998 (2007)), framework shuffling (Dall' Acqua et al., *Methods*, 36:43-60 (2005); and Damschroder et al., *Mol. Immunol.*, 44:3049-3060 (2007)), and phage display approaches (Rosok et al., *J. Biol. Chem.*, 271:22611-22618 (1996); Radar et al., *Proc. Natl Acad. Sci. USA*, 95:8910-8915 (1998); and Huse et al., *Science*, 246:1275-1281 (1989)) can be used to obtain TRAILshort antibody preparations. In some cases, a TRAILshort antibody can be humanized as described in Examples 3 and 4. A TRAILshort antibody can be antibody Ab866.

A TRAILshort antibody heavy chain can include an immunoglobulin Fc domain (e.g., a humanized immunoglobulin Fc domain). The Fc domain can be from any of isotype (e.g., IgG IgA, IgD, IgE, or IgM). The Fc domain can be from any isotype subclass. For example, when an Fc domain is an IgG isotype, the Fc domain can be an IgG1, IgG2, IgG3, or IgG4 Fc domain.

A TRAILshort antibody (e.g., antibody Ab866) VH domain can include the complementarity-determining regions (CDRs) set forth below:

```
VH CDR1:    GYIFTNNDMN;             (SEQ ID NO: 1)

VH CDR2:    GIDPGDGRTKYNEKFKG;      (SEQ ID NO: 2)
and

VH CDR3:    GRGGYEFGIDY.            (SEQ ID NO: 3)
```

Examples of TRAILshort antibody VH domains including VH CDR1, VH CDR2 and VH CDR3 include, without limitation, the VH domains set forth below:

VH0:
(SEQ ID NO: 4)
QVQLQQSGPELVKPGASVKISCKASGYIFTNNDMNWVKQRPGQGLEWI

GGIDPGDGRTKYNEKFKGKATLTADKFSNTVYMQLSSLTSENSAVYFC

GRGGYEFGIDYWGQGTSVTVSS;

VH1:
(SEQ ID NO: 5)
QVQLVQSGAEVKKPGATVKISCKVSGYIFTNNDMNWVQQAPGKGLEWM

GGIDPGDGRTKYNEKFKGRVTITADESTSTAYMELSSLRSEDTAVYYC

GRGGYEFGIDYWGQGTLVTVSS;

VH2:
(SEQ ID NO: 6)
QVQLVQSGAEVKKPGASVKVSCKASGYIFTNNDMNWVRQAPGQGLEWM

GGIDPGDGRTKYNEKFKGRVTMTRDTSTNTVYMELSSLTSEDTAVYFC

GRGGYEFGIDYWGQGTTVTVSS;

VH3:
(SEQ ID NO: 7)
QVQLVQSGAEVKKPGSSVKVSCKSSGYIFTNNDMNWVRQAPGQGLDWM

GGIDPGDGRTKYNEKFKGRVTISADIFSNTAYMELNSLTSEDTAVYFC

GRGGYEFGIDYWGQGTTVTVSS;
and

VH4:
(SEQ ID NO: 8)
QVQLVESGAEVKKPGASVKVSCKVSGYIFTNNDMNWVRQAPGEGLEWM

GGIDPGDGRTKYNEKFKGRVTMTEDTSTDTAYMELSSLRSEDTAVYYC

GRGGYEFGIDYWGQGTTVTVSS.

In some cases, a TRAILshort antibody VH domain can have an amino acid sequence that is at least 75 percent (e.g., at least 78%, at least 79%, at least 80%, at least 81%, at least 82%, at least 83%, at least 84%, at least 85%, at least 90%, at least 95%, at least 99%, or 100%) identical to the sequence set forth any one of SEQ ID NOs: 4 to 8. For example, a TRAILshort antibody heavy chain VH domain can have an amino acid sequence that is at least 75% identical to SEQ ID NO:4. For example, a TRAILshort antibody heavy chain VH domain can have an amino acid sequence that is at least 75% identical to SEQ ID NO:6.

Examples of TRAILshort antibody heavy chains are set forth below:

HC0:
(SEQ ID NO: 9)
MGWTLVFLFLLSVTAGVHSQVQLQQSGPELVKPGASVKISCKASGYIFTN

NDMNWVKQRPGQGLEWIGGIDPGDGRTKYNEKFKGKATLTADKFSNTVYM

QLSSLTSENSAVYFCGRGGYEFGIDYWGQGTSVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK;

HC1:
(SEQ ID NO: 10)
MGWTLVFLFLLSVTAGVHSQVQLVQSGAEVKKPGATVKISCKVSGYIFTN

NDMNWVQQAPGKGLEWMGGIDPGDGRTKYNEKFKGRVTITADESTSTAYM

ELSSLRSEDTAVYYCGRGGYEFGIDYWGQGTLVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK;

HC2:
(SEQ ID NO: 11)
MGWTLVFLFLLSVTAGVHSQVQLVQSGAEVKKPGASVKVSCKASGYIFTN

NDMNWVRQAPGQGLEWMGGIDPGDGRTKYNEKFKGRVTMTRDTSTNTVYM

ELSSLTSEDTAVYFCGRGGYEFGIDYWGQGTTVTVSSASTKGPSVFPLAP

SSKSTSGGTAALGCLVKDYFPEPVTVSWNSGALTSGVHTFPAVLQSSGLY

```
SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK;

HC3:
                              (SEQ ID NO: 12)
MGWTLVFLFLLSVTAGVHSQVQLVQSGAEVKKPGSSVKVSCKSSGYIFTN

NDMNWVRQAPGQGLDWMGGIDPGDGRTKYNEKFKGRVTISADIFSNTAYM

ELNSLTSEDTAVYFCGRGGYEFGIDYWGQTTVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK;
and

HC4:
                              (SEQ ID NO: 13)
MGWTLVFLFLLSVTAGVHSQVQLVESGAEVKKPGASVKVSCKVSGYIFTN

NDMNWVRQAPGEGLEWMGGIDPGDGRTKYNEKFKGRVTMTEDTSTDTAYM

ELSSLRSEDTAVYYCGRGGYEFGIDYWGQTTVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK.
```

A TRAILshort antibody (e.g., antibody Ab866) VL domain can include the CDRs set forth below:

```
VL CDR1:  KSSQSLLNSGNQKNSLA;   (SEQ ID NO: 14)

VL CDR2:  GASTRES;             (SEQ ID NO: 15)
and

VL CDR3:  QNDHSFPLT.           (SEQ ID NO: 16)
```

Examples of TRAILshort antibody VL domains including VL CDR1, VL CDR2 and VL CDR3 include, without limitation, the VL domains set forth below:

```
VL0:
                              (SEQ ID NO: 17)
DIVMTQSPSSLSVSAGEKVTMSCKSSQSLLNSGNQKNSLAWYQQKPGRPP

TLLISGASTRESGVPDRFTGSGSGTDFTLTISSVQAEDLAVYYCQNDHSF

PLTFGAGTKLELK;

VL1:
                              (SEQ ID NO: 18)
DVVMTQSPDSLAVSLGERATINCKSSQSLLNSGNQKNSLAWYQQKPGQPP

KLLIYGASTRESGVPDRFSGSGSGTDFTLTISSLQAEDVAVYYCQNDHSF

PLTFGQGTKLEIK;

VL2:
                              (SEQ ID NO: 19)
DIVMTQSPDSLAVSLGERATINCKSSQSLLNSGNQKNSLAWYQQKPGQPP

KLLIYGASTRESGVPDRFSGSGSGTDFTLTISSLQAEDVAVYYCQNDHSF

PLTFGGGTKLEIK;

VL3:
                              (SEQ ID NO: 20)
DIVMTQSPDSLAVSLGERATINCKSSQSLLNSGNQKNSLAWYQQRPGHPP

KLLLYGASTRESGVPDRFSGSGSGTDFTLTISSLQAEDVAVYYCQNDHSF

PLTFGGGTKVEIK;
and

VL4:
                              (SEQ ID NO: 21)
EIVLTQSPDSLAVSLGERATINCKSSQSLLNSGNQKNSLAWYQHKPGRPP

KLLIYGASTRESGVPDRFSGSGSGEDFTLTISSLQAEDVAVYYCQNDHSF

PLTFGPGTKVDLK.
```

In some cases, a TRAILshort antibody VL domain can have an amino acid sequence that is at least 75 percent (e.g., at least 78%, at least 79%, at least 80%, at least 81%, at least 82%, at least 83%, at least 84%, at least 85%, at least 90%, at least 95%, at least 99%, or 100%) identical to the sequence set forth any one of SEQ ID NOs: 17 to 21. For example, a TRAILshort antibody VL domain can have an amino acid sequence that is at least 75% identical to SEQ ID NO:17. For example, a TRAILshort antibody VL domain can have an amino acid sequence that is at least 75% identical to SEQ ID NO:20.

Examples of TRAILshort antibody light chains are set forth below:

```
LC0:
                              (SEQ ID NO: 22)
MVSSAQFLGLLLLCFQGTRCDIVMTQSPSSLSVSAGEKVTMSCKSSQSLL

NSGNQKNSLAWYQQKPGRPPTLLISGASTRESGVPDRFTGSGSGTDFTLT

ISSVQAEDLAVYYCQNDHSFPLTFGAGTKLELKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC;

LC1:
                              (SEQ ID NO: 23)
MVSSAQFLGLLLLCFQGTRCDVVMTQSPDSLAVSLGERATINCKSSQSLL

NSGNQKNSLAWYQQKPGQPPKLLIYGASTRESGVPDRFSGSGSGTDFTLT

ISSLQAEDVAVYYCQNDHSFPLTFGQGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC;
```

-continued

LC2:
(SEQ ID NO: 24)
MVSSAQFLGLLLLCFQGTRCDIVMTQSPDSLAVSLGERATINCKSSQSLL

NSGNQKNSLAWYQQKPGQPPKLLIYGASTRESGVPDRFSGSGSGTDFTLT

ISSLQAEDVAVYYCQNDHSFPLTFGGGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC;

LC3:
(SEQ ID NO: 25)
MVSSAQFLGLLLLCFQGTRCDIVMTQSPDSLAVSLGERATINCKSSQSLL

NSGNQKNSLAWYQQRPGHPPKLLLYGASTRESGVPDRFSGSGSGTDFTLT

ISSLQAEDVAVYYCQNDHSFPLTFGGGTKVEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC;
and

LC4:
(SEQ ID NO: 26)
MVSSAQFLGLLLLCFQGTRCEIVLTQSPDSLAVSLGERATINCKSSQSLL

NSGNQKNSLAWYQHKPGRPPKLLIYGASTRESGVPDRFSGSGSGEDFTLT

ISSLQAEDVAVYYCQNDHSFPLTFGPGTKVDLKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC.

A TRAILshort antibody described herein can include any combination of a heavy chain described herein and a light chain described herein. In some cases, a TRAILshort antibody can include HC2 and LC3.

In some cases, a TRAILshort antibody described herein can include (e.g., be fused to or coupled to) one or more labels (e.g., detectable labels). A label can be, without limitation, a fluorescent label (e.g., a fluorophore), a radioactive label, or an enzyme. Examples of detectable labels include, without limitation, R-Phycoerythrin (PE), CTO, GFP, fluorogen-activating protein (FAP), Gaussia Luciferase (GLuc), Cypridina Luciferase (Cluc), and radionuclides, and biotin.

In some cases, one or more TRAILshort antibodies (e.g., one, two, three, four, five, or more TRAILshort antibodies) can be administered to a mammal to treat a disease and/or an infection. For example, two or more TRAILshort antibodies can be administered to a mammal (e.g., a human) to treat a disease and/or an infection.

In some cases, a composition including one or more TRAILshort antibodies can be administered to a mammal having a disease and/or an infection as a sole active ingredient.

In some cases, a composition including one or more TRAILshort antibodies can be administered to a mammal having a disease and/or an infection as a combination therapy with one or more additional agents/therapies used to treat the disease and/or the infection. For example, a combination therapy used to treat a mammal having a disease and/or an infection can include administering to the mammal (e.g., a human) one or more TRAILshort antibodies in combination with one or more cell based therapies and/or one or more TRAIL-based therapies. TRAIL-based therapies can include, for example, TRAIL modulators including, but not limited to, recombinant TRAIL (e.g., dulanermin), anti-TRAIL-R1 antibodies (e.g., mapatumumab), anti-TRAIL-R2 antibodies (e.g., conatumumab, lexatumumab, tigatuzumab, drozitumab, LBY-135), TRAIL oligomers (e.g. ABBV-621), and/or TRAILshort extracellular domain:Fc fusions. In some cases, a TRAIL modulator can be a TRAIL agonist. In some cases, a TRAIL modulator can include (e.g., be fused to or coupled to) one or more additional domains (e.g., domains to enhance stability and/or function such as poly-Histidine, FLAG epitopes, isoleucine zipper motifs (LZ), the Fc portion of human immunoglobulins, albumin, and/or nanoparticles). In cases where two or more (e.g., two, three, four, or more) TRAIL modulators are administered to a mammal, the TRAIL modulators can be administered singly or in any combination. Cell based therapies can include, for example, adoptive cell transfer therapies (e.g., adoptive T cell therapy) including, but not limited to, adoptive transfer of c tumor-infiltrating lymphocytes (TIL) including autologous TILs, TILs genetically engineered with alpha-beta T cell receptors, TILs genetically engineered with chimeric antigen receptors (CAR T cell therapy) and/or genetically engineered NK or NK/T cells.

A combination therapy used to treat a mammal having a cancer can include administering to the mammal (e.g., a human) a composition including one or more TRAILshort antibodies and one or more cancer treatments such as chemotherapy agents including, but not limited to, alkylating agents (e.g., altretamine, busulfan, carboplatin, carmustine, chlorambucil, cisplatin, cyclophosphamide, dacarbazine, lomustine, melphalan, oxalaplatin, temozolomide, and thiotepa), antimetabolites (e.g., 5-FU), 6-mercaptopurine, capecitabine, cytarabine, floxuridine, fludarabine, gemcitabine, hydroxyurea, methotrexate, and pemetrexed), anthracycline antibiotics (e.g., daunorubicin, doxorubicin, epirubicin, and idarubicin), non-anthracycline antibiotics (e.g., actinomycin-D, bleomycin, mitomycin-C, and mitoxantrone), topoisomerase I inhibitors (e.g., topotecan and irinotecan (e.g., CPT-11)), topoisomerase II inhibitors (e.g., etoposide (e.g., VP-16), teniposide, and mitoxantrone), mitotic inhibitors (e.g., docetaxel, estramustine, ixabepilone, paclitaxel, vinblastine, vincristine, and vinorelbine), corticosteroids (e.g., prednisone, ethylprednisolone, and dexamethasone), enzymes (e.g., L-asparaginase), and/or proteasome inhibitors (e.g., bortezomib); differentiating agents including, but not limited to, retinoids, tretinoin, bexarotene, and arsenic trioxide; cocktail therapies (e.g., a combination of cyclophosphamide, doxorubicin, vincristine, and prednisolone (CHOP), or a combination of rituximab, cyclophosphamide, doxorubicin, vincristine, and prednisolone (R-CHOP)); monoclonal antibodies including, but not limited to, anti-HER2 antibodies (e.g., trastuzumab and pertuzumab), anti-CTLA-4 antibodies (e.g., ipilimumab), anti-GD2 antibodies (e.g., dinutuximab), anti-IL-6 antibodies (e.g., siltuximab), anti-EGFR antibodies (e.g., cetuximab, panitumumab, and necitumumab), anti-VEGF antibodies (e.g., ramucirumab and bevacizumab), anti-PD-1 antibodies (e.g., pembrolizumab and nivolumab), anti-PD-L1 antibodies (e.g., atezolizumab), anti-PDGF antibodies (e.g., olaratumab), anti-RANK antibodies (e.g., denosumab), anti-CD3 antibodies (e.g., blinatumomab), anti-CD19 antibodies (e.g., blinatumomab), anti-CD20 antibodies (rituximab, ofatumumab, and obinutuzumab), anti-CD38 antibodies (e.g., daratumumab), anti-CD52 antibodies (e.g., alemtuzumab), and anti-SLAMF7 antibodies (e.g., elotuzumab); antibody-drug conjugates including, but not limited to, gemtuzumab ozogamicin, brentuximab vedotin, trastuzumab, and emtansine; targeted small molecules including, but not limited to, tyrosine-kinase inhibitors (e.g., VEGF inhibitors (such as apatinib), c-Met inhibitors (such as cabozantinib), ALK inhibitors (such as alectinib and crizotinib), Brc-Abl inhibitors (such as dasatinib, imatinib, and nilotinib), EGFR inhibitors (such as erlotinib and gefitinib), HER2 inhibitors (such as lapatinib), multi-targeted tyrosine-kinase inhibitors (such as sorafenib and sunitinib), JAK1 inhibitors (such as tofacitinib), MEK inhibitors (such as cobimetinib and trametinib), proteasome inhibitors (such as ixazomib, carfilzomib, bortezomib, disulfiram, and lactacystin), estrogen receptor modulators (such as tamoxifen), Bcl-2 inhibitors (such as obatoclax, navitoclax, and gossypol), PARP inhibitors (such as iniparib and olaparib), PI3K inhibitors (such as perifosine), BRAF inhibitors (such as dabrafenib and vemurafenib), MEK inhibitors (such as trametinib), CDK inhibitors (such as abemaciclib, palbociclib, ribociclib, and trilaciclib), selective estrogen receptor degraders (such as fulvestrant), BET inhibitors, serine/threonine kinase inhibitors (such as temsirolimus, everolimus, vemurafenib, trametinib, and dabrafenib); small molecule drug conjugates including, but not limited to, vintafolide; radiation therapy (e.g., external beam therapy, intensity-modulated radiation therapy, image-guided radiation therapy, proton beam therapy); brachytherapy; and/or surgery (e.g., surgical resection of a tumor, a portion of a tumor, or a metastasis).

A combination therapy used to treat a mammal having a liver condition can include administering to the mammal (e.g., a human) a composition including one or more TRAILshort antibodies and one or more liver disease treatments including, but not limited to, weight loss, vaccinations against liver diseases (e.g., hepatitis A, hepatitis B, and hepatitis C), vitamin E, and/or coffee.

A combination therapy used to treat a mammal having an infection (e.g., a viral infection) can include administering to the mammal (e.g., a human) a composition including one or more TRAILshort antibodies and one or more infection treatments such as antiretroviral therapies including, but not limited to, nucleoside reverse transcriptase inhibitors (e.g., abacavir, didanosine, emtricitabine, entecavir, lamivudine, stavudine, tenofovir disoproxil fumarate, zalcitabine, and zidovudine); non-nucleoside reverse transcriptase inhibitors (e.g., delavirdine, efavirenz, etravirine, nevirapine, and rilpivirine); nucleotide reverse transcriptase inhibitors (e.g., adefovir and tenofovir); fusion inhibitors (e.g., enfuvirtide); entry inhibitors (e.g., maraviroc); integrase inhibitors (e.g., dolutegravir, elvitegravir (with or without ritonovair and/or cobisistat), and raltegravir); maturation inhibitors (e.g., bevirimat); protease inhibitors (e.g., amprenavir, fosamprenavir, indinavir, lopinavir, nelfinavir, ritonavir, saquinavir, atazanavir, darunavir, and tipranavir); uncoating inhibitors (e.g., TRIM5alpha); transcription inhibitors (e.g., tat antagonists); and/or translation inhibitors (e.g., trichosanthin); pegylated interferon alfa (PEG-IFN-a); daclatasvir; elbasvir; grazoprevir; glecaprevir; pibrentasvir; ledipasvir; sofosbuvir; ombitasvir; paritaprevir; ritonavir; dasabuvir; simeprevir; velpatasvir; and voxilaprevir.

In cases where one or more TRAILshort antibodies are used in combination with one or more additional agents used to treat a disease and/or an infection, the one or more additional agents can be administered at the same time or independently. For example, the composition including one or more TRAILshort antibodies can be administered first, and the one or more additional agents administered second, or vice versa. In embodiments where one or more TRAILshort antibodies are used in combination with one or more additional therapies used to treat a disease and/or an infection, the one or more additional therapies can be performed at the same time or independently of the administration of one or more TRAILshort antibodies. For example, the composition including one or more TRAILshort antibodies can be administered before, during, or after the one or more additional therapies are performed.

In some cases, one or more TRAILshort antibodies can be formulated into a pharmaceutically acceptable composition for administration to a mammal having a disease and/or an infection. For example, a therapeutically effective amount of a TRAILshort antibody can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more TRAILshort antibodies can be designed for oral, parenteral (including subcutaneous, intramuscular, intravenous, intraperitoneal, intrathecal, and intradermal), or inhaled administration. When being administered orally, a pharmaceutical composition containing one or more TRAILshort antibodies can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. Compositions for inhalation can be delivered using, for example, an inhaler, a nebulizer, and/or a dry powder inhaler. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

In some cases, a pharmaceutically acceptable composition including one or more TRAILshort antibodies can be administered locally or systemically. For example, a composition containing a TRAILshort antibody can be administered systemically by an oral administration to or inhalation by a mammal (e.g., a human).

Effective doses can vary depending on the severity of the disease and/or the infection, the route of administration, the age and general health condition of the subject, excipient usage, the possibility of co-usage with other therapeutic treatments such as use of other agents, and the judgment of the treating physician.

In some cases, an effective amount of a composition containing one or more TRAILshort antibodies can be any amount that reduces the severity, or occurrence, of symptoms of the disease and/or the infection to be treated without producing significant toxicity to the mammal. In some cases, an effective amount of a composition containing one or more TRAILshort antibodies can be any amount that reduces the number of diseased cells (e.g., cancer cells) and/or infected cells without producing significant toxicity to the mammal. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the disease and/or the infection may require an increase or decrease in the actual effective amount administered.

In some cases, the frequency of administration can be any frequency that reduces the severity, or occurrence, of symptoms of the disease and/or the infection to be treated without producing significant toxicity to the mammal. In some cases, the frequency of administration can be any frequency that reduces the number of diseased cells (e.g., cancer cells) and/or infected cells without producing significant toxicity to the mammal. For example, the frequency of administration can be from about once a month to once every two weeks, from about once a week to about three times a day, from about twice a month to about six times a day, or from about twice a week to about once a day. In some cases, the frequency of administration can be weekly. In some cases, the frequency of administration can be every two weeks. The frequency of administration can remain constant or can be variable during the duration of treatment. A course of treatment with a composition containing one or more TRAILshort antibodies can include rest periods. For example, a composition containing one or more TRAILshort antibodies can be administered daily over a two-week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the disease and/or the infection may require an increase or decrease in administration frequency.

In some cases, an effective duration for administering a composition containing one or more TRAILshort antibodies can be any duration that reduces the severity, or occurrence, of symptoms of the disease and/or the infection to be treated without producing significant toxicity to the mammal. In some cases, an effective duration for administering a composition containing one or more TRAILshort antibodies can be any duration that reduces the number of diseased cells (e.g., cancer cells) and/or infected cells without producing significant toxicity to the mammal. For example, the effective duration can vary from several days to several weeks, months, or years. In some cases, the effective duration for the treatment of a disease and/or an infection can range in duration from about one month to about 10 years. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of the disease and/or the infection being treated can be monitored. Any appropriate method can be used to determine whether or not the severity of a disease and/or an infection is reduced. For example, the severity of a disease (e.g., cancer) can be assessed using imaging techniques (with or without contrast), biopsy techniques, bone marrow aspiration, colonoscopy, sigmoidoscopy, digital rectal exam, blood assay, platelet assay, fecal assay, urine assay, endoscopic techniques, ELISA techniques, PCR-based techniques, blotting techniques (e.g., western blot), flow cytometry, genetic analysis (e.g., for gene rearrangements), and/or histological techniques at different time points. For example, the severity of an infection can be assessed using antibody techniques, viral antigen detection tests, culturing techniques, ELISA techniques, PCR-based techniques (e.g., viral load test), blotting techniques (e.g., western blot), and/or histological techniques at different time points. Any appropriate method can be used to monitor the response to TRAILshort antibody therapies or combination therapies including TRAILshort antibodies. For example, techniques to detect levels of TRAIL and/or TRAILshort including ELISA techniques, PCR-based techniques, blotting techniques (e.g., western blot), hybridization techniques (e.g., ISH) and/or histological techniques (e.g., IHC).

In some cases, monitoring the response to TRAILshort antibody therapies or combination therapies including TRAILshort antibodies can include theranostics. For example, one or more TRAILshort antibodies can be administered to a mammal having a disease and/or infection, and the disease and/or infection can be monitored simultaneously. For example, one or more TRAILshort antibodies described herein (e.g., an antibody including a VH domain including the CDRs set forth in SEQ ID NO:1, SEQ ID NO:2, and SEQ ID NO:3; and a VL domain including the CDRs set forth in SEQ ID NO:14, SEQ ID NO:15, and SEQ ID NO:16) can be labelled with radionuclides to enable monitoring with PET or SPECT imaging.

The invention will be further described in the following examples, which do not limit the scope of the invention described in the claims.

EXAMPLES

Example 1: Resistance to TRAIL is Conferred by Microvesicle Associated TRAILshort and is Reversed by Antibody Neutralization Summary TRAIL binds to TRAIL-R1 or TRAIL-R2 and can induce apoptosis in tumor cells and/or virally infected cells while sparing normal cells. Unfortunately, clinical success of TRAIL-receptor-targeting therapies has been limited. The following data indicate that type I interferon signaling induces expression of TRAILshort, and that TRAILshort is shed in microvesicles into the cellular microenvironment where it can be taken up by bystander cells. TRAILshort binds to TRAIL-R1 and R2, but not TRAIL decoy receptors R3 and R4, and prevents full-length-TRAIL from inducing cell death. TRAILshort mediated protection against TRAIL killing occurs in trans, since cells that do not produce TRAILshort are protected against TRAIL after binding TRAILshort. Recombinant TRAILshort is sufficient to protect cells against TRAIL induced killing, while depletion of TRAILshort with a specific antibody restores TRAIL sensitivity. These results establish a paradigm for understanding and overcoming TRAIL resistance.

Results

TRAILshort is Produced by Both Uninfected and HIV Infected Cells

TRAILshort production in HIV infected versus uninfected cells was assessed using single cell mRNA analysis.

Figure 1:
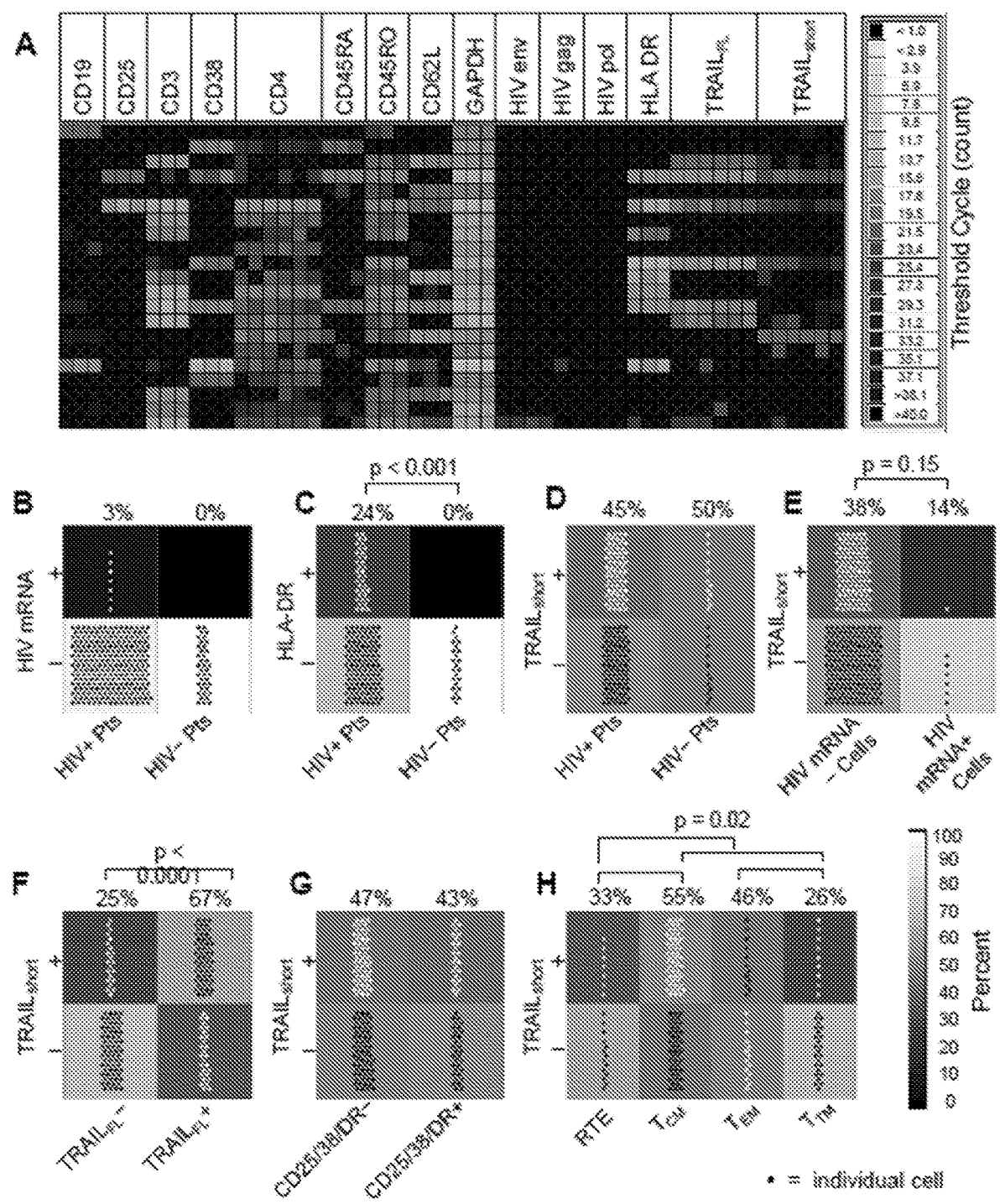
FIG. 1 shows that TRAILshort is produced in both uninfected and HIV infected cells. Single cell gene expression in primary CD4 T cells from HIV positive patients (HIV+; N=6) and HIV negative controls (HIV−; N=3) was assessed by Fluidigm technology. A) Representative heat map of expression of mRNA transcripts for TRAIL, TRAILshort, mRNA levels, and cell surface markers in single cells from a single HIV positive patient. B) HIV mRNA gene expression in cells of HIV+ and HIV− patients (Pts). C) HLA-DR gene expression in cells of HIV+ and HIV− Pts. D) TRAILshort message expression in cells of HIV+ and HIV− Pts. E) TRAILshort expression in HIV+ and HIV− cells, as determined by cell expression of HIV genes. F) TRAILshort expression in single cells expressing TRAIL or not expressing TRAIL. G) TRAILshort expression in resting (CD25-, CD38- and HLA-DR-) or activated (any CD25, CD38, and/or HLA-DR expression). H) TRAILshort expression in T cell subsets—RTE: recent thymic immigrants; TCM: central memory T cells; TEM: effector memory T cells; TTM: transitional memory T cells.

In these experiments single CD4 T cells from HIV infected or uninfected donors were separated by an integrated fluidic circuit and individual cell analyses were performed using PCR for HIV specific targets, TRAILshort and TRAIL receptor/ligand, and markers of cell lineage and activation status (FIG. 1A).

The specificity of the assay was confirmed by observing that HIV uninfected donors had no cells which contained HIV transcripts, and that very few of the CD4 T cells from HIV infected donors contained HIV transcripts (FIG. 1B). The inappropriate and excessive immune activation observed in patients with HIV infection was also observed, that is, more cells from HIV infected donors expressed the activation marker HLA-DR than cells from HIV uninfected donors (FIG. 1C). Both cells from HIV infected as well as uninfected donors contained transcripts for TRAILshort (FIG. 1D), and both HIV infected (HIV mRNA+) as well as HIV uninfected (HIV mRNA−) cells from HIV infected donors expressed TRAILshort (FIG. 1E), indicating that HIV infection is not required for production of TRAILshort. The majority of individual cells expressed either $TRAIL_{FL}$ and TRAILshort, or neither $TRAIL_{FL}$ nor TRAILshort, consistent with TRAILshort being a splice variant of $TRAIL_{FL}$ (FIG. 1F). In order to gain insight into what stimuli induce TRAILshort expression, whether such expression was correlated with cellular activation was assessed and found that TRAILshort message was not associated with immune activation as determined by the presence of transcripts for CD25, CD38, or HLA-DR (FIG. 1G). Within the CD4 T cell subsets represented in this analysis, more of the Central memory CD4 T cells ($T_{CM}$) contained TRAILshort transcripts than Recent Thymic Emigrants (RTE), Effector memory CD4 T cells (TEM), or Transitional Memory CD4 T cells ($T_{TM}$) (FIG. 1H). Thus the data indicate that TRAILshort can be expressed in individual cells which are not infected by HIV.

Type I Interferons Drive Production of TRAILshort

Figure 2:
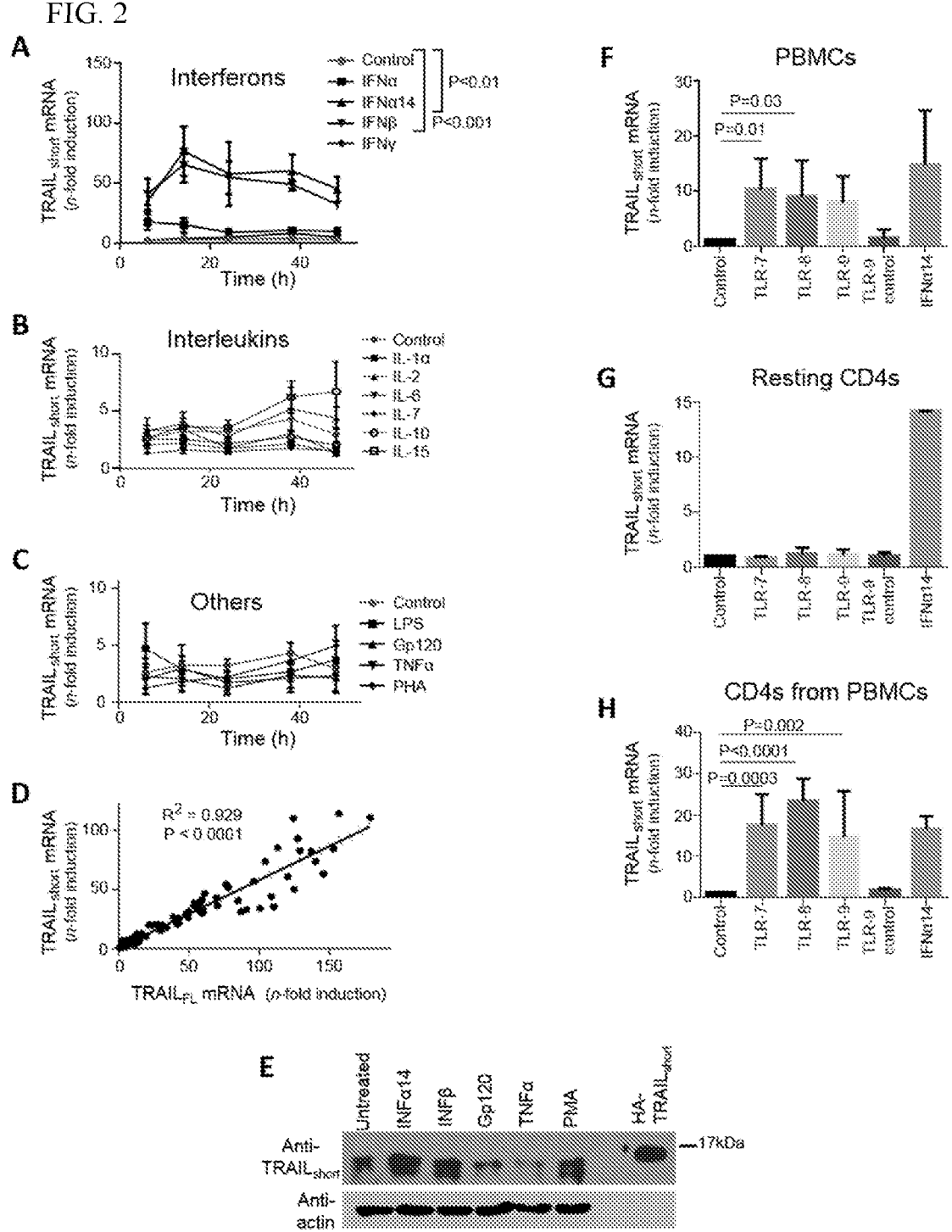
FIG. 2 shows that Type I interferons drive production of TRAILshort. For A, B, and C, primary uninfected resting (CD25-, CD69-, HLA-DR-) CD4 T cells were either unstimulated, or stimulated with interferons (A), interleukins (B), or other biologically active proteins (C) and TRAILshort mRNA measured by qRT-PCR. D) Concomitant TRAIL and TRAILshort mRNA expression was compared across samples. E) Resting CD4 T cells were stimulated as depicted and TRAILshort protein expression assessed by western blot. F) PBMCs were treated with vehicle control, TLR 7, 8, or 9 agonists or TL9 inactive control for 24 hours and TRAILshort mRNA expression measured. G) Resting isolated CD4 T cells were treated similarly as the PBMCs in (F) and TRAILshort mRNA measured. H) PBMCs were treated as in (F), and after 24 hours, CD4 T cells were separated and TRAILshort mRNA measured in the CD4 subset. Data represent means (SEM) of 5 independent experiments per treatment. P<0.05 considered statistically significant.

Since HIV uninfected cells are capable of making TRAILshort, it becomes relevant to understand which stimuli are responsible for driving the production of TRAILshort; HIV proteins, HIV induced cytokines, and/or IFN might be responsible for inducing TRAILshort expression. HIV infection produces a number of bioactive HIV encoded proteins that have pleotropic effects on host cells. HIV infection of individual cells can be recognized by a range of Pattern Recognition Receptors (PRR), including TLR and RIG, which culminate in production of type I IFN and consequent induction of IFN stimulated genes (ISG) (Zitvogel et al., 2015 *Nat Rev Immunol* 15:405-414). To determine which of these stimuli drives TRAILshort production, a panel of cytokines, IFN, and HIV proteins that are present in the plasma of infected patients was screened to assess which if any of these stimuli can induce a resting (CD25−, CD69−, HLA-DR−) CD4 T cell to produce TRAILshort. IFNα14 and IFNβ significantly induced TRAILshort message by ~50 fold (FIGS. 2A & E) while a panel of cytokines, including inflammatory cytokines, modestly but non-significantly increased the expression of TRAILshort message only by several fold (FIG. 2B). Similarly, TNFα, LPS, and gp120 minimally impacted TRAILshort expression (FIG. 2C). Similar effects of type I interferons compared to other stimuli were found when TRAILshort protein levels in treated samples were analyzed (FIG. 2E). In the same samples $TRAIL_{FL}$ message was measured and a tight linear correlation between $TRAIL_{FL}$ expression and TRAILshort expression was found (FIG. 2D), consistent with FIG. 1F. Together these data support the conclusion that TRAILshort is a de facto Interferon Stimulated Gene, which is therefore likely expressed in diverse conditions characterized by type I interferon signaling.

The Carboxyl Terminus of TRAILshort is Externalized on the Plasma Membrane and Interacts with TRAIL Receptors R1 & R2 but not TRAIL Receptors R3 & R4

Figure 3:
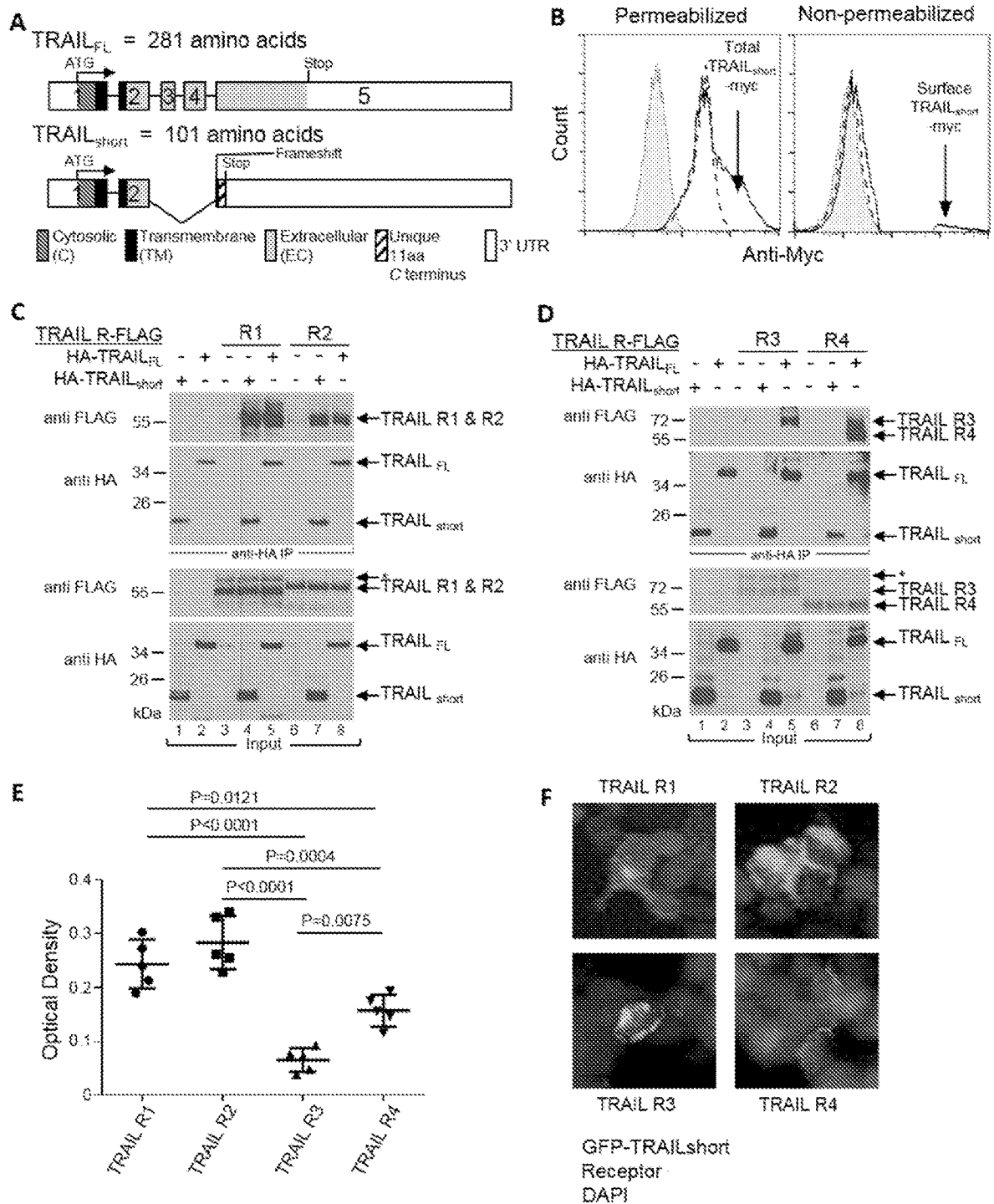
FIG. 3 shows that C-terminus of TRAILshort is extracellular and interacts with TRAIL "death" receptors, but not with TRAIL "decoy" receptors. A) Schematic alignment of the exons, cytosolic, transmembrane, extracellular, and 3' untranslated regions (UTR) of $TRAIL_{FL}$ and TRAILshort. B) 293T cells transiently expressing TRAILshort with c-myc cloned into the EC domain were stained with an anti-c-myc antibody or an isotype control. Key: Grey filled (eGFP+TRAILshort myc with Isotype control); Dashed line (eGFP, anti-myc); Solid line (eGFP+TRAILshort, anti-myc). C) Lysates from 293T cell transiently expressing C-terminal FLAG-tagged TRAIL R1 or R2 were combined with lysates from cells expressing N-terminal HA-tagged $TRAIL_{FL}$ or N-terminal HA-tagged TRAILshort (as indicated at top of panels), then immunoprecipitated with anti-HA antibody. The complexed proteins were resolved and immunoblotted for FLAG or for HA. Total input lysates are shown in the lower two panels. D) Lysates from 293T cells expressing decoy TRAIL receptors R3 and R4 were combined with lysates from cells expressing N-terminal HA-tagged $TRAIL_{FL}$ or N-terminal HA-tagged TRAILshort (as indicated at top of panels), then immunoprecipitated with anti-HA antibody. The complexed proteins were resolved and immunoblotted for FLAG or for HA. Total input lysates are shown in the lower two panels. E) Binding of TRAILshort to TRAIL receptors R1, R2, R3 and R4 were determined by ELISA. F) Binding of TRAILshort to TRAIL receptors R1, R2, R3 and R4 visualized by confocal microscopy. Data shown is representative of four independent experiments.

$TRAIL_{FL}$ is expressed as a single pass type II transmembrane protein with an extracellular C-terminal domain. The C-terminal region of $TRAIL_{FL}$ containing amino acids ~95-281 is responsible for pro-apoptotic function, and forms homotrimers coordinated around a central zinc ion (Cha et al., 1999 *Immunity* 11:253-261). TRAILshort occurs as a consequence of a splicing event in which exons 3 and 4 are deleted and a frame shift is introduced in exon 5 resulting in a premature stop codon and a novel 11 amino acid C terminus (FIG. 3A).

Whether TRAILshort traffics to the plasma membrane and is present on the exterior surface of the cell was evaluated. To do so, a myc tag was inserted within the novel C terminus of TRAILshort and epitope accessibility was analyzed in nonpermeabilized or permeabilized transfected cells using flow cytometry. Whereas permeabilized control transfected cells contained detectable myc (likely reflecting endogenous myc), TRAILshort-myc transfected cells showed additional myc staining consistent with transfected protein expression (FIG. 3B, left panel). Non permeabilized samples of the same cells showed no surface myc staining of control transfected cells, yet a distinct population of surface myc positive cells was detectable following TRAILshort-myc expression (FIG. 3B, right panel) supporting the interpretation that the carboxyl terminus of TRAILshort is accessible in the extracellular environment.

$TRAIL_{FL}$ exerts its pro-apoptotic effect through binding to members of the TRAIL receptor family, of which there are four distinct member proteins. TRAIL-R1 and R2 contain Death Domains, which following ligand binding, recruit Fas-Associated protein with Death Domain (FADD), and lead to caspase-8 activation. TRAIL-R3 and R4 do not contain functional Death Domains, do not lead to caspase-8 activation, and are often considered "decoy" receptors. TRAIL receptor family members are also distinguished one from another by their varying abilities to bind $TRAIL_{FL}$. One isothermal titration calorimetry study showed $TRAIL_{FL}$ binding affinity to TRAIL-R2 was at least 35-fold higher than to TRAIL-R1 and 100-fold higher than to TRAIL-R3 (TRAIL-R4 was not assessed) (Truneh et al., 2000, *J Biol Chem* 275:23319-23325), while another showed TRAIL R4>R2>R3>R1, with dissociation constants ranging from 0.869 to 4.08 nM (Lang et al., 2016, *J Biol Chem* 291:5022-5037). These studies highlight TRAIL-R2 as the apoptosis inducing receptor with the highest affinity for $TRAIL_{FL}$.

To address whether TRAILshort also interacts with any other TRAIL receptor family members, cell lysates from 293T cells expressing C-terminal FLAG-tagged TRAIL-R1, R2, R3, or R4 were combined with cell lysates from cells expressing N-terminal HA-tagged $TRAIL_{FL}$ or N-terminal HA-tagged TRAILshort. The mixtures were immunoprecipitated with anti-HA and analyzed for FLAG containing proteins. Both FLAG-TRAIL-R1 and R2 were immunoprecipitated via HA-$TRAIL_{FL}$ (FIG. 3C). FLAG-TRAIL-R1 and R2 also co-immunoprecipitated HA-TRAILshort to a similar extent (FIG. 3C). However, while $TRAIL_{FL}$ associated with both TRAIL-R3 and R4, TRAILshort notably did not (FIG. 3D). TRAILshort therefore binds preferentially to the death inducing TRAIL-R1 and R2, while sparing the decoy receptors R3 and R4, suggesting that selective receptor binding may be central to the biologic effects of TRAILshort.

TRAILshort is Contained Within Extracellular Vesicles

It remains unknown how TRAILshort is released into that compartment. To explore this process, Jurkat T cells transfected with GFP or GFP-TRAILshort were analyzed by confocal microscopy. TRAILshort was observed to localize to the plasma membrane (FIG. 4A), which was confirmed by immunoblotting the heavy-membrane fraction of HIV-infected or control cells (FIG. 4B); purity of fractions was confirmed by cytosol specific HSP70. TRAILshort was found in the supernatant fraction of infected cultures. Moreover, supernatant associated TRAILshort migrated similarly to cell associated TRAILshort, suggesting that supernatant associated TRAILshort is unlikely to have been generated by a cleavage event (FIG. 4C).

Figure 4:
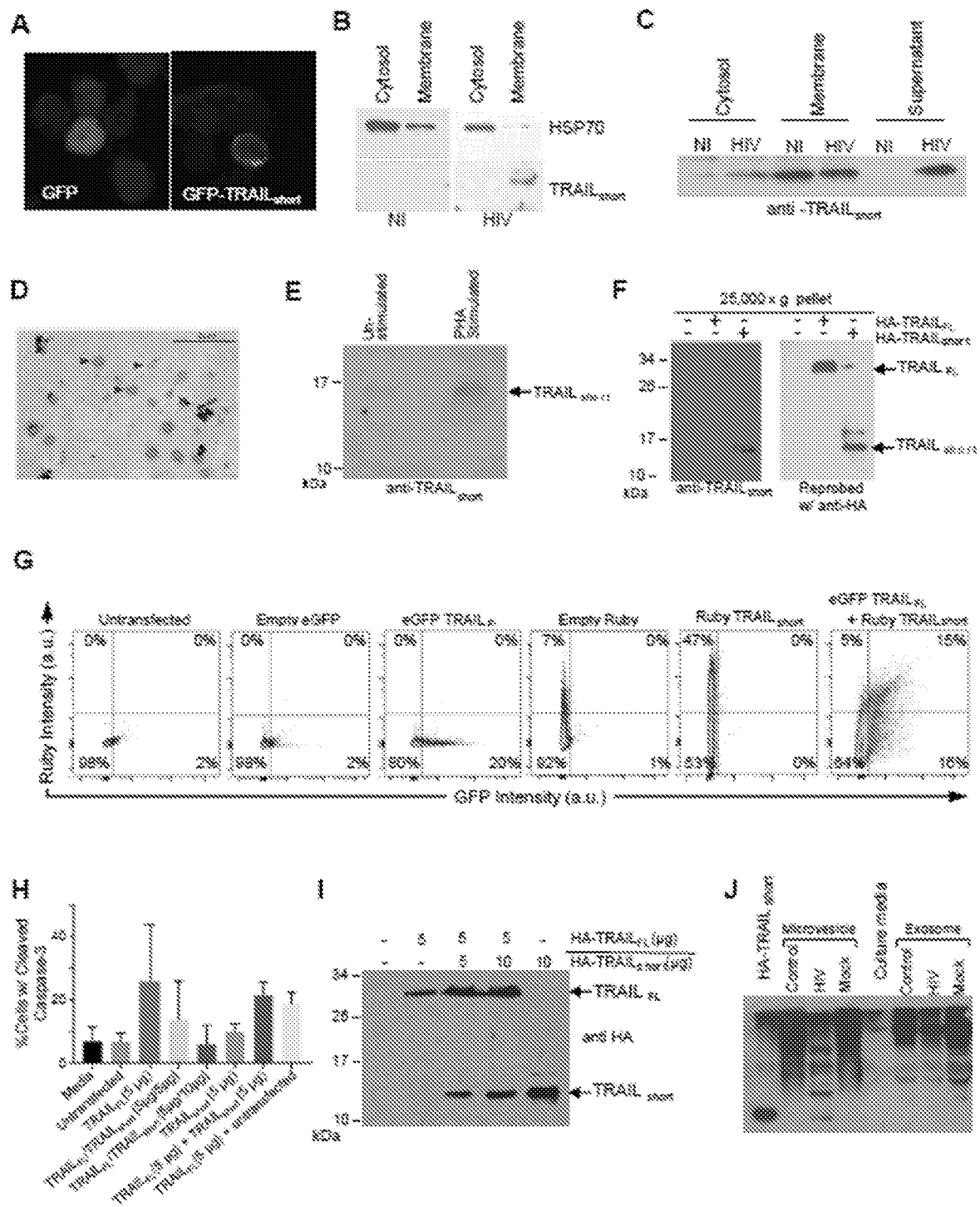
FIG. 4 shows that TRAILshort is contained in extracellular vesicles. A) Jurkat T cells transiently expressing GFP-TRAILshort were analyzed by confocal microscopy and cells were counter stained with DAPI. B) The membrane or cytosolic fractions of HIV infected and non-infected (NI) Jurkat T cells were analyzed for HSP 70 (cytosol selective protein) or for TRAILshort. C) Cytosolic, membrane, and supernatant fractions were prepared from HIV infected and non-infected (NI) Jurkat T cells and analyzed by western blotting with anti-TRAILshort antibody. D) Extracellular vesicles from PHA-stimulated CD4+ cells were fixed and stained with phosphotungstic acid, then analyzed by electron microscopy. Scale bar, 2 µm. E) Extracellular vesicles from PHA-stimulated and unstimulated CD4+ cells were analyzed by western blotting for TRAILshort. F) Western blot analysis of purified extracellular vesicle preparations from 293T cells transiently expressing HA-$TRAIL_{FL}$ and HA-TRAILshort. G) Flow cytometric analysis of extracellular vesicle preparations from supernatants of 293T cells transfected with eGFP-TRAILshort alone, Ruby-$TRAIL_{FL}$ alone. H) Extracellular vesicles from supernatant of 293T cells transfected with HA-$TRAIL_{FL}$ alone, HA-TRAILshort alone, or co-transfected with 1:1 or 1:2 ratios of HA-$TRAIL_{FL}$/HA-TRAILshort were used to treat target Jurkat T-cells. Apoptotic activity was determined by staining Jurkat cells for cleaved caspase 3. I) Western blot confirmation of HA-$TRAIL_{FL}$ and HA-TRAILshort expression in extracellular vesicles in 293T cells from (H). J) Supernatants from control, HIV infected, and mock infected primary CD4 T cells in culture were separated into microvesicle or exosome fractions as indicated and analyzed by western blotting with TRAILshort specific monoclonal antibody.

To examine if TRAILshort might be incorporated into extracellular vesicles, extracellular vesicles from PHA-stimulated and unstimulated CD4+cells were harvested by ultracentrifugation, fixed, and analyzed for size by electron microscopy revealing a range of 50 nm to ~400 nm with a median diameter of 136 nm (FIG. 4D). These results suggest the presence of both microvesicles (>100 nm) and exosomes (<100 nm). Western blot analysis of the same extracellular vesicles was performed using anti-TRAILshort antibody. This revealed a band at ~15 kDa (FIG. 4E) consistent with the extracellular vesicles containing TRAILshort. Whole cell lysates and purified extracellular vesicle preparations from 293T cells transfected with HA-TRAIL$_{FL}$ and HA-TRAILshort produced a similar pattern by western blot (FIG. 4F). The presence of extracellular vesicle associated with TRAILshort was further verified by transfecting 293T cells with eGFP-TRAIL$_{FL}$ and/or Ruby-TRAILshort and analyzing the supernatants with flow cytometry. Untransfected cell supernatants contained virtually no GFP or Ruby signal, whereas cells transfected with eGFP-TRAIL$_{FL}$ or Ruby-TRAILshort alone showed detectable expression of each protein individually. When cells were co-transfected with eGFP-TRAIL$_{FL}$ and Ruby-TRAILshort, vesicles were detectable with eGFP-TRAIL$_{FL}$ alone, Ruby-TRAILshort alone, and both eGFP-TRAIL$_{FL}$ and Ruby-TRAILshort. (FIG. 4G).

Microvesicle localized TRAILFL has been shown to be bioactive (Huber et al., 2005 Gastroenterology 128:1796-1804) and therefore whether TRAILshort in extracellular vesicles is bioactive as well was examined. 293T cells were transfected with HA-TRAILFL alone, HA-TRAILshort alone, both in a 1:1 ratio, or both in a 1:2 HA-TRAILFL: HA-TRAILshort ratio, and concentrated supernatants containing TRAILshort microvesicles were collected. Jurkat cells were incubated in either fresh media, media conditioned from untransfected 293T cells, or media conditioned from one of the four varieties of transfected 293T cells and were analyzed by flow cytometry for cleaved caspase-3 as a marker of cell death by apoptosis. Jurkat cells incubated with fresh media or media from untransfected 293T cells had low levels of basal apoptosis (~5%). By contrast, Jurkat cells incubated with media from 293T cells transfected with TRAILFL had >20% apoptosis, consistent with TRAILFL being active in microvesicle fractions. Significantly, when 293T cells were co-transfected with TRAILFL and TRAILshort, the degree of Jurkat T cell killing by the microvesicle preparations was reduced, and was lowest when greater amounts of TRAILshort was present (~3%-13%; FIG. 4H & I).

Whether TRAILshort is similarly associated with microvesicles and not exosomes as TRAILshort is a membrane associated protein with a transmembrane domain was tested. Supernatants from HIV infected primary CD4 T cell cultures were fractionated into microvesicles by ultracentrifugation or into exosomes by resin based extraction as described elsewhere (see, e.g., Taylor et al., 2011 *Methods Mol Biol* 728:235-246). Microvesicle preparations and exosomes were analyzed by immunoblot using our TRAILshort specific antibody, and identified TRAILshort only in the microvesicle preparations (FIG. 4J).

TRAILshort Protection from TRAIL can be Transferred to Neighboring Cells

Figure 5:
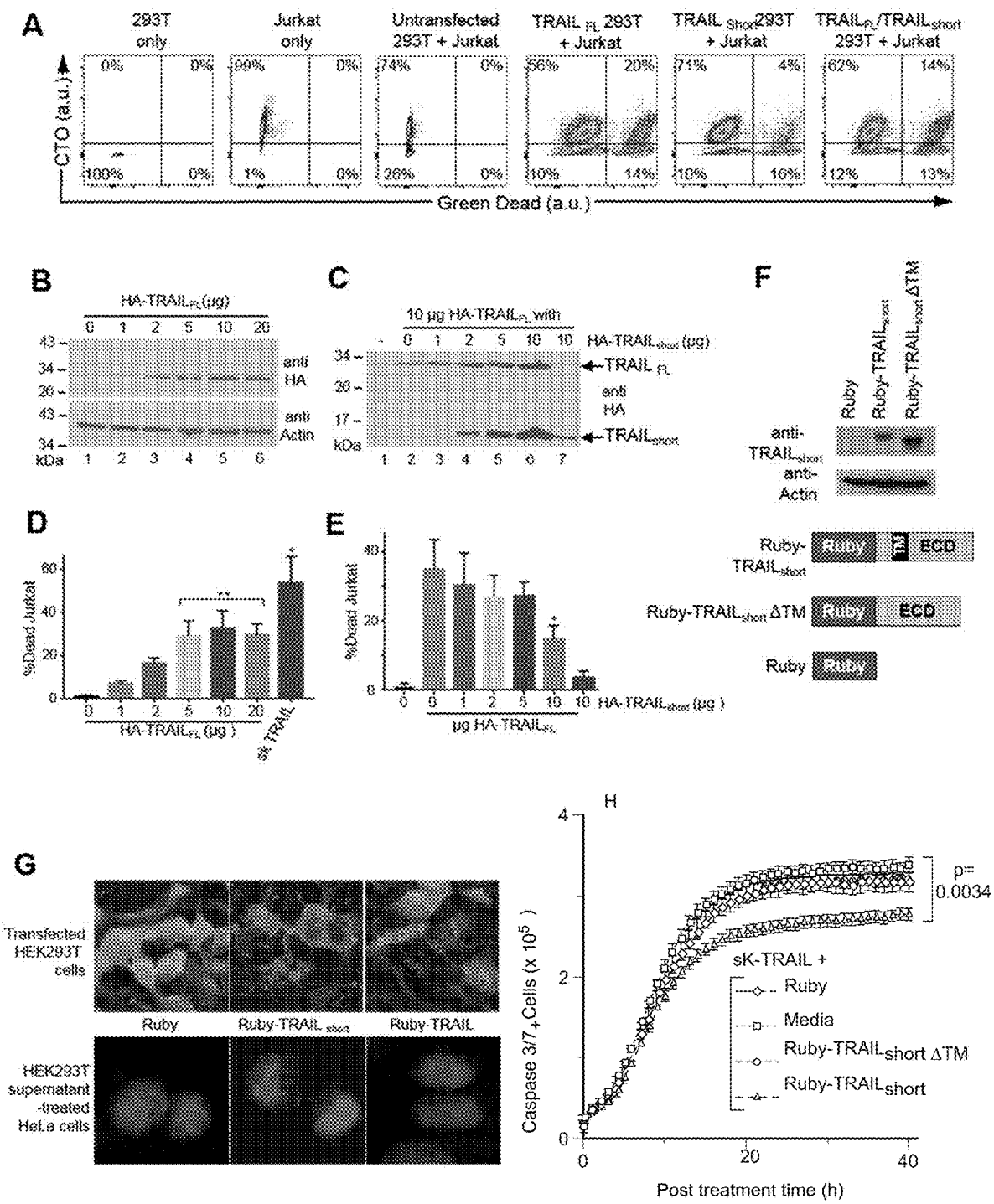
FIG. 5 shows that TRAILshort protection from TRAIL can be transferred to neighboring cells. A) Effector 293T cells expressing either $TRAIL_{FL}$, TRAILshort, or both were mixed with CTO-labeled target Jurkat T cells. Following incubation cells were analyzed by flow cytometry, gating on Cell Tracker Orange (CTO) positive (Jurkat) populations and staining for Live/Dead cells. B) 293T cells were transfected with 1, 2, 5, 10, or 20 µg of N-terminal HA-tagged $TRAIL_{FL}$ alone and analyzed by western with an anti-HA antibody. C) 293T cells were co transfected with 1, 2, 5, or 10 µg of TRAILshort and a constant 10 µg $TRAIL_{FL}$ and analyzed by western blot. D) 293T effector cells transfected with increasing amounts of $TRAIL_{FL}$ from (B) were co-cultured with CTO+ target Jurkat cells and the percentage CTO+ Jurkat cell killing was determined. E) 293T effector cells from (D), co-transfected with increasing amounts of TRAILshort at constant $TRAIL_{FL}$, were co-cultured with target cell and analyzed as in (C). F) Schematic of plasmids encoding N-terminal Ruby-tagged-TRAILshort (Ruby-TRAILshort), a construct missing the transmembrane domain (Ruby-TRAILshortΔTM), and the Ruby tag alone (bottom panel). Western analysis with anti-TRAILshort antibody and anti-actin controls of lysates from 293T cells transfected with these constructs (top panel). G) 293T cells were transfected with the constructs in (F) and representative micrographs are shown (top panel). Supernatants from the 293T transfected cells were harvested and used to treat target HeLa cells which were then analyzed by confocal microscopy. Representative micrographs superimposing the DAPI stained HeLa nuclei and ruby-TRAILshort or Ruby-TRAILshortΔTM filter channels are shown (bottom panel). HeLa cells treated with supernatant from Ruby TRAILshort expressing 293T cells only have punctate surface localized Ruby TRAILshort on plasma membranes. H) HeLa cells from (G) that were pre-treated with supernatants from 293T transfected with Ruby, Ruby-TRAILshort, or Ruby-TRAILshortΔTM were treated with a super killer (sk)-TRAIL. Cell killing was quantified by active caspase 3 staining over time. At the far right timepoint the four traces are, from top to bottom, sk-TRAIL+Ruby, sk-TRAIL+Ruby-TRAILshortΔTM, sk-TRAIL+media, sk-TRAIL+Ruby-TRAILshortΔTM. Data representative of four independent experiments. P<0.05 considered statistically significant by linear regression.

To assess the biological impact of TRAILshort expression TRAIL$_{FL}$, TRAILshort, or both were expressed in 293T cells used as effector cells. Target Jurkat T cells, which express TRAIL-R2, were labelled with Cell Tracker Orange (CTO), effector 293T cells were mixed with target CTO+ Jurkat cells, and analysis was carried out by flow cytometry gating on the CTO positive populations (FIG. 5A). Target Jurkat cells correlated positively with increasing amounts of transfected HA-TRAIL$_{FL}$ plasmids ranging from 7.1% to 32.8% with transfection of 1 μg to 20 μg HA-TRAIL$_{FL}$ (FIGS. 5B & C). Effector 293T cells were transfected with 10 μg of HA-TRAIL$_{FL}$ and increasing amounts of HA-TRAILshort, co-cultured with CTO labelled Jurkat T cells, and analyzed in a similar manner. Increasing amounts of TRAILshort plasmid led to increased expression of TRAILshort (FIG. 5D). This in turn resulted in decreasing amounts of Jurkat target cell killing (FIG. 5E). Therefore, TRAILshort co-expression with TRAIL$_{FL}$ antagonizes the apoptosis inducing activity of TRAIL$_{FL}$ in a dose dependent manner.

To examine if TRAILshort mediated resistance to TRAIL killing is transferrable from TRAILshort producing cells to bystander cells present in the microenvironment that do not produce TRAILshort, expression constructs of ruby tagged TRAILshort (ruby-TRAILshort) and ruby tagged TRAILshort missing the transmembrane domain (ruby-TRAILshortΔTM) were generated, and robust expression of each construct was verified (FIG. 5F). 293T cells transfected with ruby-TRAILshort demonstrated perimembrane expression of ruby, whereas, the ruby-TRAILshortΔTM expressing cells showed diffuse cytoplasmic expression (FIG. 5G, top panel). Supernatants from transfected cells were harvested and used to treat HeLa cells. Treated HeLa cells showed uptake of ruby-TRAILshort, but not ruby-TRAILshortΔTM (FIG. 5G, bottom panel), which is consistent with the understanding that the transmembrane domain is necessary for membrane localization of TRAILshort and also indicates that microvesicles containing TRAIL short are taken up by neighboring cells that do not produce TRAILshort. Whether these microvesicle treated HeLa cells acquired resistance to TRAIL mediated killing was tested. Untreated HeLa cells died in a time dependent manner following treatment with sk-TRAIL. Addition of supernatants from ruby transfected or ruby-TRAILshortΔTM transfected 293T cells did not appreciable alter sk-TRAIL killing, whereas, addition of supernatants from ruby-TRAILshort transfected cells reduced sk-TRAIL induced killing by ~20% (FIG. 5H).

Thus, TRAILshort expression by one cell can confer TRAIL resistance on another cell mediated by microvesicle transfer of TRAILshort.

Figure 6:
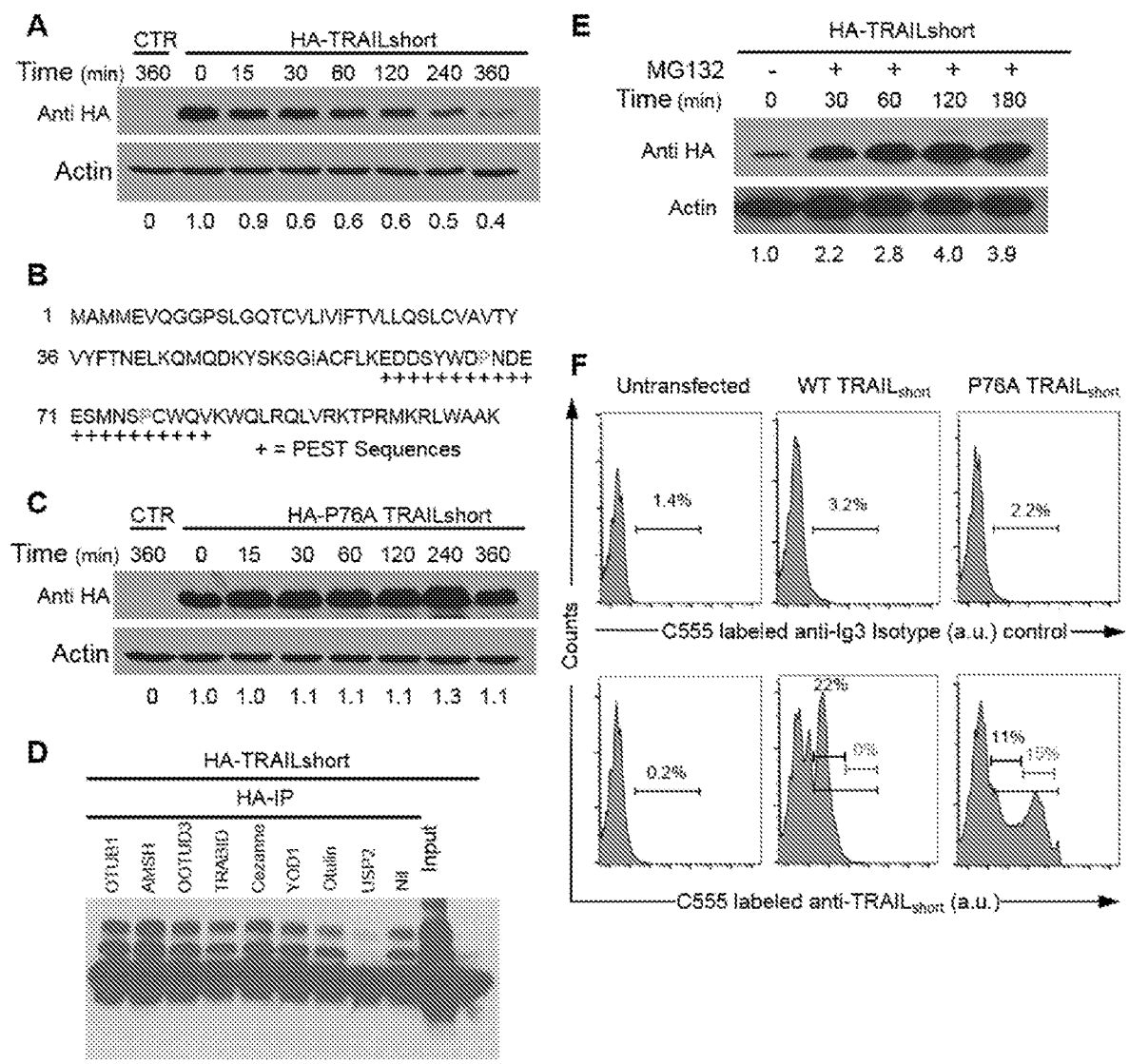
FIG. 6 shows that TRAILshort contains a PEST domain and is ubiquitinated and degraded by the proteasome. A) 293T cells were transfected with N-terminal HA-tagged TRAILshort, treated with cycloheximide (100 µg/mL) and analyzed at the times indicated by western analysis with an anti-HA antibody. B) Putative PEST domains in TRAILshort are indicated by "+" below the peptide sequence of TRAILshort. C) A proline 76 to alanine (P76A) mutation was engineered into the PEST domain of TRAILshort and cells were transfected and analyzed in the presences of cycloheximide as in (A). D) HA-tagged TRAILshort was transfected into 293T cells and immunoprecipitated with anti-HA antibody, then immunoprecipitates were treated with various de-ubiquitinating enzymes (DUBs) that distinguish between Lys48 and Lys63 ubiquitin linkages (OTUB1, AMSH, OOTUD3, TRABID, OTUD7B, YOD1, Otulin, or USP2). The treated samples were separated by SDS-PAGE then immunoblotted for ubiquitin. E) 293T cells transfected with TRAILshort were incubated in the presence of MG132 for the times indicated, then harvested and analyzed by western with anti-TRAILshort. F) TRAILshort expression is increased in the P76A mutant. TRAILshort and P76A TRAILshort were transfected into 293T cells and analyzed by flow cytometry for TRAILshort (bottom panels) or with an isotype control antibody (top panels). All data are representative of at least three independent experiments.

TRAILshort Contains a PEST Domain and is Ubiquitinated and Degraded by the Proteasome During studies examining the subcellular localization of TRAILshort (FIG. 1A) a seemingly short half-life for TRAILshort was noted. To examine this observation, 293T cells were transfected with HA-TRAILshort and evaluated the protein half-life in the absence and presence of the protein synthesis inhibitor cycloheximide (FIG. 6A). ~50% of the protein was lost within the first ~60 minutes, indicating a rapid protein turnover. A putative PEST domain in TRAILshort was identified between amino acids 59 and 81 (FIG. 6B). The substitution of Proline 76 to Alanine markedly prolonged the half-life of TRAILshort (FIG. 6C), confirming a functional PEST domain and suggesting subsequent ubiquitinaton and proteasome mediated degradation.

To verify that TRAILshort is ubiquitinated, HA-tagged TRAILshort was expressed in 293T cells and anti-HA pulldowns and immunoblotting for ubiquitin were performed. These analyses revealed an abundance of ubiquitinated proteins migrating at sizes corresponding to polyubiquitinated HA-TRAILshort (FIG. 4D). Modification of proteins with ubiquitin at their Lys48 linkages can drive proteasome degradation, whereas ubiquitination at Lys63 linkages results in modified protein:protein interactions and alteration of signal transduction pathways (Deng et al., 2000 Cell 103:351-361). To assess whether ubiquitinated TRAILshort is targeted for degradation via Lys48, specific de-ubiquitinating enzymes (DUBs) that distinguish between Lys48 and Lys63 ubiquitin linkages were used (see, e.g., Komander et al., 2009 Nat Rev Mol Cell Biol 10:550-563). Ubiquitination of HA-TRAILshort was reversed by the Lys48-specific DUB USP2 (FIG. 6D), indicating that TRAILshort is ubiquitinated in a manner that is consistent with it being targeted to the proteasome for degradation. This was confirmed by measuring TRAILshort levels in cells treated with or without the proteasome inhibitor MG132, revealing that proteasome inhibition greatly increases TRAILshort expression levels (FIG. 6E). Consistent with these observations and with the hypothesis that the ubiquitin proteasome pathway is governing expression levels of TRAILshort, expression of the PEST mutant P76A TRAILshort resulted in increased levels of TRAILshort on individual cells; the total number of cells containing TRAILshort did not increase appreciably (FIG. 6F).

TRAILshort is Both Sufficient and Necessary to Cause TRAIL Resistance

Figure 7:
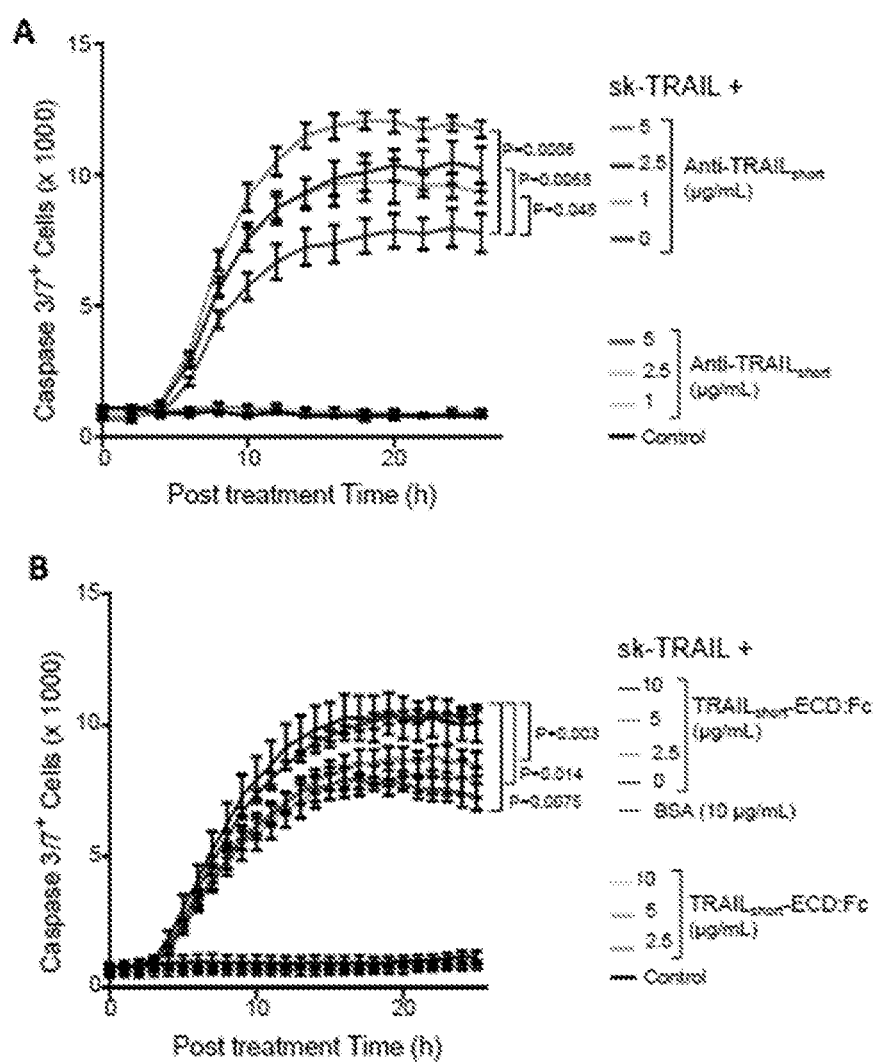
FIG. 7 shows that TRAILshort is both necessary and sufficient to cause TRAIL resistance. A) Jurkat T cells, which constitutively express TRAILshort, were induced to die by the addition of sk-TRAIL, in the presence or absence of increasing amounts of anti-TRAILshort antibody. Cell death was measured by active caspase 3 staining. Control cells were treated with increasing anti-TRAIL$_{short}$ antibody alone. At the far right time point the top four traces are, from top to bottom, 5 µg/mL anti-TRAILshort, 2.5 µg/mL anti-TRAILshort, 1 µg/mL anti-TRAILshort, and 0 µg/mL anti-TRAILshort. B) HeLa cells, which do not express TRAILshort, were stimulated to die by the addition of sk-TRAIL in the absence or presence of increasing amounts of a fusion protein consisting of the extracellular domain of TRAILshort fused to Fc (Ts-ECD:Fc) or with bovine serum albumin (BSA) control and analyzed as in (A). Additional control cells were treated with increasing TRAILshort-ECD:Fc alone. At the far right time point the top five traces are, from top to bottom, 0 µg/mL anti-TRAILshort-ECD:Fc, 10 µg/mL BSA, 5 µg/mL anti-TRAILshort-ECD:Fc, 2.5 µg/mL anti-TRAILshort-ECD:Fc, and 10 µg/mL anti-TRAILshort-ECD:Fc. Data are representative of six independent experiments.

These data indicate that TRAILshort fundamentally impacts cell death/survival, both of the cell that produces TRAILshort as well as of bystander cells that uptake TRAILshort from microvesicle mediated transfer. To assess whether TRAILshort alone is responsible for these effects, a recombinant construct of TRAILshort was generated by cloning the extracellular domain of TRAILshort fused to the Fc domain of immunoglobulin G. Following purification, recombinant TRAILshort extracellular domain:Fc fusion (TRAILshortECD:Fc) was added to Jurkat T cells alone or to Jurkat T cells pretreated with sk-TRAIL. While TRAILshortECD:Fc was not toxic, it did prevent sk-TRAIL mediated killing of Jurkat T cells in a dose dependent manner (FIG. 7A).

Whether depletion of TRAILshort is sufficient to mitigate TRAIL resistance was assessed. The generation of TRAILshort antibodies that are specific to the 11 C terminal amino acids unique to TRAILshort is described elsewhere (see, e.g., Schnepple et al., 2011 J Biol Chem 286:35742-35754). Jurkat T cells which constitutively express TRAILshort were stimulated with IFNα14 to induce maximal TRAILshort expression and then induced to die by sk-TRAIL. Consistent with our prior observations, sk-TRAIL treatment resulted in robust killing of the Jurkat T cells (FIG. 7B). Congruent with TRAILshort being an antagonist of TRAIL, sk-TRAIL treatment in the presence of increasing doses of TRAILshort antibody induced a dose dependent increase in Jurkat killing, which at the highest dose of antibody tested of 5 µg/ml, effectively doubled the number of dead cells despite the TRAILshort antibody alone having no intrinsic cytotoxicity. Altogether therefore in this model system the presence of TRAILshort is both necessary and sufficient for TRAIL resistance, and our data indicate that the anti-TRAIL effects of TRAILshort can be effectively inhibited by TRAILshort specific antibody.

Example 2: TRAILshort Reduces the Cytotoxic Capacity of NK Cells

NK cells play a key role in the antiviral response to HIV infection. While NK cells can produce TRAIL as an effector molecule to kill tumor cells, its role in antiviral defense is just emerging. TRAILshort produced by HIV infected cells may be a major factor in reducing the ability of these cells to mount a significant innate immune response to the virus. To determine the effect of TRAILshort on NK function, the role of TRAILshort in the reduced cytotoxic function of NK cells during HIV infection was evaluated.

Methods

Jurkat cells were transfected with a control or TRAILshort expressing plasmids, and incubated with primary NK cells from uninfected donors (N=10) at various Effector:Target ratios (1:1 to 20:1). A flow cytometric-based assay was used to determine the cytotoxic effects of the NK cells on the target Jurkat cells. The effect of TRAILshort overexpression on NK cell activity and function was determined by staining for CD69, Perforin, CD16 and CD107a. In addition, the effect of gp120, or supernatant containing HIV-1 IIIB strain on NK expression of TRAIL and TRAILshort was measured by surface staining.

Results

Figure 8:
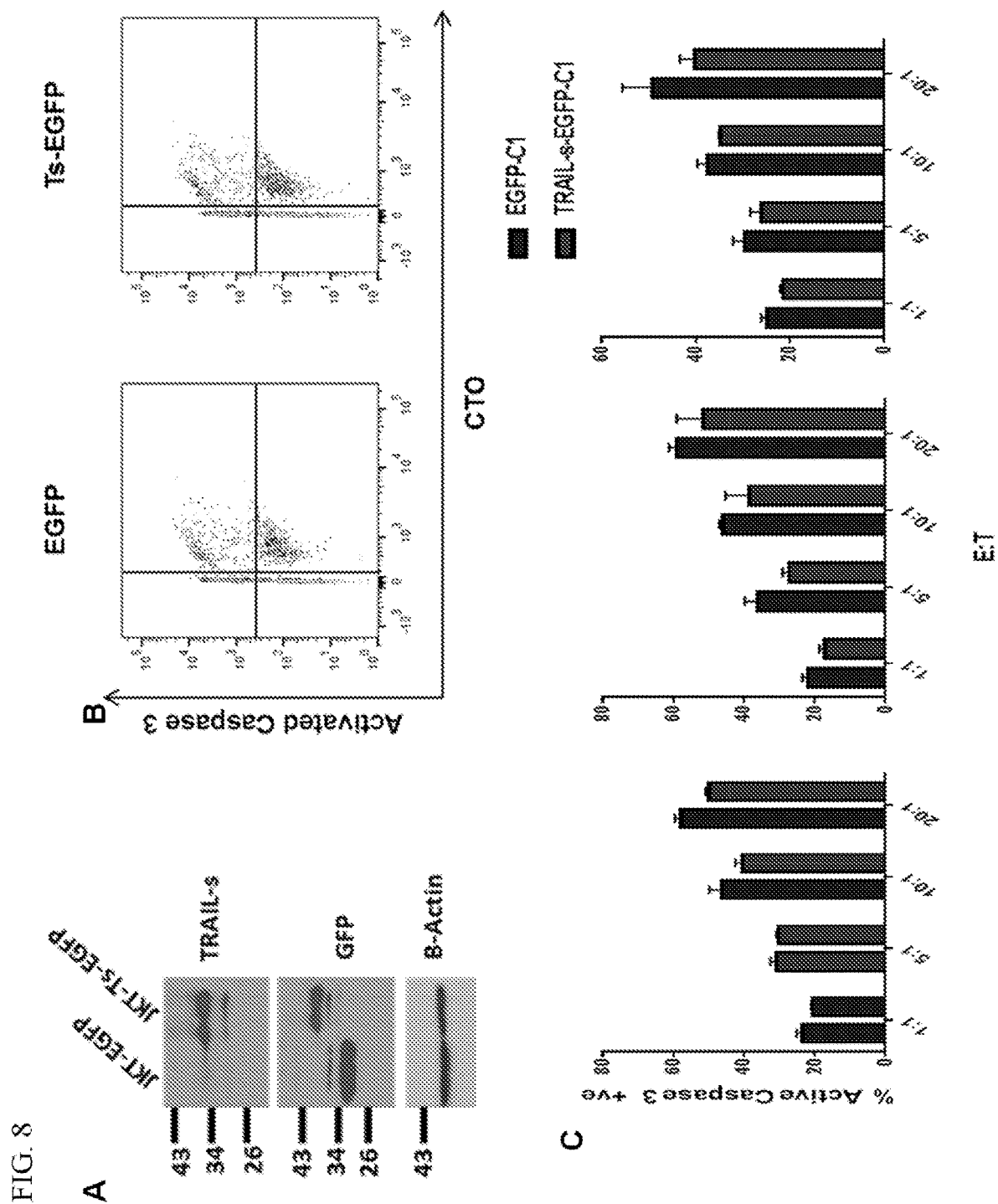
FIG. 8 shows that overexpression of TRAILshort reduces the cytotoxicity of NK cells. A) A western blot shows overexpression of TRAILshort-EGFP-C1 in Jurkat cells. B) NK cells were co-cultured with Jurkat cells labelled with CTO and were stained for activated caspase –3. C) Cytotoxicity assays were performed with Jurkat cells in the presence of TRAILshort or control plasmid with increasing E:Tt ratios. EGFP-C1 is on the left and TRAILshort-EGFP-C1 is on the right in every instance.

Overexpression of TRAILshort in target cells significantly reduced the cytotoxic function of NK against these cells across a range of E:T ratios compared to the control cells (FIG. 8; p=0.006 at an E:T ratio of 20:1). These results demonstrated that TRAILshort expression significantly reduces NK mediated cytotoxicity.

Figure 9:
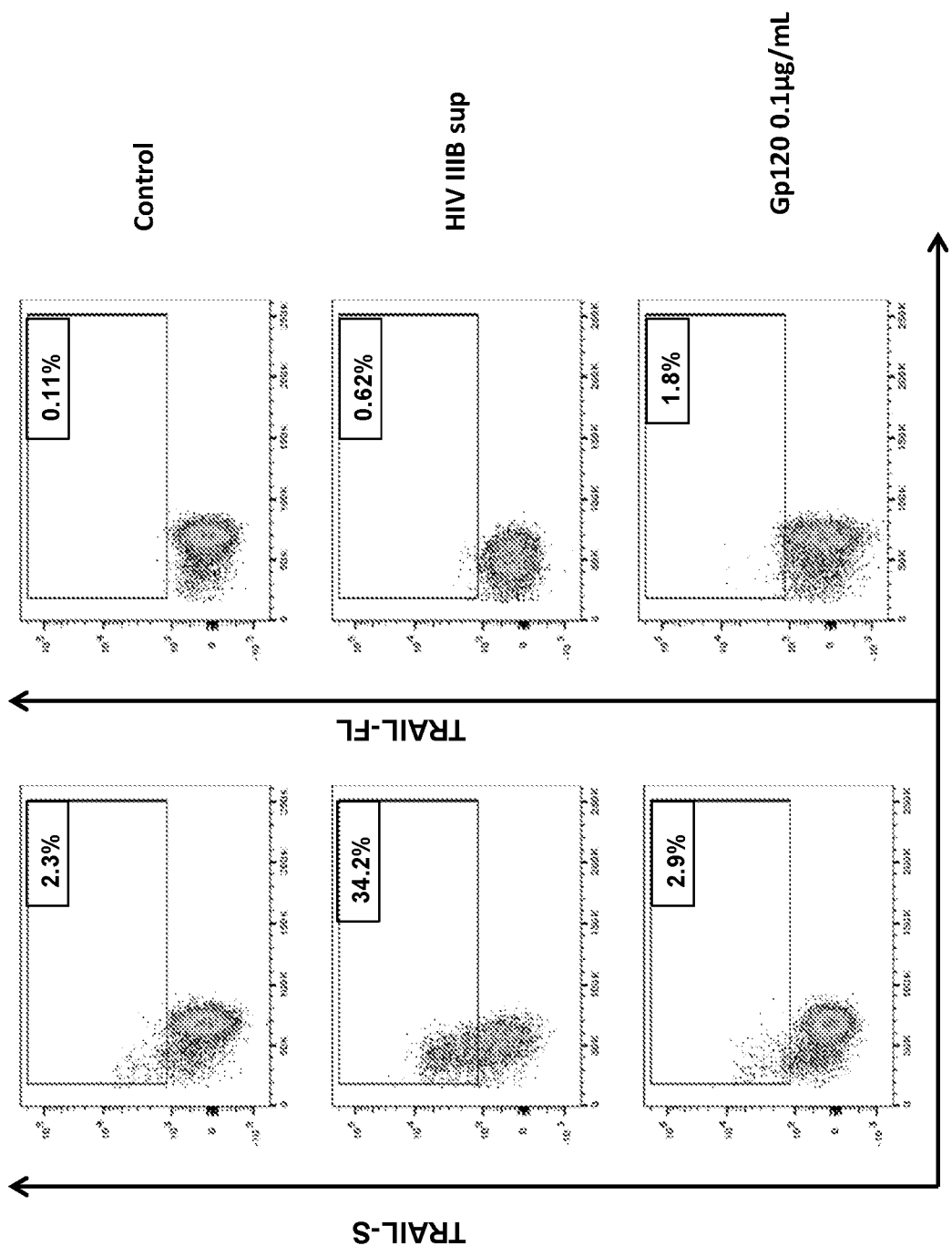
FIG. 9 contains flow cytometry shows that HIV IIIB induces surface expression of TRAILshort in NK cells. NK cells were incubated with culture supernatants containing HIV IIB virus or Gp120 recombinant protein and were stained for surface expression of TRAILshort and TRAIL$_{FL}$.

Pre-treatment of NK cells with culture supernatant containing HIV IIIB virus caused a large increase in surface expression of TRAILshort, yet had no effect on TRAIL expression, whereas gp120 alone did not (FIG. 9). These results demonstrated that HIV containing supernatant alone increases the surface expression of TRAILshort on NK cells.

Figure 10:
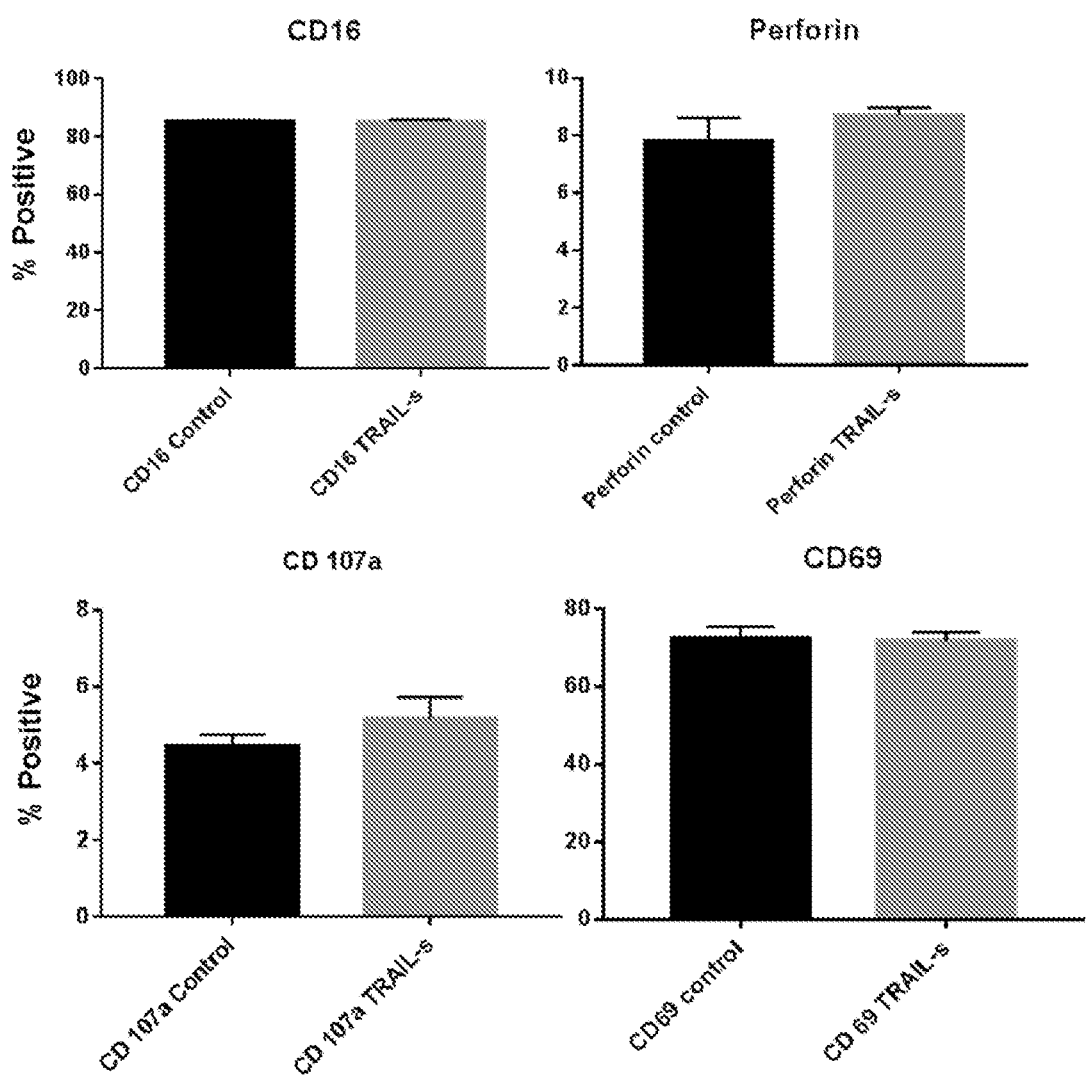
FIG. 10 contains graphs showing that TRAILshort does not affect NK activation. NK cells were co-cultured with Jurkat cells overexpressing TRAILshort (grey bars), isolated and stained for CD16, Perforin, CD107, and CD69.

TRAILshort did not alter the expression of CD69, CD16, Perforin or CD107a in NK cells (FIG. 10). These results demonstrated that TRAILshort affects NK function, and can play an important role in the innate immune response to HIV infection.

Example 3: Humanization of Anti-TRAILshort Antibodies

Murine monoclonal antibody TRAILs 2.2 was humanized to create antibody Ab866.

Heavy Chain

The sequence of the VH domain of murine TRAILs 2.2 is set forth below, with the CDRs indicated in bold type:

(SEQ ID NO: 27)
MGWSWIILFLLSGTAGVHCQVQLQQSGPELVKPGASVKISCKASGYIFTN
NDMNWVKQRPGQGLEWIGGIDPGDGRTKYNEKFKGKATLTADKFSNTVYM
QLSSLTSENSAVYFCGRGGYEFGIDYWGQGTSVTVSSATTTAPSVYPLA.

The CDRs of the murine VH were grafted into human acceptor frameworks to create humanized variants VH1-VH4:

VH1:
(SEQ ID NO: 5)
QVQLVQSGAEVKKPGATVKISCKVSGYIFTNNDMNWVQQAPGKGLEWMGG
IDPGDGRTKYNEKFKGRVTITADESTSTAYMELSSLRSEDTAVYYCGRGG
YEFGIDYWGQGTLVTVSS;

VH2:
(SEQ ID NO: 6)
QVQLVQSGAEVKKPGASVKVSCKASGYIFTNNDMNWVRQAPGQGLEWMGG
IDPGDGRTKYNEKFKGRVTMTRDTSTNTVYMELSSLTSEDTAVYFCGRGG
YEFGIDYWGQGTTVTVSS;

VH3:
(SEQ ID NO: 7)
QVQLVQSGAEVKKPGSSVKVSCKSSGYIFTNNDMNWVRQAPGQGLDWMGG
IDPGDGRTKYNEKFKGRVTISADIFSNTAYMELNSLTSEDTAVYFCGRGG
YEFGIDYWGQGTTVTVSS;
and VH4:
(SEQ ID NO: 8)
QVQLVESGAEVKKPGASVKVSCKVSGYIFTNNDMNWVRQAPGEGLEWMGG
IDPGDGRTKYNEKFKGRVTMTEDTSTDTAYMELSSLRSEDTAVYYCGRGG
YEFGIDYWGQGTTVTVSS.

An alignment of the VH0 murine sequence the humanized variants VH1-4 is shown in FIG. 12A. The homology of humanized variants VH1-4 to the VH0 murine sequence is shown in Table 1 below.

TABLE 1

| Humanized variants homology to murine VH. | | |
|---|---|---|
|  | Identical amino acids | Consensus amino acids |
| VH1 | 79.7% | 86.4% |
| VH2 | 83.9% | 91.5% |

TABLE 1-continued

| Humanized variants homology to murine VH. | | |
|---|---|---|
|  | Identical amino acids | Consensus amino acids |
| VH3 | 81.4% | 91.5% |
| VH4 | 78.0% | 86.4% |

Light Chain

The sequence of the VL domain of murine TRAILs 2.2 is set forth below, with the CDRs indicated in bold type:

(SEQ ID NO: 28)
MVLMSLLFWVSGTCGDIVMTQSPSSLSVSAGEKVTMSCKSSQSLLNSGNQ
KNSLAWYQQKPGRPPTLLISGASTRESGVPDRFTGSGSGTDFTLTISSVQ
AEDLAVYYCQNDHSFPLTFGAGTKLELKRADAAPTVSIFPPSSEQLTSGG
ASVVCFLNNFYPK.

The CDRs of the murine VL were grafted into human acceptor frameworks to create humanized variants VL1-VL4:

VL1:
(SEQ ID NO: 18)
DVVMTQSPDSLAVSLGERATINCKSSQSLLNSGNQKNSLAWYQQKPGQPP
KLLIYGASTRESGVPDRFSGSGSGTDFTLTISSLQAEDVAVYYCQNDHSF
PLTFGQGTKLEIK;

VL2:
(SEQ ID NO: 19)
DIVMTQSPDSLAVSLGERATINCKSSQSLLNSGNQKNSLAWYQQKPGQPP
KLLIYGASTRESGVPDRFSGSGSGTDFTLTISSLQAEDVAVYYCQNDHSF
PLTFGGGTKLEIK;

VL3:
(SEQ ID NO: 20)
DIVMTQSPDSLAVSLGERATINCKSSQSLLNSGNQKNSLAWYQQRPGHPP
KLLLYGASTRESGVPDRFSGSGSGTDFTLTISSLQAEDVAVYYCQNDHSF
PLTFGGGTKVEIK;
and VL4:
(SEQ ID NO: 21)
EIVLTQSPDSLAVSLGERATINCKSSQSLLNSGNQKNSLAWYQHKPGRPP
KLLIYGASTRESGVPDRFSGSGSGEDFTLTISSLQAEDVAVYYCQNDHSF
PLTFGPGTKVDLK.

An alignment of the VL0 murine sequence the humanized variants VL1-4 is shown in FIG. 12B. The homology of humanized variants VL1-4 to the VL0 murine sequence is shown in Table 2 below.

TABLE 2

| Humanized variants homology to murine VL. | | |
|---|---|---|
|  | Identical amino acids | Consensus amino acids |
| VL1 | 85.8% | 92.9% |
| VL2 | 86.7% | 93.8% |
| VL3 | 84.1% | 93.8% |
| VL4 | 83.2% | 92.0% |

All humanized variants were in accordance with World Health Organization (WHO)'s definition of humanized antibodies.

Example 4: Anti-TRAILshort Antibodies

Each of the $V_H$ domains is synthesized in-frame with a human IgG1 isotype constant domain sequence. The entire heavy chain sequence can be codon optimised (DNA2.0, USA) and the DNA sequence verified. The amino acid sequence of the IgG1 constant domain (allotype G1m17,1) is:

(SEQ ID NO: 29)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLEPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

Each of the $V_L$ domains is synthesised in-frame with a human IgK isotype constant domain sequence. The entire light chain sequence can be codon optimised (DNA2.0, USA) and the DNA sequence verified. The amino acid sequence of the IgK constant domain (allotype Km3) is:

(SEQ ID NO: 30)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

Each of the variant chains is verified by DNA sequencing analysis. The 16 humanized antibodies can include any combination of humanized variable domains as shown in Table 3.

TABLE 3

Combinations of humanized variable domains in humanized anti-TRAILshort antibodies.

| Humanized Variants | | | | |
|---|---|---|---|---|
| HC1:LC1 | HC1:LC2 | HC1:LC3 | HC1:LC4 |
| HC2:LC1 | HC2:LC2 | HC2:LC3 | HC2:LC4 |
| HC3:LC1 | HC3:LC2 | HC3:LC3 | HC3:LC4 |
| HC4:LC1 | HC4:LC2 | HC4:LC3 | HC4:LC4 |

The full amino acid sequence of each heavy and light chain is shown in FIG. 13.

Example 5: Anti-TRAILshort Antibodies for Treating Cancer

To examine the effect of anti-TRAILshort antibodies in vivo, NSG mice were injected with Jurkat T cell leukemia cells that constitutively express luciferase, and luciferase expression was determined twice weekly. For experiments shown in FIGS. 14A-C, mice were injected with 10 mg/kg of either IC antibody or anti-TRAILshort antibody clone 2.2 (e.g., murine TRAILs 2.2 as described in Example 4) on day 27. Mice were injected the 24 hours later (e.g., day 28) with anti-TRAIL receptor 2 (anti-DR5) antibody (10 mg/kg).

Figure 14:
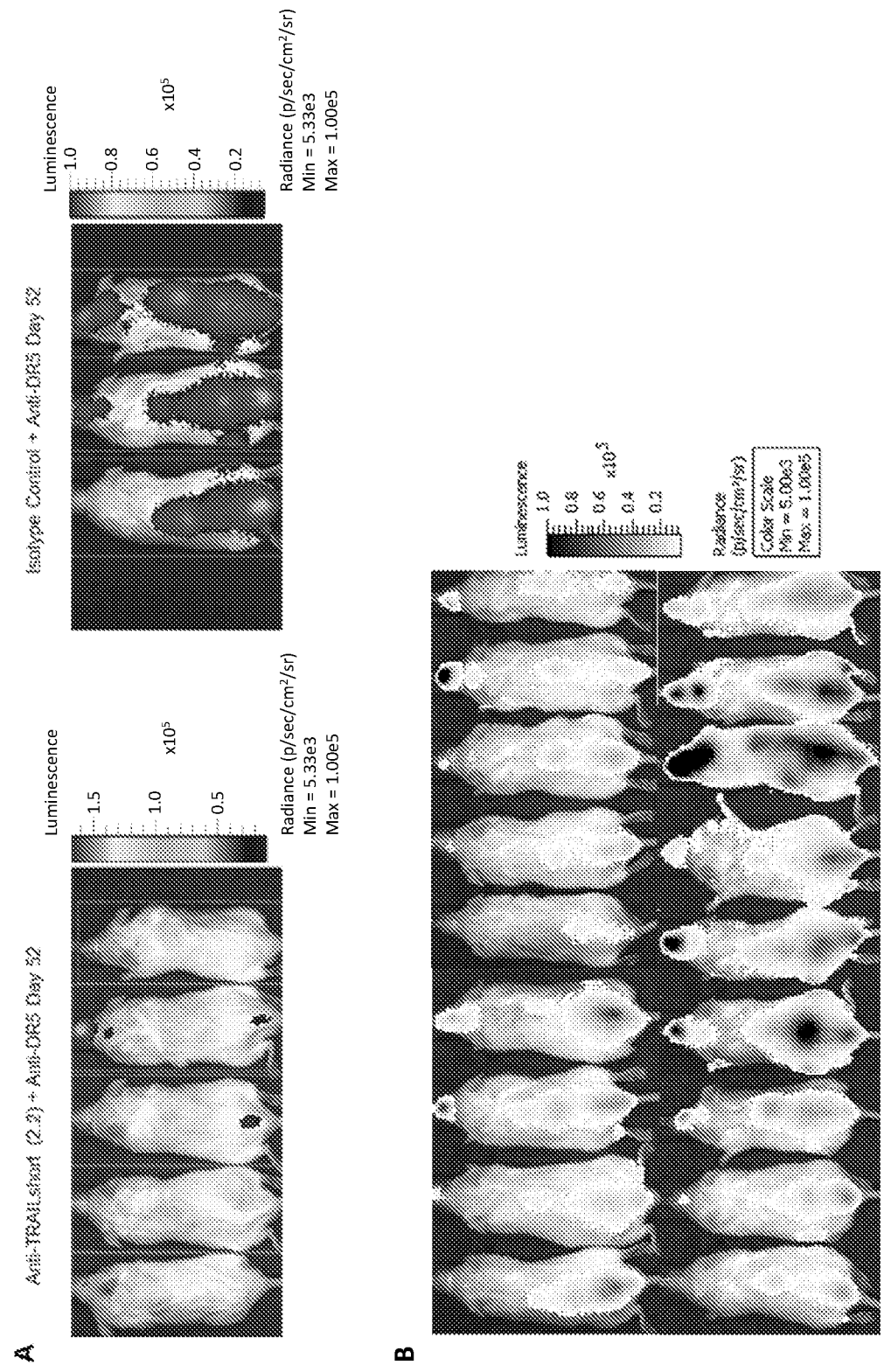
FIG. 14 shows that in vivo administration of anti-TRAILshort antibody (2.2) can reduce the number of leukemia cells and prolong survival in mice. A) Photographs showing representative luciferase expression at day 52 in mice treated on day 27 with anti-TRAILshort antibody (left panel) or isotype control (IC; right panel) and on the following day (e.g., day 28) with anti-TRAIL receptor 2 (anti-DR5) antibody. B) Photographs optimized for grayscale representation showing luciferase expression at day 45 in mice treated on day 27 with anti-TRAILshort antibody (left panel) or isotype control (IC; right panel) and on the following day (e.g., day 28) with anti-TRAIL receptor 2 (anti-DR5) antibody. C) A graph showing luciferase expression in mice treated with IC or anti-TRAILshort antibody on day 27 as indicated by the dotted lines, and treated with anti-TRAIL receptor 2 (anti-DR5) antibody on day 28 as indicated by the dashed line. D) A graph showing percent survival of mice treated with IC or anti-TRAILshort antibody on day 27 as indicated by the dotted lines and with anti-TRAIL receptor 2 (anti-DR5) antibody on day 28 as indicated by the dashed line. E) A graph showing luciferase expression in mice treated with IC or anti-TRAILshort antibody on days 20, 27, and 34 as indicated by the dotted lines. F) A graph showing percent survival of mice were treated with IC or anti-TRAILshort antibody on days 20, 27, and 34 as indicated by the dotted lines.
Figure 14:
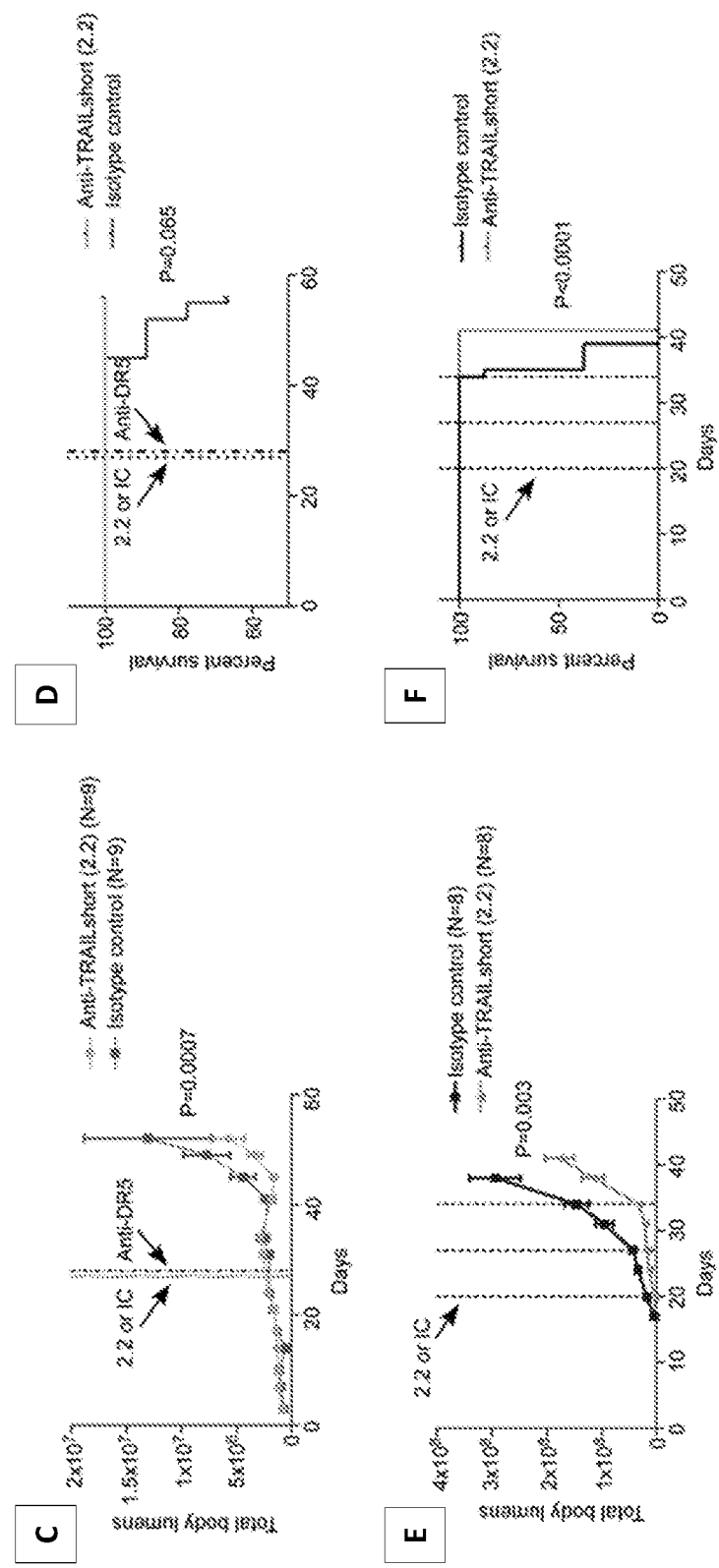

Representative luciferase expression was reduced in mice treated with anti-TRAILshort antibody relative to mice treated with isotype control (FIGS. 14A and 14B). Luciferase expression was significantly reduced in mice treated with anti-TRAILshort antibody and anti-DR5 (FIG. 14C). Although mice treated with anti-TRAILshort antibody and anti-DR5 all survived while control mice did not, this difference was not statistically significant (FIG. 14D). These results show that TRAILshort inhibition in the presence of a TRAIL agonist (anti-DR5) results in improved tumor control and improved survival compared to isotype control plus anti-DR5. For experiments shown in FIGS. 14D-E, mice were injected with 10 mg/kg of either IC antibody or anti-TRAILshort antibody clone 2.2 on days 20, 27, and 34. Luciferase expression was significantly reduced in mice treated with anti-TRAILshort antibody (FIG. 14E), and survival was significantly increased in mice treated with anti-TRAILshort antibody (FIG. 14F), compared to mice treated with isotype control antibody. These results demonstrated that in vivo administration of anti-TRAILshort antibody, alone or in the presence of anti-DR5, can reduce the number of leukemia cells in mice and prolong survival of the mice.

Figure 15:
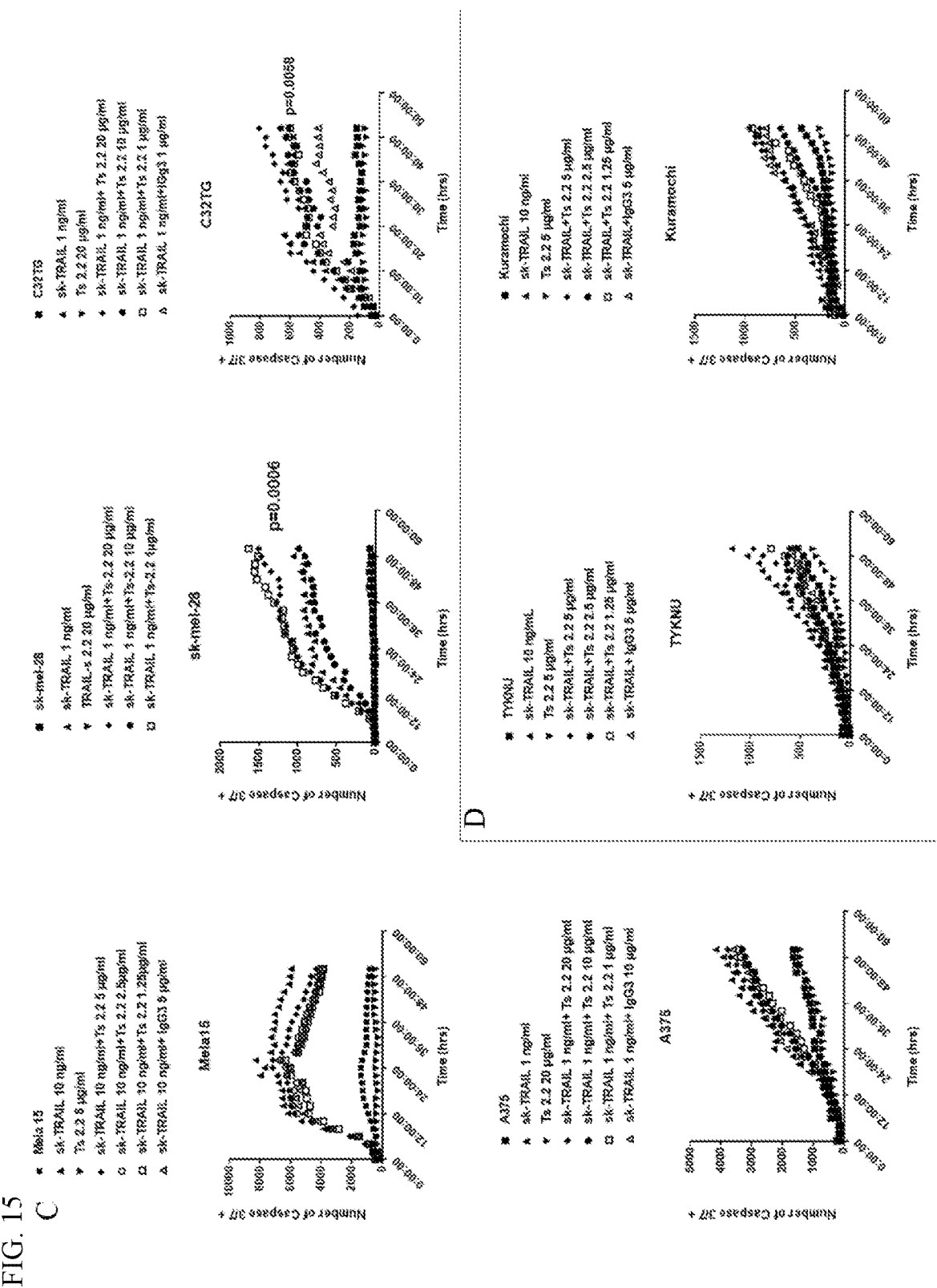
FIG. 15 contains graphs showing the effect of anti-TRAILshort antibody on sk-TRAIL cytotoxicity in different cancer cell lines. Cancer cells were pre-incubated with anti-TRAIL short antibody 2.2 (Ts 2.2) or IgG3 control, and then sk-TRAIL was added to the cells. Cell death (Caspase 3/7+) was measured over time in A) Jeko and HBL1 lymphoma leukemia cells, B) L 3.6, BxPc3, and Miapaca pancreatic cancer cells, C) MeLa 15, sk-mel-28, C32TG, and A375 melanoma cells, and D) TYKNU, Kuramochi, hOvtax2, CaOv3, COV362, PEO1, OVCARS, and Ovcar8 ovarian cancer cells. When shown, p values are with reference to sk-TRAIL alone versus sk-TRAIL with the addition of the anti-TRAIL short antibody 2.2.
Figure 15D:
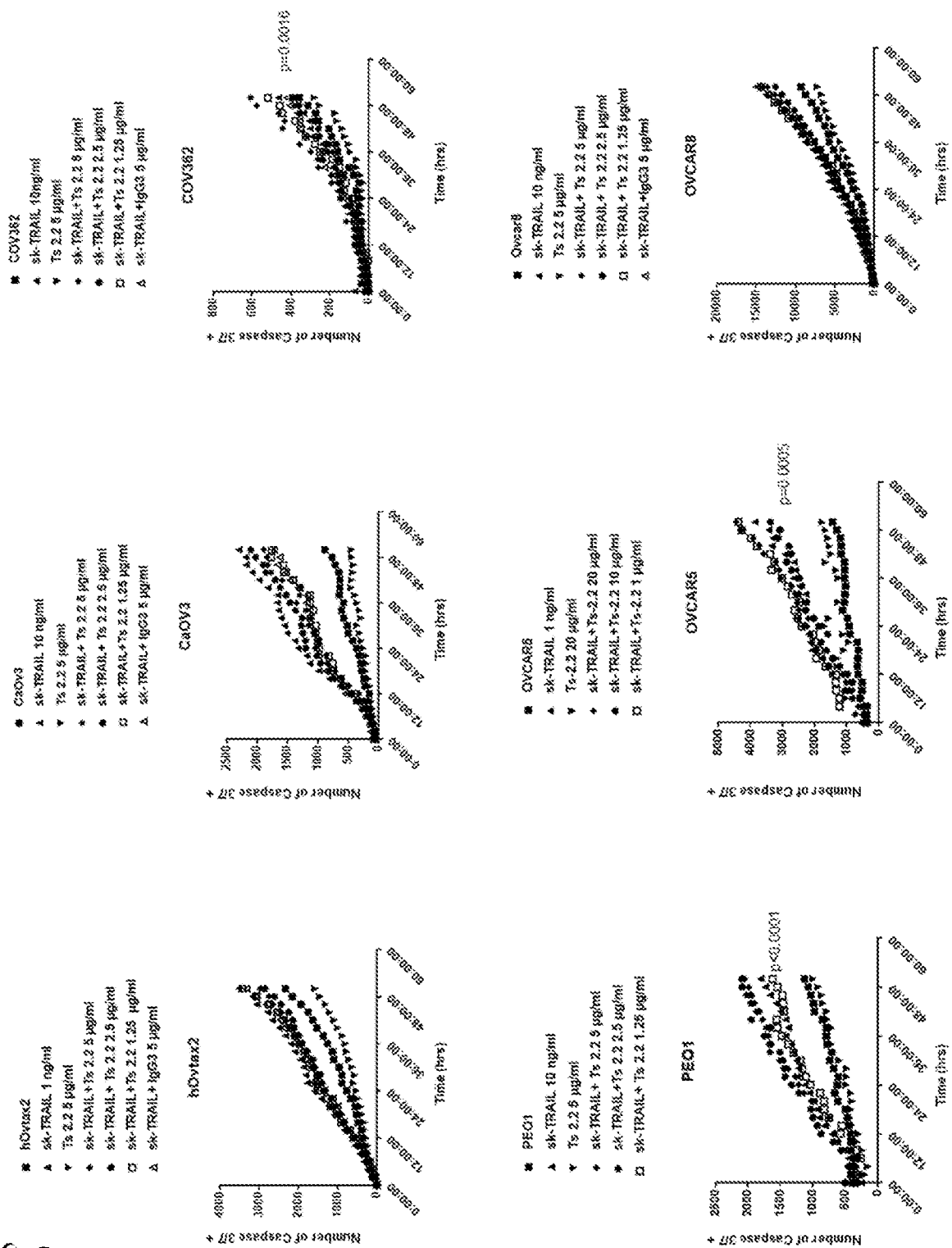

The effect of anti-TRAILshort antibodies sk-TRAIL cytotoxicity was examined in different cancer cell lines. Cells were seeded in 96 well plate at a density of $1 \times 10^4$ cells per well. Cells were then pre-incubated with the neutralizing anti-TRAIL short antibody clone 2.2 or with IgG3 control at variable concentrations (1-20 µg/mL) as indicated for one hour at 37° C. Sk-TRAIL was then added to the cells at a dose of 1-10 ng/mL as indicated. To measure cell death, Caspase 3/7 apoptosis assay reagent was added to the cells at a dilution of 1:1000. For live time analysis of cell death, the IncuCyte® system was used to capture real time images of the cells every 2 hours. Lymphoma leukemia cells (FIG. 15A), pancreatic cancer cells (FIG. 15B), melanoma cells (FIG. 15C), and ovarian cancer cells (FIG. 15D) were examined. Each treatment was done in triplicate. These results demonstrated that, in some cell lines, anti-TRAILshort antibodies act in concert with recombinant TRAIL to induce apoptosis in the cancer cells.

TABLE 4

The effect of anti-TRAILshort antibody in different human cancer cell lines.

| Cell Type | Number of Cell Lines Tested | Names of Cell Lines | Number Responsive to Anti-TRAILshort 2.2 |
|---|---|---|---|
| Blood Diseases (Lymphoma and Leukemia) | 9 | HBL-1*, Jurkat*, Jeko1*, OCI-LY3, NALM-6, MEC-1, RPMI8226, BCWM and MWCL | 3 |
| Ovarian Carcinoma | 8 | Cov362*, PEO1*, OVCar5 *Caov-3, TYK-nu, OVCar8, Kuramochi, and Ovca420 | 3 |
| Melanomas | 3 | SK-MEL-28*, C32TG*, and A375 | 2 |
| Cholangiocarcinoma | 2 | KMCH-1*, Mz-Ch1 | 1 |
| Pancreatic Cancer | 3 | L3.6pl*, Miapaca and BxPC3 | 1 |
| Renal Cell Carcinoma | 1 | A498 | 0 |

TABLE 4-continued

The effect of anti-TRAILshort antibody in different human cancer cell lines.

| Cell Type | Number of Cell Lines Tested | Names of Cell Lines | Number Responsive to Anti-TRAILshort 2.2 |
|---|---|---|---|
| Hepatocellular Carcinoma | 2 | HepG2 and HLE | 0 |
| Mesothelioma | 1 | H2596 | 0 |
| Triple Negative Breast Cancer | 1 | MDA-MB-231 | 0 |

Figure 16:
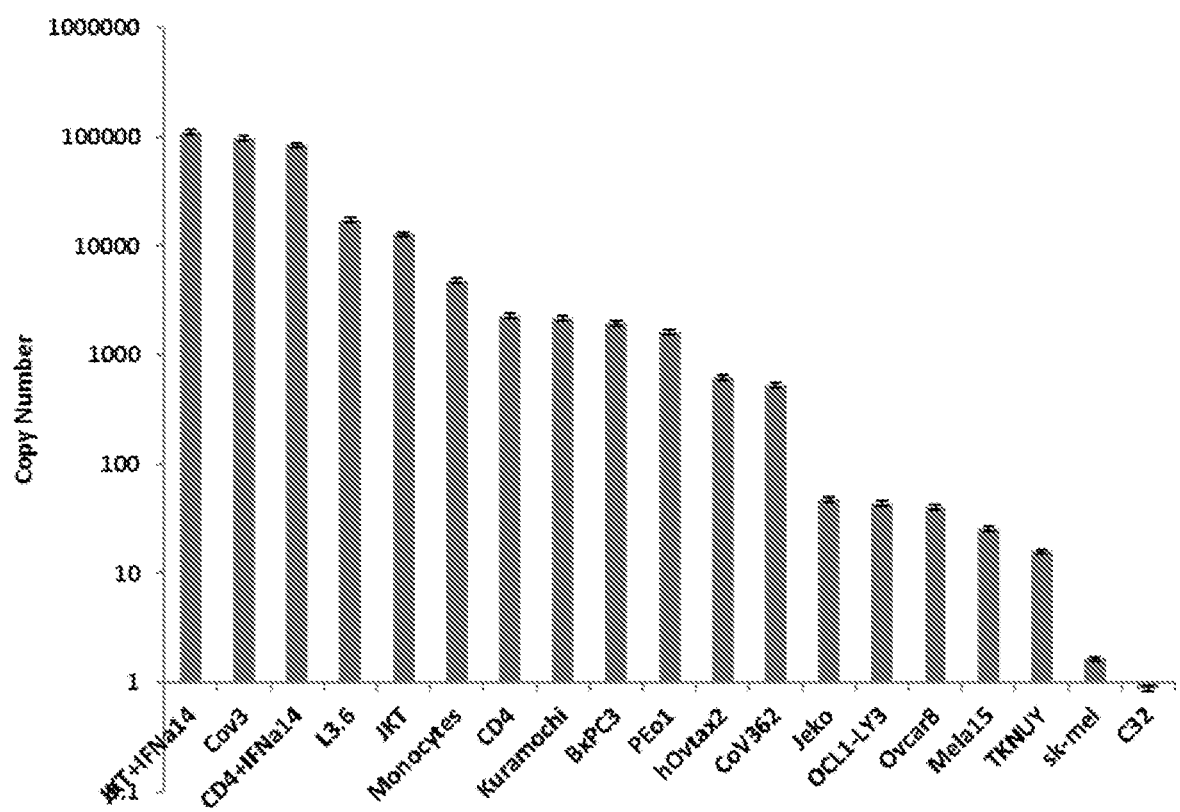
FIG. 16 contains a graph showing quantification of TRAILshort (TRAIL-s) mRNA in different cancer cells. qRTPCR was used to calculate the number of copies of TRAIL-s using TRAIL-s standards.

*Cell lines responsive to anti-TRAILshort antibody, either alone or in combination with sk-TRAIL To examine TRAIL expression in the different cancer cells, TRAIL mRNA was quantified in different cancer cells by qRTPCR. RNA was isolated using the RNeasy mini-kit from Qiagen. 1 μg of RNA was reverse transcribed to cDNA using a high capacity cDNA reverse transcription kit. cDNA was diluted and, using standards for TRAILshort and TRAIL$_{FL}$, the number of copies for each gene was calculated in lymphoma leukemia cells, pancreatic cancer cells, melanoma cells, and ovarian cancer cells (FIG. 16).

Figure 17:
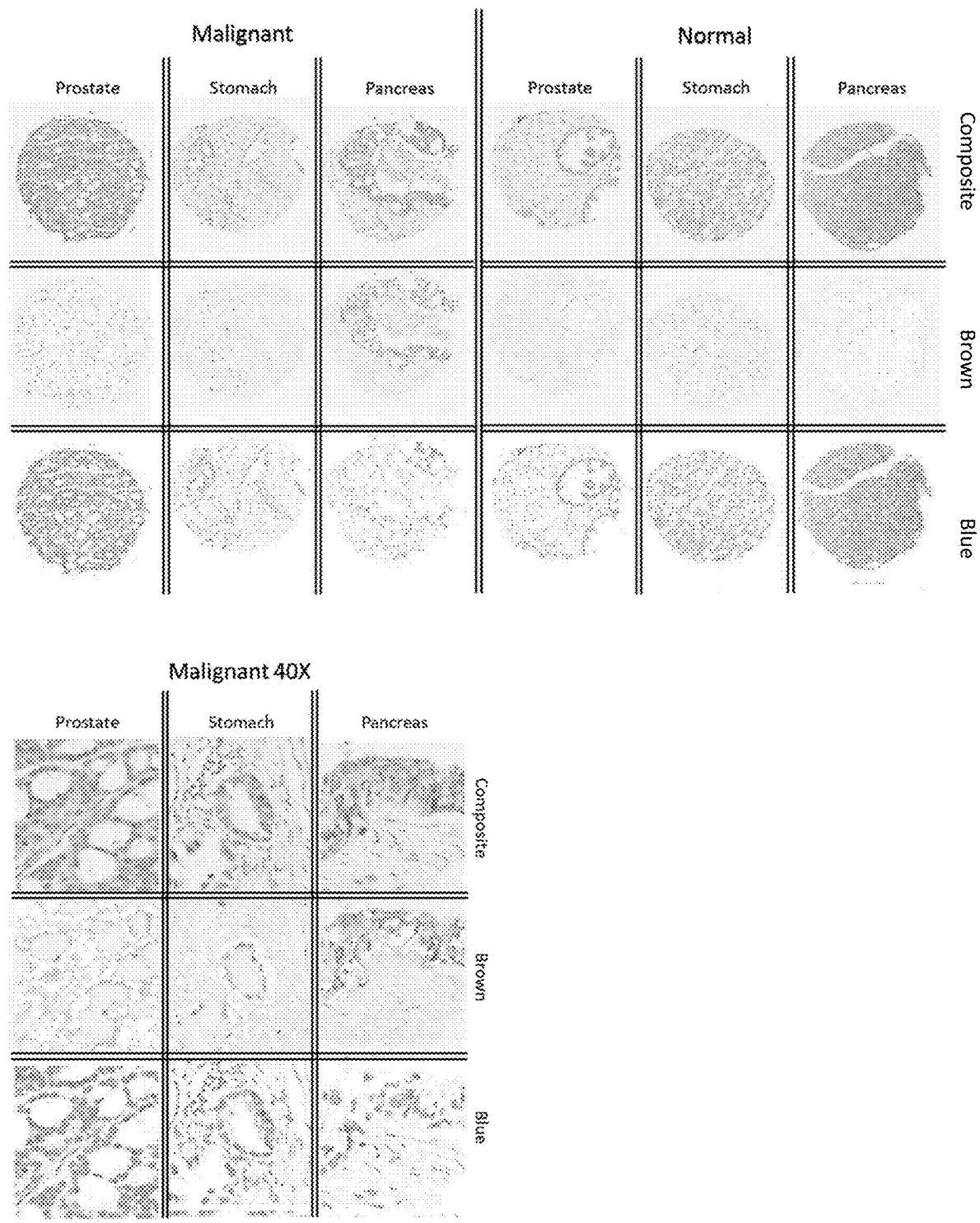
FIG. 17 contains immunohistochemistry images showing tissues stained using the TRAILshort 2.2 antibody. Shown are examples of normal and corresponding cancer tissues stained positive for TRAILshort (top panel). 40× magnification of malignant samples are also shown (bottom panel).

To further examine TRAIL expression in the different cancer cells, tissues from a tissue microarray were stained by immunohistochemistry using the TRAILshort 2.2 antibody at a concentration of 1:400. As shown in FIG. 17, examples of normal and corresponding cancer tissues from the pancreas, stomach, and prostate stained positive for TRAILshort. These results demonstrated that cancer tissues have significantly elevated expression of TRAILshort compared to non-malignant tissues.

Example 6: Anti-TRAILshort Antibodies for Treating Cancer

TRAILshort expression in a variety of cancer types was observed using immunohistochemistry of tissue microarrays. 8 Tissue Microarrays (TMA) done using the anti-TRAIL-short antibody 2.2 at a dilution of 1:400 are summarized in FIG. 18 and in Table 5 below.

TABLE 5

TRAILshort expression observed in immunohistochemistry of tissue microarrays.

| Percent Positive cells for TRAIL-s | Degree of staining | IRS |
|---|---|---|
| Pancreas | | |
| Number of Positive cases | 7/20 | 35% |
| 4 | 2 | 8 |
| 4 | 1 | 4 |
| 4 | 2 | 8 |
| 3 | 2 | 6 |
| 1 | 2 | 2 |
| 1 | 2 | 2 |
| 1 | 1 | 1 |
| Stomach | | |
| Number of Positive cases | 6/20 | 30% |
| 3 | 2 | 6 |
| 2 | 2 | 4 |
| 1 | 2 | 2 |
| 1 | 1 | 1 |
| 1 | 1 | 1 |
| 1 | 1 | 1 |
| Prostate | | |
| Number of Positive cases | 2/20 | 10% |
| 1 | 2 | 2 |
| 1 | 2 | 2 |
| Breast | | |
| Number of Positive cases | 5/20 | 25% |
| 1 | 1 | 1 |
| 1 | 2 | 2 |
| 1 | 3 | 3 |
| 1 | 1 | 1 |
| 1 | 2 | 2 |
| Cervix | | |
| Number of Positive cases | 5/20 | 25% |
| 1 | 1 | 1 |
| 1 | 2 | 2 |
| 1 | 2 | 2 |
| 1 | 2 | 2 |
| 1 | 2 | 2 |
| Lung | | |
| Number of Positive cases | 3/20 | 15% |
| 1 | 2 | 2 |
| 1 | 2 | 2 |
| 1 | 2 | 2 |
| Head and neck | | |
| Number of Positive cases | 2/20 | 10% |
| 1 | 3 | 3 |
| 1 | 2 | 2 |
| Kidney | | |
| Number of Positive cases | 2/20 | 10% |
| 1 | 1 | 1 |
| 1 | 1 | 1 |
| Liver | | |
| Number of Positive cases | 2/20 | 10% |
| 1 | 1 | 1 |
| 1 | 1 | 1 |
| Lymph node | | |
| Number of Positive cases | 1/20 | 5% |
| 1 | 2 | 2 |
| Bladder | | |
| Number of Positive cases | 1/20 | 5% |
| 1 | 1 | 1 |
| Soft tissue | | |
| Number of Positive cases | 1/20 | 5% |
| 1 | 1 | 1 |
| Ovary | | |
| Number of Positive cases | 1/20 | 5% |
| 1 | 1 | 1 |
| Oral cavity | | |
| Number of Positive cases | 1/20 | 5% |
| 1 | 2 | 2 |

TRAILshort was found in many human tumors (FIG. 19). TRAILshort levels were quantified as reads per kilobase million (RPKM). Data were determined from the Cancer Genome Atlas (TCGA).

Increasing levels of TRAILshort were associated with worse survival in some human tumors (FIG. 20). Survival was assessed by Kaplan Meyer analysis for patients having diffuse large b cell lymphoma (FIG. 20A), colon and rectal adenocarcinoma (FIG. 20B), chromophobe renal cell carcinoma (FIG. 20C), pancreatic adenocarcinoma (FIG. 20D), and thymoma (FIG. 20E), and was stratified by TRAILshort level expressed as transcripts per kilobase million (TPM). Survival curves were determined from the Cancer Genome Atlas (TCGA).

Figure 21:
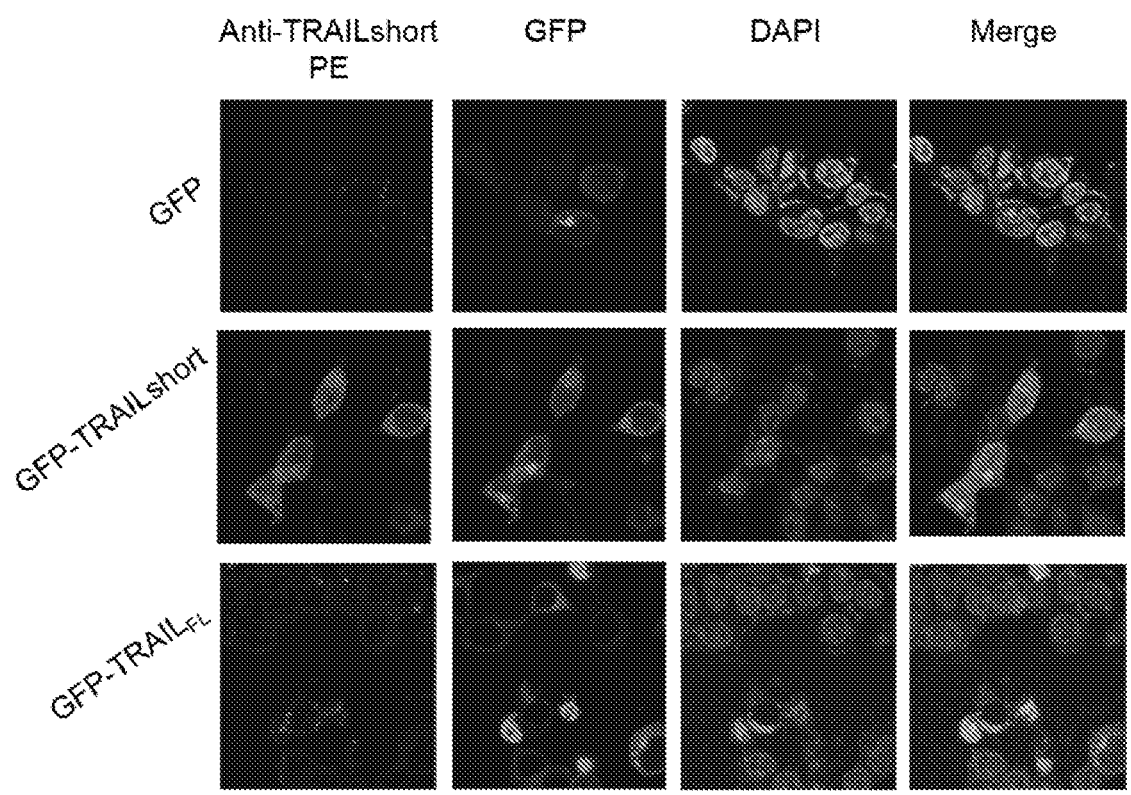

Anti-TRAILshort antibody interacted with TRAILshort antigen. HEK293T cells were transfected with plasmids encoding green fluorescent protein (GFP), GFP-TRAILshort, or GFP-TRAIL$_{FL}$, and were analyzed by confocal microscopy (FIG. 21).

Codon optimization yielded 16 anti-TRAILshort antibody variants. Variants of the anti-TRAILshort antibody had varying effect on TRAIL induced cytotoxicity against Jurkat cells in combination with super killer (sk)-TRAIL and varying affinity (Table 6). Surface Plasmon resonance was used to analyze affinity. Clone HC2LC3 showed affinity of 3.8 pM, and significant synergistic killing in the presence of sk-TRAIL (1 ng/ml; FIG. 22).

TABLE 6

Effect on TRAIL induced cytotoxicity and affinity of codon optimized anti-TRAILshort antibodies.

| Antibody | Effect on sk-TRAIL Cytotoxicity in Jurkats | KD (Affinity by SPR) |
|---|---|---|
| HC0LC0 | Increased cytotoxicity significantly | 3 pM |
| HC1LC1 | Slightly increased cytotoxicity | 34 pM |
| HC1LC2 | No effect on cytotoxicity | 14 pM |
| HC1LC3 | No effect on cytotoxicity | 10 pM |
| HC1LC4 | No effect on cytotoxicity | 38 pM |
| HC2LC1 | No effect on cytotoxicity | 25 pM |
| HC2LC2 | No effect on cytotoxicity | 3 pM |
| HC2LC3 | Increased cytotoxicity significantly(in all 4 independent experiments) | 3.8 pM |
| HC2LC4 | No effect on cytotoxicity | 7.8 pM |
| HC3LC1 | No effect on cytotoxicity | 11 pM |
| HC3LC2 | No effect on cytotoxicity | 3 pM |
| HC3LC3 | No effect on cytotoxicity | 4.5 pM |
| HC3LC4 | No effect on cytotoxicity | 11 pM |
| HC4LC1 | No effect on cytotoxicity | 140 pM |
| HC4LC2 | No effect on cytotoxicity | 46 pM |
| HC4LC3 | No effect on cytotoxicity | 31 pM |
| HC4LC4 | No effect on cytotoxicity | 330 pM |

Some patient-derived cells were responsive to anti-TRAILshort antibody plus sk-TRAIL, but that others were not. Cells from the spleens of patients undergoing splenectomy for suspected hematologic malignancy were freshly isolated and treated with nothing (control), superkiller TRAIL (sk-TRAIL, an oligomerised TRAIL agonist), humanized anti-TRAILshort antibody (clone HC2LC3), or Isotype control antibody (IgG4). Cell death over time was monitored using the Incucyte live cell imaging platform by analyzing active caspase 3/7 activity over time (FIG. 23).

The effect of anti-TRAILshort antibody on sk-TRAIL cytotoxicity in different human, patient-derived cancer cell lines was evaluated. Cells from patient spleens were received fresh in RPMI and tested for sensitivity to cytotoxicity in the presence of sk-TRAIL at a dose of 1 ng/mL in the presence or absence of increasing doses of anti-TRAIL-short clone HC2LC3 (1.25, 2.5, or 5 µg). Controls were treated with human IgG4 at the same doses. Using the Incucyte, cell death was monitored every 2 hours by the number of cells positive for cleaved Caspase 3/7 over 72 hours (FIG. 24).

Responsiveness to anti-TRAILshort plus sk-TRAIL was greater than that of sk-TRAIL alone in a number of human, patient-derived cancer cell lines. The number of dead cells at 48 hours post treatment of sk-TRAIL at a dose of 1 ng/mL alone or sk-TRAIL (same dose) plus anti-TRAIL short clone HC2LC3 at a dose of 5m/mL is shown in FIG. 25. Responsiveness was defined as a statistically significant increase in the number of dead cells following the addition of the anti-TRAIL short antibody. Statistics for the pair t test is shown.

Responsiveness of human, patient-derived cell lines to anti-TRAILshort both alone and in combination with sk-TRAIL is shown in FIG. 26 and in Table 7. Responsiveness was defined as a statistically significant increase in the number of dead cells over treatment with sk-TRAIL alone.

TABLE 7

Responsiveness of human, patient-derived cell lines to anti-TRAILshort.

| Diagnosis | Responsive to sk-TRAIL + Anti-TRAILshort | Responsive to Anti-TRAIL-short alone |
|---|---|---|
| Non Hodgkin Lymphoma B cell lineage Cyclin D pos | Yes | Yes |
| Splenic diffuse small B cell lymphoma | Yes | Yes |
| Mantel Cell lymphoma (case 1) | Yes | Yes |
| Mantel cell Lymphoma (case 2) | No | No |
| EBV associated lymphoproliferative disorder | Yes (dose dependent) | No |
| Burkitt Lymphoma | Yes | No |
| Angioimmunoblastic T-cell Lymphoma | Yes | No |
| Follicular Lymphoma (case 1) | Yes | No |
| Follicular Lymphoma (case 2) | Yes | Yes |
| Splenic marginal zone lymphoma (case 1) | No | No |
| Splenic marginal zone lymphoma (case 2) | No | No |
| Splenic marginal zone lymphoma (case 3) | No | No |
| Hodgkin's Lymphoma nodular sclerosis (case 1) | No | No |
| Hodgkin's Lymphoma nodular sclerosis (case 2) | No | No |
| CLL/SLL (case 1) | No | No |
| CLL/SLL (case 2) | No | No |
| Recurrent large B-cell lymphoma with extensive T-cell infiltrate | No | No |
| Reactive Follicular Hyperplasia (case 1) | No | No |
| Reactive Follicular Hyperplasia (case 2) | No | No |

TABLE 7-continued

Responsiveness of human, patient-derived cell lines to anti-TRAILshort.

| Diagnosis | Responsive to sk-TRAIL + Anti-TRAILshort | Responsive to Anti-TRAIL-short alone |
|---|---|---|
| Non-lymphoma ITP (case 1) | No | No |
| Non-lymphoma ITP (case 2) | No | No |

Increased TRAILshort expression in cell lines responsive to anti-TRAILshort was observed by quantification of copy number of TRAILshort mRNA using Real time qPCR in various responsive and non-responsive cell lines (FIG. 27A), and by the percent of TRAILshort positivity measured by staining of 3 cell lines using anti-TRAIL-short 2.2 conjugated to CF555 or isotype by flow cytometry (FIG. 27B).

TRAILshort expression in 293T cells and tumor tissues from patients was examined. Immunohistochemistry slides stained for TRAILshort using anti-TRAILshort antibody at a dilution of 1:400 are shown in FIG. 28.

NSG mice implanted with human Jurkat T cell lymphoma cells were effectively treated with the combination of anti-DR5 plus anti-TRAILshort antibody. NSG mice were implanted with Jurkat T cells expressing luciferase through IV injection. Tumors were allowed to become established and treated every 2 weeks with 10 mg/kg every 14 days of either (i) isotype control for TRAILshort and isotype for DR5 antibodies (named Isotype), (ii) anti-TRAILshort antibody clone 2.2 plus an Isotype control for anti-DR5 (named Anti-TRAILshort), (iii) an isotype control for anti-TRAILshort antibody plus anti-DR5 antibody (named Isotype control plus Anti-DR5), or (iv) anti-TRAILshort (2.2) plus anti-DR5 as indicated. Over time, mice were analyzed for luciferase expression by whole body imaging (FIG. 29A). Survival as assessed by Kaplan Meyer analysis (FIG. 29B).

Anti-TRAILshort antibody plus isotype control or anti-TRAILshort antibody plus anti-DR5 antibody resulted in suppressed tumor growth in a mouse xenograft model of human cancer (FIG. 30). NSG mice were implanted subcutaneously with the human diffuse Large B cell lymphoma (HBL-1) cell line and tumor size measured daily. When the tumors reached a size of greater or equal to 100 cubic mm, mice received the indicated treatments by weekly IP injections with 10 mg/kg every 14 days of either (i) isotype controls for TRAILshort and for DR5 antibodies (IC+IC), (ii) anti-TRAILshort antibody clone 2.2 plus an Isotype control for anti-DR5 (2.2+IC), (iii) an isotype control for anti-TRAILshort antibody plus anti-DR5 antibody (IC+DR5), or (iv) anti-TRAILshort (2.2) plus anti-DR5 antibody as indicated (2.2+DR5). Over time, mice were analyzed for tumor size and fold change calculated from baseline (FIG. 30A). Survival as assessed by Kaplan Meyer analysis (FIG. 30B).

Toxicity, and the reversibility of any toxic effect, of anti-TRAILshort antibody Clone 2.2 was examined. Ten C57BL/6 mice (5 males and 5 females) were used. Animals received anti-TRAILshort antibody Clone 2.2 by intravenous bolus on Day 1 at a dose of 10 mg/kg and a volume of 5 ml/kg. Parameters evaluated during the study included the changes in the skin, fur, eyes and mucous membranes, respiratory system, circulatory system, autonomic central nervous system, somatomotor activity, locomotor activity and behavioral pattern, body weight changes, and effects on mortality. At the end of the in-life portion, all the animals were weighed, humanely euthanized, blood was collected for clinical chemistry and hematology analysis, and a gross necropsy was performed. There were no abnormalities or changes in any animal's physical condition, activity, or behavior. Clinical observations for all study animals were performed daily. All study animals were observed twice daily for 7 days. All animals survived the duration of the study. All animals lost bodyweight during the study, however, the terminal bodyweights were collected prior to sacrifice, after fasting, so it is unknown whether the decrease in weight was due to the fasting procedures, the anti-TRAILshort antibody Clone 2.2, or a combination thereof. Clinical pathology investigations on hematology and clinical chemistry were performed on all surviving sturdy animals on Day 8. Terminal blood samples were collected from vena cava or cardiac puncture. No untoward toxicity was observed in a cohort of 10 healthy C57 BL/6 mice over a seven day observation period following IV injection of anti-TRAILshort antibody on day 1 in either male or female animals.

TRAILshort can be detected in tissues by in situ hybridization (ISH; FIG. 31). SIV infected macaque tissues were stained either with TRAIL full length specific probes or TRAILshort specific probes (with sequence 383 bp 5'-tcgt-taga aagactccaa gaatgaaaag gctctgggcc gca-3' 423 bp (SEQ ID NO:31)) from Advanced Cell Diagnostics and visualized at 10×, 20×, and 40× magnification (FIG. 31). SIV infected macaque axillary lymph node tissue stained with both TRAIL specific probe and with TRAILshort specific probe. Similarly, SIV infected macaque spleen tissue stained with both TRAIL specific probe and with TRAILshort specific probe.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A humanized antibody that binds TRAILshort (tumor necrosis factor (TNF)-related apoptosis-inducing ligand (TRAIL) short), wherein said antibody comprises:
    a heavy chain variable region (VH) domain comprising the complementarity-determining regions (CDRs) set forth in SEQ ID NO:1, SEQ ID NO:2, and SEQ ID NO:3 and having at least 85 percent sequence identity to SEQ ID NO:6; and
    a light chain variable region (VL) domain comprising the CDRs set forth in SEQ ID NO:14, SEQ ID NO:15, and SEQ ID NO:16 and having at least 85 percent sequence identity to SEQ ID NO:20.

2. The antibody of claim 1, wherein said antibody comprises the VH domain sequence set forth in SEQ ID NO:6.

3. The antibody of claim 1, wherein said heavy chain comprises the sequence set forth in SEQ ID NO:11.

4. The antibody of claim 1, wherein said antibody comprises the VL domain sequence set forth in SEQ ID NO:20.

5. The antibody of claim 1, wherein said light chain comprises the sequence set forth in SEQ ID NO:25.

6. The antibody of claim 1, wherein said antibody is a chimeric antibody.

7. A method of inducing apoptosis in a mammalian cell, said method comprising:
administering to a mammal the antibody of claim 1.

8. A method of treating a cancer, said method comprising:
administering to a mammal having said cancer a humanized antibody that binds TRAILshort (tumor necrosis factor (TNF)-related apoptosis-inducing ligand (TRAIL) short), said antibody comprising a heavy chain variable region (VH) domain comprising the complementarity-determining regions (CDRs) set forth in SEQ ID NO:1, SEQ ID NO:2, and SEQ ID NO:3 and having at least 85 percent sequence identity to SEQ ID NO:6; and a light chain variable region (VL) domain comprising the CDRs set forth in SEQ ID NO:14, SEQ ID NO:15, and SEQ ID NO:16 and having at least 85 percent sequence identity to SEQ ID NO:20;
wherein said antibody induces apoptosis in a cancer cell from said cancer.

9. The method of claim 8, wherein said cancer is selected from the group consisting of ovarian carcinoma, melanoma, pancreatic carcinoma, T cell malignancies, B cell malignancies, bladder cancer, non-small-cell lung cancer, squamous non-small-cell lung cancer, non-squamous non-small-cell lung cancer colorectal cancer, melanoma, hormone receptor-positive breast cancer, HER2-positive breast cancer, triple-negative breast cancer, cervical cancer, esophageal cancer, head and neck cancer, renal papillary cell cancer, kidney clear cell cancer, renal transitional cell carcinoma, chromophobe renal cell carcinoma, hepatocellular carcinoma, myeloma, and uterine cancer.

10. The method of claim 8, wherein said mammal is a human.

11. The method of claim 8, further comprising administering to said mammal a TRAIL agonist.

12. The method of claim 11, wherein said TRAIL agonist is selected from the group consisting of recombinant TRAIL, an anti-TRAIL-R1 antibody, an anti-TRAIL-R2 antibody, and a TRAIL oligomer.

13. The method of claim 8, further comprising administering to said mammal an additional cancer treatment.

14. The method of claim 13, wherein said additional cancer treatment is selected from the group consisting of a chemotherapy agent, radiation therapy, brachytherapy, and surgery.

15. The method of claim 8, wherein the cancer cell expresses TRAILshort.

* * * * *

UNITED STATES PATENT AND TRADEMARK OFFICE
CERTIFICATE OF CORRECTION

PATENT NO. : 11,136,402 B2
APPLICATION NO. : 16/485056
DATED : October 5, 2021
INVENTOR(S) : Andrew D. Badley Page 1 of 1

It is certified that error appears in the above-identified patent and that said Letters Patent is hereby corrected as shown below:

In the Claims

In Column 78, Line 1, Claim 9, after "lung cancer" please insert -- , --.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 32

<210> SEQ ID NO 1

```
<211> LENGTH: 10
<212> TYPE: PRT
<213> ORGANISM: Artificial Sequence
<220> FEATURE:
<223> OTHER INFORMATION: TRAILshort antibody VH CDR1 domain

<400> SEQUENCE: 1

Gly Tyr Ile Phe Thr Asn Asn Asp Met Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: TRAILshort antibody VH CDR2 domain

<400> SEQUENCE: 2

Gly Ile Asp Pro Gly Asp Gly Arg Thr Lys Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: TRAILshort antibody VH CDR3 domain

<400> SEQUENCE: 3

Gly Arg Gly Gly Tyr Glu Phe Gly Ile Asp Tyr
1               5                   10

<210> SEQ ID NO 4
<211> LENGTH: 118
<212> TYPE: PRT
<213> ORGANISM: Artificial Sequence
<220> FEATURE:
<223> OTHER INFORMATION: TRAILshort antibody VH domain

<400> SEQUENCE: 4

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ile Phe Thr Asn Asn
            20                  25                  30

Asp Met Asn Trp Val Lys Gln Arg Pro Gly Gln Gly Leu Glu Trp Ile
        35                  40                  45

Gly Gly Ile Asp Pro Gly Asp Gly Arg Thr Lys Tyr Asn Glu Lys Phe
    50                  55                  60

Lys Gly Lys Ala Thr Leu Thr Ala Asp Lys Phe Ser Asn Thr Val Tyr
65                  70                  75                  80

Met Gln Leu Ser Ser Leu Thr Ser Glu Asn Ser Ala Val Tyr Phe Cys
                85                  90                  95

Gly Arg Gly Gly Tyr Glu Phe Gly Ile Asp Tyr Trp Gly Gln Gly Thr
            100                 105                 110

Ser Val Thr Val Ser Ser
        115

<210> SEQ ID NO 5
<211> LENGTH: 118
<212> TYPE: PRT
<213> ORGANISM: Artificial Sequence
<220> FEATURE:
```

<223> OTHER INFORMATION: TRAILshort antibody VH domain

<400> SEQUENCE: 5

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Asn
            20                  25                  30

Asp Met Asn Trp Val Gln Gln Ala Pro Gly Lys Gly Leu Glu Trp Met
        35                  40                  45

Gly Gly Ile Asp Pro Gly Asp Gly Arg Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Gly Gly Tyr Glu Phe Gly Ile Asp Tyr Trp Gly Gln Gly Thr
            100                 105                 110

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: TRAILshort antibody VH domain

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Asn
            20                  25                  30

Asp Met Asn Trp Val Arg Gln Ala Pro Gly Gln Gly Leu Glu Trp Met
        35                  40                  45

Gly Gly Ile Asp Pro Gly Asp Gly Arg Thr Lys Tyr Asn Glu Lys Phe
    50                  55                  60

Lys Gly Arg Val Thr Met Thr Arg Asp Thr Ser Thr Asn Thr Val Tyr
65                  70                  75                  80

Met Glu Leu Ser Ser Leu Thr Ser Glu Asp Thr Ala Val Tyr Phe Cys
                85                  90                  95

Gly Arg Gly Gly Tyr Glu Phe Gly Ile Asp Tyr Trp Gly Gln Gly Thr
            100                 105                 110

Thr Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: TRAILshort antibody VH domain

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ser Ser Gly Tyr Ile Phe Thr Asn Asn
            20                  25                  30

Asp Met Asn Trp Val Arg Gln Ala Pro Gly Gln Gly Leu Asp Trp Met 35                  40                  45
Gly Gly Ile Asp Pro Gly Asp Gly Arg Thr Lys Tyr Asn Glu Lys Phe
        50                  55                  60

Lys Gly Arg Val Thr Ile Ser Ala Asp Ile Phe Ser Asn Thr Ala Tyr
 65                  70                  75                  80

Met Glu Leu Asn Ser Leu Thr Ser Glu Asp Thr Ala Val Tyr Phe Cys
                 85                  90                  95

Gly Arg Gly Gly Tyr Glu Phe Gly Ile Asp Tyr Trp Gly Gln Gly Thr
            100                 105                 110

Thr Val Thr Val Ser Ser
            115

<210> SEQ ID NO 8
<211> LENGTH: 118
<212> TYPE: PRT
<213> ORGANISM: Artificial Sequence
<220> FEATURE:
<223> OTHER INFORMATION: TRAILshort antibody VH domain

<400> SEQUENCE: 8

Gln Val Gln Leu Val Glu Ser Gly Ala Glu Val Lys Lys Pro Gly Ala
 1               5                  10                  15

Ser Val Lys Val Ser Cys Lys Val Ser Gly Tyr Ile Phe Thr Asn Asn
             20                  25                  30

Asp Met Asn Trp Val Arg Gln Ala Pro Gly Glu Gly Leu Glu Trp Met
         35                  40                  45

Gly Gly Ile Asp Pro Gly Asp Gly Arg Thr Lys Tyr Asn Glu Lys Phe
        50                  55                  60

Lys Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Gly Arg Gly Gly Tyr Glu Phe Gly Ile Asp Tyr Trp Gly Gln Gly Thr
            100                 105                 110

Thr Val Thr Val Ser Ser
            115

<210> SEQ ID NO 9
<211> LENGTH: 467
<212> TYPE: PRT
<213> ORGANISM: Artificial Sequence
<220> FEATURE:
<223> OTHER INFORMATION: TRAILshort antibody heavy chain

<400> SEQUENCE: 9

Met Gly Trp Thr Leu Val Phe Leu Phe Leu Leu Ser Val Thr Ala Gly
 1               5                  10                  15

Val His Ser Gln Val Gln Leu Gln Gln Ser Gly Pro Glu Leu Val Lys
             20                  25                  30

Pro Gly Ala Ser Val Lys Ile Ser Cys Lys Ala Ser Gly Tyr Ile Phe
         35                  40                  45

Thr Asn Asn Asp Met Asn Trp Val Lys Gln Arg Pro Gly Gln Gly Leu
        50                  55                  60

Glu Trp Ile Gly Gly Ile Asp Pro Gly Asp Gly Arg Thr Lys Tyr Asn
 65                  70                  75                  80

Glu Lys Phe Lys Gly Lys Ala Thr Leu Thr Ala Asp Lys Phe Ser Asn
                 85                  90                  95

-continued

```
Thr Val Tyr Met Gln Leu Ser Ser Leu Thr Ser Glu Asn Ser Ala Val
            100                 105                 110
Tyr Phe Cys Gly Arg Gly Gly Tyr Glu Phe Gly Ile Asp Tyr Trp Gly
        115                 120                 125
Gln Gly Thr Ser Val Thr Val Ser Ser Ala Ser Thr Lys Gly Pro Ser
    130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
    210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465
```

<210> SEQ ID NO 10
<211> LENGTH: 467
<212> TYPE: PRT
<213> ORGANISM: Artificial Sequence
<220> FEATURE:
<223> OTHER INFORMATION: TRAILshort antibody heavy chain

<400> SEQUENCE: 10

```
Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Thr Val Lys Ile Ser Cys Lys Val Ser Gly Tyr Ile Phe
        35                  40                  45

Thr Asn Asn Asp Met Asn Trp Val Gln Gln Ala Pro Gly Lys Gly Leu
    50                  55                  60

Glu Trp Met Gly Gly Ile Asp Pro Gly Asp Gly Arg Thr Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Gly Arg Gly Gly Tyr Glu Phe Gly Ile Asp Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
```

```
                    405                 410                 415
Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 11
<211> LENGTH: 467
<212> TYPE: PRT
<213> ORGANISM: Artificial Sequence
<220> FEATURE:
<223> OTHER INFORMATION: TRAILshort antibody heavy chain

<400> SEQUENCE: 11

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ile Phe
        35                  40                  45

Thr Asn Asn Asp Met Asn Trp Val Arg Gln Ala Pro Gly Gln Gly Leu
    50                  55                  60

Glu Trp Met Gly Gly Ile Asp Pro Gly Asp Gly Arg Thr Lys Tyr Asn
65                  70                  75                  80

Glu Lys Phe Lys Gly Arg Val Thr Met Thr Arg Asp Thr Ser Thr Asn
                85                  90                  95

Thr Val Tyr Met Glu Leu Ser Ser Leu Thr Ser Glu Asp Thr Ala Val
            100                 105                 110

Tyr Phe Cys Gly Arg Gly Gly Tyr Glu Phe Gly Ile Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

```
                290                 295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 12
<211> LENGTH: 467
<212> TYPE: PRT
<213> ORGANISM: Artificial Sequence
<220> FEATURE:
<223> OTHER INFORMATION: TRAILshort antibody heavy chain

<400> SEQUENCE: 12

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ser Ser Val Lys Val Ser Cys Lys Ser Ser Gly Tyr Ile Phe
                35                  40                  45

Thr Asn Asn Asp Met Asn Trp Val Arg Gln Ala Pro Gly Gln Gly Leu
50                  55                  60

Asp Trp Met Gly Gly Ile Asp Pro Gly Asp Gly Arg Thr Lys Tyr Asn
65                  70                  75                  80

Glu Lys Phe Lys Gly Arg Val Thr Ile Ser Ala Asp Ile Phe Ser Asn
                85                  90                  95

Thr Ala Tyr Met Glu Leu Asn Ser Leu Thr Ser Glu Asp Thr Ala Val
                100                 105                 110

Tyr Phe Cys Gly Arg Gly Gly Tyr Glu Phe Gly Ile Asp Tyr Trp Gly
                115                 120                 125

Gln Gly Thr Thr Val Thr Val Ser Ser Ala Ser Thr Lys Gly Pro Ser
                130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
```

```
                180                 185                 190
        Val Leu Gln Ser Ser Gly Leu Tyr Ser Leu Ser Ser Val Val Thr Val
                    195                 200                 205
        Pro Ser Ser Leu Gly Thr Gln Thr Tyr Ile Cys Asn Val Asn His
            210                 215                 220
        Lys Pro Ser Asn Thr Lys Val Asp Lys Val Glu Pro Lys Ser Cys
        225                 230                 235                 240
        Asp Lys Thr His Thr Cys Pro Pro Cys Pro Ala Pro Glu Leu Leu Gly
                        245                 250                 255
        Gly Pro Ser Val Phe Leu Phe Pro Pro Lys Pro Lys Asp Thr Leu Met
                    260                 265                 270
        Ile Ser Arg Thr Pro Glu Val Thr Cys Val Val Val Asp Val Ser His
                    275                 280                 285
        Glu Asp Pro Glu Val Lys Phe Asn Trp Tyr Val Asp Gly Val Glu Val
                    290                 295                 300
        His Asn Ala Lys Thr Lys Pro Arg Glu Glu Gln Tyr Asn Ser Thr Tyr
        305                 310                 315                 320
        Arg Val Val Ser Val Leu Thr Val Leu His Gln Asp Trp Leu Asn Gly
                        325                 330                 335
        Lys Glu Tyr Lys Cys Lys Val Ser Asn Lys Ala Leu Pro Ala Pro Ile
                    340                 345                 350
        Glu Lys Thr Ile Ser Lys Ala Lys Gly Gln Pro Arg Glu Pro Gln Val
                    355                 360                 365
        Tyr Thr Leu Pro Pro Ser Arg Asp Glu Leu Thr Lys Asn Gln Val Ser
                370                 375                 380
        Leu Thr Cys Leu Val Lys Gly Phe Tyr Pro Ser Asp Ile Ala Val Glu
        385                 390                 395                 400
        Trp Glu Ser Asn Gly Gln Pro Glu Asn Asn Tyr Lys Thr Thr Pro Pro
                        405                 410                 415
        Val Leu Asp Ser Asp Gly Ser Phe Phe Leu Tyr Ser Lys Leu Thr Val
                    420                 425                 430
        Asp Lys Ser Arg Trp Gln Gln Gly Asn Val Phe Ser Cys Ser Val Met
                    435                 440                 445
        His Glu Ala Leu His Asn His Tyr Thr Gln Lys Ser Leu Ser Leu Ser
            450                 455                 460
        Pro Gly Lys
        465

<210> SEQ ID NO 13
<211> LENGTH: 467
<212> TYPE: PRT
<213> ORGANISM: Artificial Sequence
<220> FEATURE:
<223> OTHER INFORMATION: TRAILshort antibody heavy chain

<400> SEQUENCE: 13

Met Gly Trp Thr Leu Val Phe Leu Phe Leu Leu Ser Thr Ala Gly
        1               5                   10                  15

Val His Ser Gln Val Gln Leu Val Glu Ser Gly Ala Glu Val Lys Lys
                    20                  25                  30

Pro Gly Ala Ser Val Lys Val Ser Cys Lys Val Ser Gly Tyr Ile Phe
                    35                  40                  45

Thr Asn Asn Asp Met Asn Trp Val Arg Gln Ala Pro Gly Glu Gly Leu
                50                  55                  60

Glu Trp Met Gly Gly Ile Asp Pro Gly Asp Gly Arg Thr Lys Tyr Asn
```

```
                65                  70                  75                  80
            Glu Lys Phe Lys Gly Arg Val Thr Met Thr Glu Asp Thr Ser Thr Asp
                            85                  90                  95

Thr Ala Tyr Met Glu Leu Ser Ser Leu Arg Ser Glu Asp Thr Ala Val
                           100                 105                 110

Tyr Tyr Cys Gly Arg Gly Gly Tyr Glu Phe Gly Ile Asp Tyr Trp Gly
                           115                 120                 125

Gln Gly Thr Thr Val Thr Val Ser Ser Ala Ser Thr Lys Gly Pro Ser
                    130                 135                 140

Val Phe Pro Leu Ala Pro Ser Ser Lys Ser Thr Ser Gly Gly Thr Ala
            145                 150                 155                 160

Ala Leu Gly Cys Leu Val Lys Asp Tyr Phe Pro Glu Pro Val Thr Val
                           165                 170                 175

Ser Trp Asn Ser Gly Ala Leu Thr Ser Gly Val His Thr Phe Pro Ala
                           180                 185                 190

Val Leu Gln Ser Ser Gly Leu Tyr Ser Leu Ser Ser Val Val Thr Val
                           195                 200                 205

Pro Ser Ser Ser Leu Gly Thr Gln Thr Tyr Ile Cys Asn Val Asn His
                    210                 215                 220

Lys Pro Ser Asn Thr Lys Val Asp Lys Lys Val Glu Pro Lys Ser Cys
            225                 230                 235                 240

Asp Lys Thr His Thr Cys Pro Pro Cys Pro Ala Pro Glu Leu Leu Gly
                           245                 250                 255

Gly Pro Ser Val Phe Leu Phe Pro Pro Lys Pro Lys Asp Thr Leu Met
                           260                 265                 270

Ile Ser Arg Thr Pro Glu Val Thr Cys Val Val Val Asp Val Ser His
                    275                 280                 285

Glu Asp Pro Glu Val Lys Phe Asn Trp Tyr Val Asp Gly Val Glu Val
                    290                 295                 300

His Asn Ala Lys Thr Lys Pro Arg Glu Glu Gln Tyr Asn Ser Thr Tyr
            305                 310                 315                 320

Arg Val Val Ser Val Leu Thr Val Leu His Gln Asp Trp Leu Asn Gly
                           325                 330                 335

Lys Glu Tyr Lys Cys Lys Val Ser Asn Lys Ala Leu Pro Ala Pro Ile
                           340                 345                 350

Glu Lys Thr Ile Ser Lys Ala Lys Gly Gln Pro Arg Glu Pro Gln Val
                           355                 360                 365

Tyr Thr Leu Pro Pro Ser Arg Asp Glu Leu Thr Lys Asn Gln Val Ser
                    370                 375                 380

Leu Thr Cys Leu Val Lys Gly Phe Tyr Pro Ser Asp Ile Ala Val Glu
            385                 390                 395                 400

Trp Glu Ser Asn Gly Gln Pro Glu Asn Asn Tyr Lys Thr Thr Pro Pro
                           405                 410                 415

Val Leu Asp Ser Asp Gly Ser Phe Phe Leu Tyr Ser Lys Leu Thr Val
                           420                 425                 430

Asp Lys Ser Arg Trp Gln Gln Gly Asn Val Phe Ser Cys Ser Val Met
                           435                 440                 445

His Glu Ala Leu His Asn His Tyr Thr Gln Lys Ser Leu Ser Leu Ser
                    450                 455                 460

Pro Gly Lys
            465

<210> SEQ ID NO 14
```

```
<211> LENGTH: 17
<212> TYPE: PRT
<213> ORGANISM: Artificial Sequence
<220> FEATURE:
<223> OTHER INFORMATION: TRAILshort antibody VL CDR1 domain

<400> SEQUENCE: 14

Lys Ser Ser Gln Ser Leu Leu Asn Ser Gly Asn Gln Lys Asn Ser Leu
1               5                   10                  15
Ala

<210> SEQ ID NO 15
<211> LENGTH: 7
<212> TYPE: PRT
<213> ORGANISM: Artificial Sequence
<220> FEATURE:
<223> OTHER INFORMATION: TRAILshort antibody VL CDR2 domain

<400> SEQUENCE: 15

Gly Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: TRAILshort antibody VL CDR3 domain

<400> SEQUENCE: 16

Gln Asn Asp His Ser Phe Pro Leu Thr
1               5

<210> SEQ ID NO 17
<211> LENGTH: 113
<212> TYPE: PRT
<213> ORGANISM: Artificial Sequence
<220> FEATURE:
<223> OTHER INFORMATION: TRAILshort antibody VL domain

<400> SEQUENCE: 17

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Ser Leu Ala Trp Tyr Gln Gln Lys Pro Gly Arg
        35                  40                  45

Pro Pro Thr Leu Leu Ile Ser Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Phe Pro Leu Thr Phe Gly Ala Gly Thr Lys Leu Glu Leu
            100                 105                 110

Lys

<210> SEQ ID NO 18
<211> LENGTH: 113
<212> TYPE: PRT
<213> ORGANISM: Artificial Sequence
<220> FEATURE:
<223> OTHER INFORMATION: TRAILshort antibody VL domain
```

-continued

<400> SEQUENCE: 18

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Phe Pro Leu Thr Phe Gly Gln Gly Thr Lys Leu Glu Ile
            100                 105                 110

Lys

<210> SEQ ID NO 19
<211> LENGTH: 113
<212> TYPE: PRT
<213> ORGANISM: Artificial Sequence
<220> FEATURE:
<223> OTHER INFORMATION: TRAILshort antibody VL domain

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Phe Pro Leu Thr Phe Gly Gly Gly Thr Lys Leu Glu Ile
            100                 105                 110

Lys

<210> SEQ ID NO 20
<211> LENGTH: 113
<212> TYPE: PRT
<213> ORGANISM: Artificial Sequence
<220> FEATURE:
<223> OTHER INFORMATION: TRAILshort antibody VL domain

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Ser Leu Ala Trp Tyr Gln Gln Arg Pro Gly His
        35                  40                  45

Pro Pro Lys Leu Leu Leu Tyr Gly Ala Ser Thr Arg Glu Ser Gly Val

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                     85                  90                  95

Asp His Ser Phe Pro Leu Thr Phe Gly Gly Gly Thr Lys Val Glu Ile
                    100                 105                 110

Lys

<210> SEQ ID NO 21
<211> LENGTH: 113
<212> TYPE: PRT
<213> ORGANISM: Artificial Sequence
<220> FEATURE:
<223> OTHER INFORMATION: TRAILshort antibody VL domain

<400> SEQUENCE: 21

Glu Ile Val Leu Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
                 20                  25                  30

Gly Asn Gln Lys Asn Ser Leu Ala Trp Tyr Gln His Lys Pro Gly Arg
             35                  40                  45

Pro Pro Lys Leu Leu Ile Tyr Gly Ala Ser Thr Arg Glu Ser Gly Val
 50                  55                  60

Pro Asp Arg Phe Ser Gly Ser Gly Ser Gly Glu Asp Phe Thr Leu Thr
 65                  70                  75                  80

Ile Ser Ser Leu Gln Ala Glu Asp Val Ala Val Tyr Tyr Cys Gln Asn
                     85                  90                  95

Asp His Ser Phe Pro Leu Thr Phe Gly Pro Gly Thr Lys Val Asp Leu
                    100                 105                 110

Lys

<210> SEQ ID NO 22
<211> LENGTH: 240
<212> TYPE: PRT
<213> ORGANISM: Artificial Sequence
<220> FEATURE:
<223> OTHER INFORMATION: TRAILshort antibody light chain

<400> SEQUENCE: 22

Met Val Ser Ser Ala Gln Phe Leu Gly Leu Leu Leu Leu Cys Phe Gln
  1               5                  10                  15

Gly Thr Arg Cys Asp Ile Val Met Thr Gln Ser Pro Ser Ser Leu Ser
                 20                  25                  30

Val Ser Ala Gly Glu Lys Val Thr Met Ser Cys Lys Ser Ser Gln Ser
             35                  40                  45

Leu Leu Asn Ser Gly Asn Gln Lys Asn Ser Leu Ala Trp Tyr Gln Gln
         50                  55                  60

Lys Pro Gly Arg Pro Pro Thr Leu Leu Ile Ser Gly Ala Ser Thr Arg
 65                  70                  75                  80

Glu Ser Gly Val Pro Asp Arg Phe Thr Gly Ser Gly Ser Gly Thr Asp
                     85                  90                  95

Phe Thr Leu Thr Ile Ser Ser Val Gln Ala Glu Asp Leu Ala Val Tyr
                    100                 105                 110

Tyr Cys Gln Asn Asp His Ser Phe Pro Leu Thr Phe Gly Ala Gly Thr
                115                 120                 125
```

Lys Leu Glu Leu Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 23
<211> LENGTH: 240
<212> TYPE: PRT
<213> ORGANISM: Artificial Sequence
<220> FEATURE:
<223> OTHER INFORMATION: TRAILshort antibody light chain

<400> SEQUENCE: 23

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Gly Asn Gln Lys Asn Ser Leu Ala Trp Tyr Gln Gln
    50                  55                  60

Lys Pro Gly Gln Pro Pro Lys Leu Leu Ile Tyr Gly Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Asn Asp His Ser Phe Pro Leu Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 24

<211> LENGTH: 240
<212> TYPE: PRT
<213> ORGANISM: Artificial Sequence
<220> FEATURE:
<223> OTHER INFORMATION: TRAILshort antibody light chain

<400> SEQUENCE: 24

```
Met Val Ser Ser Ala Gln Phe Leu Gly Leu Leu Leu Cys Phe Gln
1               5                   10                  15

Gly Thr Arg Cys Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Asn Ser Gly Asn Gln Lys Asn Ser Leu Ala Trp Tyr Gln Gln
    50                  55                  60

Lys Pro Gly Gln Pro Pro Lys Leu Leu Ile Tyr Gly Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
                100                 105                 110

Tyr Cys Gln Asn Asp His Ser Phe Pro Leu Thr Phe Gly Gly Gly Thr
            115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 25
<211> LENGTH: 240
<212> TYPE: PRT
<213> ORGANISM: Artificial Sequence
<220> FEATURE:
<223> OTHER INFORMATION: TRAILshort antibody light chain

<400> SEQUENCE: 25

```
Met Val Ser Ser Ala Gln Phe Leu Gly Leu Leu Leu Cys Phe Gln
1               5                   10                  15

Gly Thr Arg Cys Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Asn Ser Gly Asn Gln Lys Asn Ser Leu Ala Trp Tyr Gln Gln
    50                  55                  60

Arg Pro Gly His Pro Pro Lys Leu Leu Leu Tyr Gly Ala Ser Thr Arg
65                  70                  75                  80

Glu Ser Gly Val Pro Asp Arg Phe Ser Gly Ser Gly Ser Gly Thr Asp
```

```
                        85                  90                  95
Phe Thr Leu Thr Ile Ser Ser Leu Gln Ala Glu Asp Val Ala Val Tyr
                100                 105                 110

Tyr Cys Gln Asn Asp His Ser Phe Pro Leu Thr Phe Gly Gly Gly Thr
            115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 26
<211> LENGTH: 240
<212> TYPE: PRT
<213> ORGANISM: Artificial Sequence
<220> FEATURE:
<223> OTHER INFORMATION: TRAILshort antibody light chain

<400> SEQUENCE: 26

```
Met Val Ser Ser Ala Gln Phe Leu Gly Leu Leu Leu Leu Cys Phe Gln
1               5                   10                  15

Gly Thr Arg Cys Glu Ile Val Leu Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Asn Ser Gly Asn Gln Lys Asn Ser Leu Ala Trp Tyr Gln His
    50                  55                  60

Lys Pro Gly Arg Pro Pro Lys Leu Leu Ile Tyr Gly Ala Ser Thr Arg
65                  70                  75                  80

Glu Ser Gly Val Pro Asp Arg Phe Ser Gly Ser Gly Ser Gly Glu Asp
                85                  90                  95

Phe Thr Leu Thr Ile Ser Ser Leu Gln Ala Glu Asp Val Ala Val Tyr
                100                 105                 110

Tyr Cys Gln Asn Asp His Ser Phe Pro Leu Thr Phe Gly Pro Gly Thr
            115                 120                 125

Lys Val Asp Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
```

```
                210                 215                 220
Gln Gly Leu Ser Ser Pro Val Thr Lys Ser Phe Asn Arg Gly Glu Cys
225                 230                 235                 240

<210> SEQ ID NO 27
<211> LENGTH: 149
<212> TYPE: PRT
<213> ORGANISM: Murine

<400> SEQUENCE: 27

Met Gly Trp Ser Trp Ile Ile Leu Phe Leu Leu Ser Gly Thr Ala Gly
1               5                   10                  15

Val His Cys Gln Val Gln Leu Gln Gln Ser Gly Pro Glu Leu Val Lys
                20                  25                  30

Pro Gly Ala Ser Val Lys Ile Ser Cys Lys Ala Ser Gly Tyr Ile Phe
            35                  40                  45

Thr Asn Asn Asp Met Asn Trp Val Lys Gln Arg Pro Gly Gln Gly Leu
        50                  55                  60

Glu Trp Ile Gly Gly Ile Asp Pro Gly Asp Gly Arg Thr Lys Tyr Asn
65                  70                  75                  80

Glu Lys Phe Lys Gly Lys Ala Thr Leu Thr Ala Asp Lys Phe Ser Asn
                85                  90                  95

Thr Val Tyr Met Gln Leu Ser Ser Leu Thr Ser Glu Asn Ser Ala Val
            100                 105                 110

Tyr Phe Cys Gly Arg Gly Gly Tyr Glu Phe Gly Ile Asp Tyr Trp Gly
        115                 120                 125

Gln Gly Thr Ser Val Thr Val Ser Ala Thr Thr Ala Pro Ser
        130                 135                 140

Val Tyr Pro Leu Ala
145

<210> SEQ ID NO 28
<211> LENGTH: 163
<212> TYPE: PRT
<213> ORGANISM: Murine

<400> SEQUENCE: 28

Met Val Leu Met Ser Leu Leu Phe Trp Val Ser Gly Thr Cys Gly Asp
1               5                   10                  15

Ile Val Met Thr Gln Ser Pro Ser Ser Leu Ser Val Ser Ala Gly Glu
                20                  25                  30

Lys Val Thr Met Ser Cys Lys Ser Ser Gln Ser Leu Leu Asn Ser Gly
            35                  40                  45

Asn Gln Lys Asn Ser Leu Ala Trp Tyr Gln Gln Lys Pro Gly Arg Pro
        50                  55                  60

Pro Thr Leu Leu Ile Ser Gly Ala Ser Thr Arg Glu Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Tyr Cys Gln Asn Asp
            100                 105                 110

His Ser Phe Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
        130                 135                 140

Gln Leu Thr Ser Gly Gly Ala Ser Val Val Cys Phe Leu Asn Asn Phe
```

-continued

```
                145                 150                 155                 160

Tyr Pro Lys

<210> SEQ ID NO 29
<211> LENGTH: 330
<212> TYPE: PRT
<213> ORGANISM: Homo sapiens

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 106
<212> TYPE: PRT
```

```
<213> ORGANISM: Homo sapiens

<400> SEQUENCE: 30

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 31
<211> LENGTH: 41
<212> TYPE: DNA
<213> ORGANISM: Artificial Sequence
<220> FEATURE:
<223> OTHER INFORMATION: oligonucleotide probe

<400> SEQUENCE: 31
tcgttagaaa gactccaaga atgaaaaggc tctgggccgc a                    41

<210> SEQ ID NO 32
<211> LENGTH: 101
<212> TYPE: PRT
<213> ORGANISM: Homo sapiens

<400> SEQUENCE: 32

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                85                  90                  95

Leu Trp Ala Ala Lys
            100
```